(12) United States Patent
Hirai et al.

(10) Patent No.: US 11,209,732 B2
(45) Date of Patent: Dec. 28, 2021

(54) NEAR INFRARED ABSORBING COMPOSITION, FILM, INFRARED CUT FILTER, SOLID IMAGE PICKUP ELEMENT, INFRARED ABSORBER, AND COMPOUND

(71) Applicant: FUJIFILM Corporation, Tokyo (JP)

(72) Inventors: Yuki Hirai, Haibara-gun (JP); Daisuke Sasaki, Haibara-gun (JP); Yoshihiro Jimbo, Haibara-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/976,515

(22) Filed: May 10, 2018

(65) Prior Publication Data

US 2018/0259849 A1    Sep. 13, 2018

Related U.S. Application Data

(63) Continuation of application No. PCT/JP2016/082571, filed on Nov. 2, 2016.

(30) Foreign Application Priority Data

Dec. 17, 2015 (JP) .............................. JP2015-246300

(51) Int. Cl.
| | | |
|---|---|---|
| G03F 7/00 | (2006.01) | |
| C08L 101/00 | (2006.01) | |
| C09D 133/16 | (2006.01) | |
| G02B 5/00 | (2006.01) | |
| G02B 5/20 | (2006.01) | |
| G03F 7/038 | (2006.01) | |
| G03F 7/039 | (2006.01) | |
| H01L 27/14 | (2006.01) | |
| H01L 27/146 | (2006.01) | |
| C07D 333/36 | (2006.01) | |
| C07D 519/00 | (2006.01) | |
| C09D 4/00 | (2006.01) | |
| C07D 277/42 | (2006.01) | |
| C07D 333/22 | (2006.01) | |
| C08K 5/45 | (2006.01) | |

(52) U.S. Cl.
CPC .......... G03F 7/0007 (2013.01); C08L 101/00 (2013.01); C09D 133/16 (2013.01); G02B 5/003 (2013.01); G02B 5/208 (2013.01); G03F 7/038 (2013.01); G03F 7/039 (2013.01); H01L 27/14 (2013.01); H01L 27/14623 (2013.01); C07D 277/42 (2013.01); C07D 333/22 (2013.01); C07D 333/36 (2013.01); C07D 519/00 (2013.01); C08K 5/45 (2013.01); C09D 4/00 (2013.01)

(58) Field of Classification Search
CPC ........ G03F 7/0007; G03F 7/038; G03F 7/039; C08L 101/00; C09D 133/16; C09D 4/00; G02B 5/003; G02B 5/208; H01L 27/14; H01L 27/14623; C07D 277/42; C07D 333/22; C07D 333/36; C07D 519/00; C08K 5/45

USPC ......................................................... 252/587
See application file for complete search history.

(56) References Cited

U.S. PATENT DOCUMENTS

| | | |
|---|---|---|
| 5,037,575 A | 8/1991 | Miura et al. |
| 2002/0110767 A1 | 8/2002 | Tanaka et al. |

FOREIGN PATENT DOCUMENTS

| | | | |
|---|---|---|---|
| DE | 4122563 | * | 9/1993 |
| DE | 4122563 A1 | | 9/1993 |
| JP | 62-465 A | | 1/1987 |
| JP | 1-232350 A | | 9/1989 |
| JP | H01232350 | * | 9/1989 |
| JP | 2-13964 A | | 1/1990 |
| JP | 2001-117201 A | | 4/2001 |
| JP | 2009-15114 A | | 1/2009 |
| JP | 2009015114 | * | 1/2009 |
| WO | WO 2008/035533 A1 | | 3/2008 |

OTHER PUBLICATIONS

NIR Absorbing Squarainers by Expension of the Conjugation eith (Aminothiazolyl)Ethenyl Groups, Meier et al., Helvetica Chimica Acta—vol. 87 (2004).*

(Continued)

*Primary Examiner* — Ling Siu Choi
*Assistant Examiner* — Ronald Grinsted
(74) *Attorney, Agent, or Firm* — Birch, Stewart, Kolasch & Birch, LLP

(57) ABSTRACT

A near infrared absorbing composition includes: a squarylium compound represented by the following Formula (1) and having an absorption maximum of 700 nm or longer; and a resin. In Formula (1), $Ar^1$ and $Ar^2$ each independently represent a divalent conjugated group which has a heteroaryl ring having a chalcogen atom, and $R^1$ to $R^4$ each independently represent a hydrogen atom or a substituent. The film and the infrared cut filter are formed of the near infrared absorbing composition. The solid image pickup element includes the infrared cut filter.

(1)

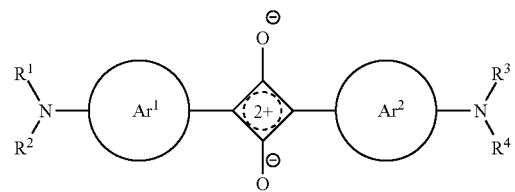

26 Claims, No Drawings

(56) References Cited

OTHER PUBLICATIONS

So et al., Novel symmetric sqaraine chromophore containing triphenylamine for solution processed small molecule bulk heterojunction solar cells, solare energy material & solar cells 95 (2011) 3433-3441.*

International Preliminary Report on Patentability and Written Opinion of the International Searching Authority (Forms PCT/IB/326, PCT/IB/373 and PCT/ISA/237) for International Application No. PCT/JP2016/082571, dated Jun. 28, 2018, with English translation.

International Search Report (Form PCT/ISA/210) for International Application No. PCT/JP2016/082571, dated Jan. 17, 2017, with English translation.

Meier et al., "NIR Absorbing Squaraines by Extension of the Conjugation with (Aminothiazolyl)ethenyl Groups," Helvetica Chimica Acta, vol. 87, 2004, pp. 1109-1118.

Ohira et al., "Electronic and Vibronic Contributions to Two-Photon Absorbtion in Donor-Acceptor-Donor Squaraine Chromophores," Chem. Eur. J., vol. 14, 2008 (published online Oct. 29, 2008), pp. 11082-11091.

Japanese Office Action, dated Jun. 25, 2019, for Japanese Application No. 2017-556407, with an English translation.

Office Action dated Jan. 21, 2020 in Chinese Patent Application No. 201680067876.5, with English translation.

Office Action dated Mar. 25, 2020 in corresponding Taiwanese Patent Application No. TW105136532, with English translation.

* cited by examiner

NEAR INFRARED ABSORBING COMPOSITION, FILM, INFRARED CUT FILTER, SOLID IMAGE PICKUP ELEMENT, INFRARED ABSORBER, AND COMPOUND

CROSS-REFERENCE TO RELATED APPLICATIONS

This application is a Continuation of PCT International Application No. PCT/JP2016/082571 filed on Nov. 2, 2016, which claims priority under 35 U.S.C § 119(a) to Japanese Patent Application No. 2015-246300 filed on Dec. 17, 2015. Each of the above application(s) is hereby expressly incorporated by reference, in its entirety, into the present application.

BACKGROUND OF THE INVENTION

1. Field of the Invention

The present invention relates to a near infrared absorbing composition, a film, an infrared cut filter, a solid image pickup element, an infrared absorber, and a compound.

2. Description of the Related Art

In a video camera, a digital still camera, a mobile phone with a camera function, or the like, a charge coupled device (CCD) or a complementary metal-oxide semiconductor (CMOS), which is a solid image pickup element for a color image, is used. In a light receiving section of the solid image pickup element, a silicon photodiode that detects infrared light is used. Therefore, it is necessary to correct visibility, and the solid image pickup element is used in combination with an infrared cut filter in many cases. As a near infrared absorbing compound, for example, a squarylium compound is known.

JP2009-15114A describes that the following compound or the like is used as an electrophotographic toner.

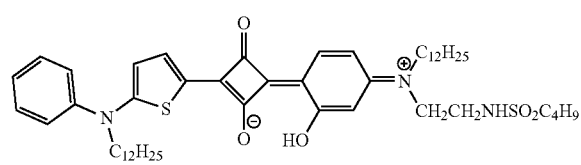

In addition, DE4122563 describes the following compound.

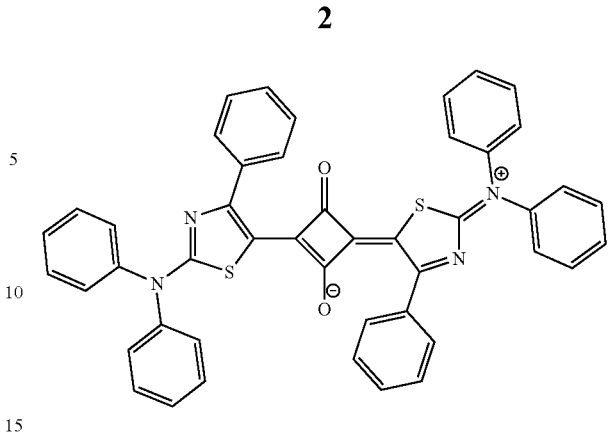

In addition, Chem. Eur. J., 2008, 14, 11082-11091 is an article relating to two-photon absorption of a squarylium compound, and describes two-photon absorption of the following compound.

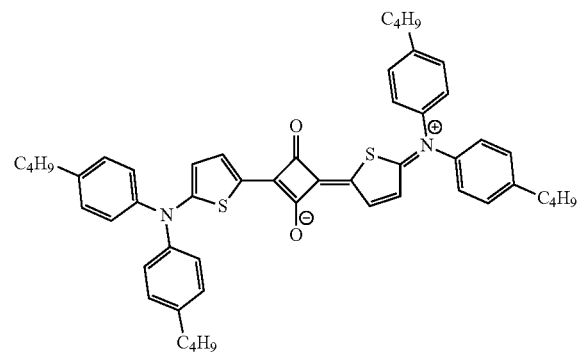

In addition, H. Meier et al., Helv. Chim. Acta 2004, 87, 1109-1118 describes the following compound.

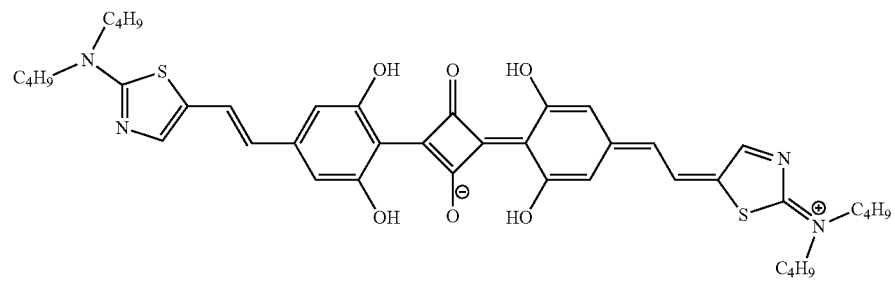

SUMMARY OF THE INVENTION

An infrared cut filter is required to have excellent infrared shielding properties and visible transparency. Recently, further improvement of these properties has been required.

JP2009-15114A describes a technique relating to an electrophotographic toner but does not describe an infrared cut filter. In addition, the present inventors investigated the compound described in JP2009-15114A and found that it is difficult to realize infrared shielding properties and visible transparency at the same time.

In addition DE4122563, Chem. Eur. J., 2008, 14, 11082-11091, and H. Meier et al., Helv. Chim. Acta 2004, 87, 1109-1118 describe specific squarylium compounds but do not describe infrared shielding properties and visible transparency of the compounds. Further, the use of the compounds as an infrared cut filter is neither described nor implied.

Accordingly, an object of the present invention is to provide a near infrared absorbing composition with which a film having excellent infrared shielding properties and visible transparency can be manufactured, a film, an infrared cut filter, a solid image pickup element, an infrared absorber, and a compound.

As a result of investigation in various ways, the present inventors found that the object can be achieved using a near infrared absorbing composition including a squarylium compound represented by the following Formula (1) and having an absorption maximum in a wavelength range of 700 nm or longer and a resin, thereby completing the present invention.

The present invention provides the following.

<1> A near infrared absorbing composition comprising:
a squarylium compound represented by the following Formula (1) and having an absorption maximum of 700 nm or longer; and
a resin,

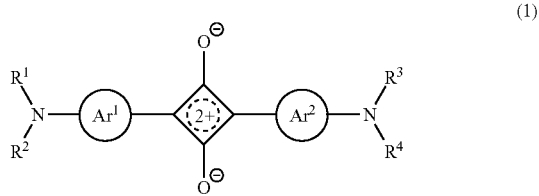

(1)

in formula, $Ar^1$ and $Ar^2$ each independently represent a divalent conjugated group which has a heteroaryl ring having a chalcogen atom, $R^1$ to $R^4$ each independently represent a hydrogen atom or a substituent, $R^1$ may be bonded to $R^2$ or $Ar^1$ to form a ring, $R^3$ may be bonded to $R^4$ or $Ar^2$ to form a ring, in a case where $Ar^1$ represents a monocyclic heteroaryl ring having a chalcogen atom, $R^1$ and $R^2$ each independently represent an aryl group or a heteroaryl group, and in a case where $Ar^2$ represents a monocyclic heteroaryl ring having a chalcogen atom, $R^3$ and $R^4$ each independently represent an aryl group or a heteroaryl group.

<2> The near infrared absorbing composition according to <1>, in which in the squarylium compound, a plane including $Ar^1$ and $Ar^2$ of Formula (1) includes a π-conjugated plane having 16 to 54 atoms.

<3> The near infrared absorbing composition according to <1> or <2>, in which the chalcogen atom is a sulfur atom.

<4> The near infrared absorbing composition according to <1> or <2>, in which $Ar^1$ and $Ar^2$ each independently represent a thiophene ring, a thiazole ring, a fused ring including at least one of a thiophene ring or a thiazole ring, or a divalent conjugated group including a thiophene ring, a thiazole ring or a fused ring including at least one of a thiophene ring or a thiazole ring.

<5> The near infrared absorbing composition according to any one of <1> to <4>,
in which $Ar^1$ and $Ar^2$ each independently include a thiophene ring or a thiazole ring, and
$R^1$ to $R^4$ each independently represent an aryl group or a heteroaryl group.

<6> The near infrared absorbing composition according to <5>,
in which at least one of $R^1$, $R^2$, $R^3$, or $R^4$ represents an aryl group or a heteroaryl group in which the number of atoms constituting a ring is 8 or more.

<7> The near infrared absorbing composition according to <5>,
in which at least one of $R^1$, $R^2$, $R^3$, or $R^4$ represents a naphthyl group.

<8> The near infrared absorbing composition according to any one of <1> to <4>,
in which $Ar^1$ and $Ar^2$ each independently represent a divalent conjugated group which has a π-conjugated plane having 8 or more atoms, and
$R^1$ to $R^4$ each independently represent an alkyl group, an aryl group, or a heteroaryl group.

<9> The near infrared absorbing composition according to <8>,
in which $Ar^1$ and $Ar^2$ each independently represent a fused ring including at least one selected from the group consisting of a thiophene ring and a thiazole ring, or a divalent conjugated group including at least one selected from the group consisting of a thiophene ring, a thiazole ring and a fused ring.

<10> The near infrared absorbing composition according to <8>,
in which $Ar^1$ and $Ar^2$ each independently represent a fused ring including at least one selected from the group consisting of a thiophene ring and a thiazole ring.

<11> The near infrared absorbing composition according to any one of <1> to <10>,
in which at least one selected from the group consisting of $Ar^1$, $Ar^2$, $R^1$, $R^2$, $R^3$, and $R^4$ has a group represented by the following Formula (W),

(W)

in Formula (W), $S^1$ represents a single bond, an arylene group, or a heteroarylene group, $L^1$ represents an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, —$OR^{L2}$—, or a group including a combination of two or more selected from the group consisting of an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, and —$OR^{L2}$, $R^{L1}$ represents a hydrogen atom or an alkyl group, $R^{L2}$ represents an alkylene group, $T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group, in a case where $S^1$ represents a single bond, $L^1$ represents an alkylene group, and $T^1$ represents an alkyl group, the total number of carbon atoms included in $L^1$ and $T^1$ is 5 or more, and in a case where $S^1$ represents an arylene group or a heteroarylene group, the total number of carbon atoms included in $L^1$ and $T^1$ is 5 or more.

<12> The near infrared absorbing composition according to any one of <1> to <4>,
in which the squarylium compound is a compound represented by the following Formula (1a),

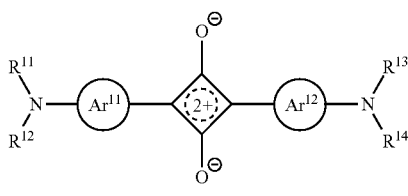

(1a)

Ar$^{11}$ and Ar$^{12}$ each independently represent a thiophene ring, a thiazole ring, or a fused ring including at least one of a thiophene ring or a thiazole ring, R$^{11}$ to R$^{14}$ each independently represent an alkyl group, an aryl group, or a heteroaryl group, R$^{11}$ may be bonded to R$^{12}$ or Ar$^{11}$ to form a ring, R$^{13}$ may be bonded to R$^{14}$ or Ar$^{12}$ to form a ring, in a case where Ar$^{11}$ represents a thiophene ring or a thiazole ring, at least one of R$^{11}$ or R$^{12}$ represents an aryl group having 8 or more atoms, or a heteroaryl group, and in a case where Ar$^{12}$ represents a thiophene ring or a thiazole ring, at least one of R$^{13}$ or R$^{14}$ represents an aryl group having 8 or more atoms, or a heteroaryl group.

<13> A film which is formed of the near infrared absorbing composition according to any one of <1> to <12>.

<14> An infrared cut filter which is formed of the near infrared absorbing composition according to any one of <1> to <12>.

<15> A solid image pickup element comprising the infrared cut filter according to <14>.

<16> An infrared absorber represented by the following Formula (1a),

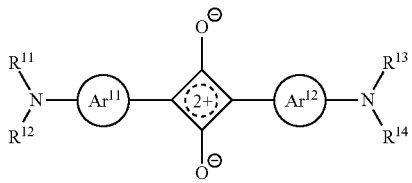

(1a)

in formula, Ar$^{11}$ and Ar$^{12}$ each independently represent a thiophene ring, a thiazole ring, or a fused ring including at least one of a thiophene ring or a thiazole ring, R$^{11}$ to R$^{14}$ each independently represent an alkyl group, an aryl group, or a heteroaryl group, R$^{11}$ may be bonded to R$^{12}$ or Ar$^{11}$ to form a ring, R$^{13}$ may be bonded to R$^{14}$ or Ar$^{12}$ to form a ring, in a case where Ar$^{11}$ represents a thiophene ring or a thiazole ring, at least one of R$^{11}$ or R$^{12}$ represents an aryl group having 8 or more atoms, or a heteroaryl group, and in a case where Ar$^{12}$ represents a thiophene ring or a thiazole ring, at least one of R$^{13}$ or R$^{14}$ represents an aryl group having 8 or more atoms, or a heteroaryl group.

<17> A compound which is represented by the following Formula (1a),

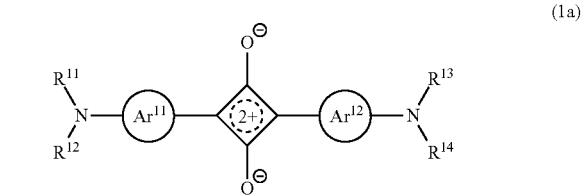

(1a)

in formula, Ar$^{11}$ and Ar$^{12}$ each independently represent a thiophene ring, a thiazole ring, or a fused ring including at least one of a thiophene ring or a thiazole ring, R$^{11}$ to R$^{14}$ each independently represent an alkyl group, an aryl group, or a heteroaryl group, R$^{11}$ may be bonded to R$^{12}$ or Ar$^{11}$ to form a ring, R$^{13}$ may be bonded to R$^{14}$ or Ar$^{12}$ to form a ring, in a case where Ar$^{11}$ represents a thiophene ring or a thiazole ring, at least one of R$^{11}$ or R$^{12}$ represents an aryl group having 8 or more atoms, or a heteroaryl group, and in a case where Ar$^{12}$ represents a thiophene ring or a thiazole ring, at least one of R$^{13}$ or R$^{14}$ represents an aryl group having 8 or more atoms, or a heteroaryl group.

<18> The compound according to <17>, in which at least one of R$^1$, R$^{12}$, R$^{13}$, or R$^{14}$ represents a naphthyl group.

<19> The compound according to <17> or <18>, in which at least one selected from the group consisting of Ar$^{11}$, Ar$^{12}$, R$^{11}$, R$^{12}$, R$^{13}$, and R$^{14}$ has a group represented by the following Formula (W),

$-S^1-L^1-T^1$ (W)

in Formula (W), S$^1$ represents a single bond, an arylene group, or a heteroarylene group, L$^1$ represents an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, —OR$^{L2}$—, or a group including a combination of two or more selected from the group consisting of an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, and —OR$^{L2}$—, R$^{L1}$ represents a hydrogen atom or an alkyl group, R$^{L2}$ represents an alkylene group, T$^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group, in a case where S$^1$ represents a single bond, L$^1$ represents an alkylene group, and T$^1$ represents an alkyl group, the total number of carbon atoms included in L$^1$ and T$^1$ is 5 or more, and in a case where S$^1$ represents an arylene group or a heteroarylene group, the total number of carbon atoms included in L$^1$ and T$^1$ is 5 or more.

According to the present invention, a near infrared absorbing composition can be provided, with which a film having excellent infrared shielding properties and visible transparency can be manufactured. In addition, a film having excellent infrared shielding properties and visible transparency, an infrared cut filter, a solid image pickup element, an infrared absorber, and a compound can be provided.

DESCRIPTION OF THE PREFERRED EMBODIMENTS

In this specification, a total solid content denotes the total mass of components of a composition excluding a solvent. In addition, a solid content denotes a solid content at 25° C.

In this specification, unless specified as a substituted group or as an unsubstituted group, a group (atomic group) denotes not only a group (atomic group) having no substituent but also a group (atomic group) having a substituent. For example, "alkyl group" denotes not only an alkyl group having no substituent (unsubstituted alkyl group) but also an alkyl group having a substituent (substituted alkyl group).

In this specification, "radiation" denotes, for example, a bright light spectrum of a mercury lamp, a far ultraviolet ray represented by excimer laser, an extreme ultraviolet ray (EUV ray), an X-ray, or an electron beam. In addition, in the present invention, "light" denotes an actinic ray or radiation. In this specification, unless specified otherwise, "exposure" denotes not only exposure using a bright light spectrum of a mercury lamp, a far ultraviolet ray represented by excimer laser, an X-ray, an EUV ray, or the like but also drawing using a corpuscular beam such as an electron beam or an ion beam.

In this specification, "near infrared light" denotes light (electromagnetic wave) in a wavelength range of 700 to 2500 nm.

In this specification, "(meth)acrylate" denotes either or both of acrylate or methacrylate, "(meth)allyl" denotes either or both of allyl and methallyl, "(meth)acryl" denotes either or both of acryl and methacryl, and "(meth)acryloyl" denotes either or both of acryloyl and methacryloyl.

In this specification, in a chemical formula, Me represents a methyl group, Et represents an ethyl group, Pr represents a propyl group, Bu represents a butyl group, and Ph represents a phenyl group.

In this specification, the term "step" denotes not only an individual step but also a step which is not clearly distinguishable from another step as long as an effect expected from the step can be achieved.

In this specification, a weight-average molecular weight and a number-average molecular weight are defined as values in terms of polystyrene obtained by gel permeation chromatography (GPC).

<Near Infrared Absorbing Composition>

A near infrared absorbing composition according to the present invention (hereinafter, also referred to as "the composition according to the present invention") includes: a squarylium compound (hereinafter, also referred to as "squarylium compound (1)") represented by the following Formula (1) and having an absorption maximum of 700 nm or longer; and a resin.

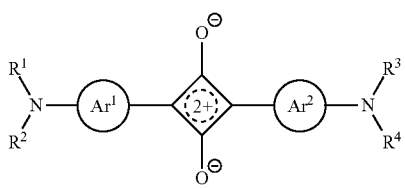

(1)

In the squarylium compound (1), a divalent conjugated group which has a heteroaryl ring having a chalcogen atom at the positions of $Ar^1$ and $Ar^2$. Therefore, it is presumed that contribution of a quinoid form of the compound is improved, and an absorption maximum is shifted to the long wavelength side.

In addition, $Ar^1$ or $Ar^2$ represents a group having a large π-conjugated plane, for example, a divalent conjugated group which has a heteroaryl ring (for example, a fused ring including a thiophene ring or a thiazole ring) of a fused ring having a chalcogen atom, and thus the effective conjugation length is increased. As a result, a gap "highest occupied molecular orbital (HOMO)-lowest unoccupied molecular orbital (LUMO)" is reduced, and the absorption maximum of the compound can be shifted to the long wavelength side.

In addition, in a case where $Ar^1$ represents a monocyclic heteroaryl ring (for example, a thiophene ring or a thiazole ring) having a chalcogen atom, $R^1$ and $R^2$ each independently represent an aryl group or a heteroaryl group. As a result, the effective conjugation length can be increased. In addition, in a case where $Ar^2$ represents a monocyclic heteroaryl ring (for example, a thiophene ring or a thiazole ring) having a chalcogen atom, $R^3$ and $R^4$ each independently represent an aryl group or a heteroaryl group. As a result, the effective conjugation length can be increased. Therefore, the gap "HOMO-LUMO" can be reduced, and thus the absorption maximum of the compound can be easily adjusted to be 700 nm or longer.

Here, examples of a method of adjusting the absorption maximum of the squarylium compound (1) to be 700 nm or longer include a method of adjusting a plane including $Ar^1$ and $Ar^2$ to be a large π-conjugated plane (for example, a method of increasing the conjugation length of a portion interposed between —$NR^1R^2$ and —$NR^3R^4$), and a method of adjusting $R^1$ to $R^4$ to be a conjugated group. In particular, in a case where the plane including $Ar^1$ and $Ar^2$ is a large π-conjugated plane, the spatial gap between HOMO and LUMO can be more effectively increased, and thus the effective conjugation length can be easily increased. Therefore, the absorption maximum of the compound can be easily adjusted to be 700 nm or longer.

According to the investigation, the present inventors found that, among compounds represented by the following Formula (1), a compound having an absorption maximum of 700 nm or longer has excellent visible transparency and infrared shielding properties. Further, the present inventor found that, by mixing the present inventors found that the squarylium compound (1) with a composition including a resin, a film having excellent infrared shielding properties and visible transparency can be manufactured.

In addition, in the squarylium compound (1), $Ar^1$ and $Ar^2$ each independently represent a divalent conjugated group which has a heteroaryl ring of a fused ring having a chalcogen atom. As a result, heat resistance and light fastness are improved, and discoloration caused by heating or light irradiation is not likely to occur. Therefore, with the composition according to the present invention, a film having excellent visible transparency even after heating or light irradiation can be manufactured.

Hereinafter, each component of the composition according to the present invention will be described.

<<Squarylium Compound Represented by Formula (1)>>

The composition according to the present invention includes a squarylium compound (squarylium compound (1)) represented by the following Formula (1) and having an absorption maximum of 700 nm or longer. In the present invention, the absorption maximum of the squarylium compound (1) is preferably 710 nm or longer and more preferably 720 nm or longer. For example, the upper limit is preferably 1200 nm or shorter and more preferably 1000 nm or shorter. By adjusting the absorption maximum to be in the above-described range, a film having excellent infrared shielding properties and visible transparency can be manufactured.

The absorption maximum of the squarylium compound (1) is a value measured using a chloroform solution of the squarylium compound that is adjusted such that an absorbance at the absorption maximum is in a range of 0.7 to 1.2.

The content of the squarylium compound (1) is preferably 0.1 to 70 mass % with respect to the total solid content of the composition. The lower limit is preferably 0.5 mass % or higher and more preferably 1.0 mass % or higher. The upper limit is preferably 60 mass % or lower, and more preferably 50 mass % or lower. In the above-described range, excellent infrared absorption capacity can be imparted. In a case where the composition includes two or more squarylium compounds (1), it is preferable that the total content of the squarylium compounds (1) is in the above-described range.

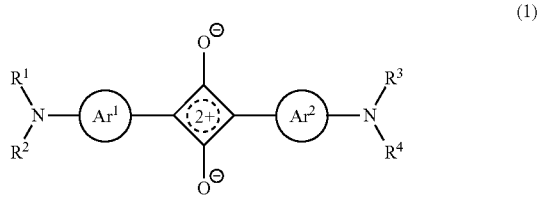

(1)

In the formula, $Ar^1$ and $Ar^2$ each independently represent a divalent conjugated group which has a heteroaryl ring having a chalcogen atom, $R^1$ to $R^4$ each independently represent a hydrogen atom or a substituent, $R^1$ may be bonded to $R^2$ or $Ar^1$ to form a ring, and $R^3$ may be bonded to $R^4$ or $Ar^2$ to form a ring.

In this case, in a case where $Ar^1$ represents a monocyclic heteroaryl ring having a chalcogen atom, $R^1$ and $R^2$ each independently represent an aryl group or a heteroaryl group, and in a case where $Ar^2$ represents a monocyclic heteroaryl ring having a chalcogen atom, $R^3$ and $R^4$ each independently represent an aryl group or a heteroaryl group.

$Ar^1$ and $Ar^2$ each independently represent a divalent conjugated group which has a heteroaryl ring having a chalcogen atom. Examples of the chalcogen atom include a sulfur atom, an oxygen atom, a selenium atom, and a tellurium atom. Among these, a sulfur atom is preferable. In the present invention, the heteroaryl ring refers to an aromatic ring composed of two or more kinds of atoms.

The heteroaryl ring having a chalcogen atom may have a substituent or may be unsubstituted. Examples of the substituent include groups described below in a substituent group T and a group represented by Formula (W). From the viewpoints of spectroscopic characteristics and solubility, it is preferable that the substituent is the group represented by Formula (W). In the present invention, the divalent conjugated group which has a heteroaryl ring having a chalcogen atom may consist of only a heteroaryl ring having a chalcogen atom, or may be a divalent conjugated group which includes a heteroaryl ring having a chalcogen atom and a linking group. It is preferable that the divalent conjugated group consists of only heteroaryl ring having a chalcogen atom.

Examples of the heteroaryl ring having a chalcogen atom include a ring represented by the following (Ht) and a fused ring including a ring represented by the following (Ht). Examples of the fused ring include a fused ring which is composed of two or more rings represented by the following (Ht) and a fused ring which is composed of a ring represented by the following (Ht) and an aromatic hydrocarbon ring and/or a heteroaryl ring not having a chalcogen atom. It is preferable that the heteroaryl ring having a chalcogen atom is a fused ring including at least one selected from the group consisting of a thiophene ring and a thiazole ring. The number of rings composing the fused ring is preferably 2 to 8, more preferably 2 to 5, and still more preferably 2 or 3.

(Ht)

In the formula, $X^1$ and $X^2$ each independently represent a nitrogen atom or $CR^x$. $R^x$ represents a hydrogen atom or a substituent. Examples of the substituent include the substituent group T described below regarding $R^1$ to $R^4$ and a group Formula (W). $Y^1$ represents a chalcogen atom. Examples of the chalcogen atom include a sulfur atom, an oxygen atom, a selenium atom, and a tellurium atom. Among these, a sulfur atom is preferable. * represents a direct bond.

Specific examples of the heteroaryl ring having a chalcogen atom include a thiophene ring and a thiazole ring as monocycles. Examples of the fused ring are as follows.

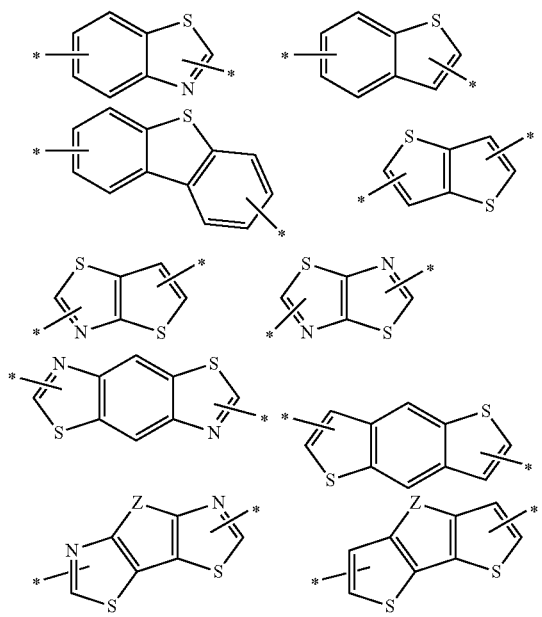

In the formulae, Z represents —$CR_2$—, —CR=CR—, —$SIR_2$—, —CO—, —S—, —SO—, and —$SO_2$—. * represents a direct bond. R represents a hydrogen atom or a substituent. Examples of the substituent include the substituent group T described below regarding $R^1$ to $R^4$ and a group Formula (W).

Examples of an aspect of the divalent conjugated group which has a heteroaryl ring having a chalcogen atom include the following (1) to (5). Among these, the aspect (1) is preferable. In addition, in the aspect (1), it is more preferable that the heteroaryl ring having a chalcogen atom is a fused ring.

(1) A group that consists of only a heteroaryl ring having a chalcogen atom (a divalent conjugated group consisting of a heteroaryl ring having a chalcogen atom)

(2) A group in which two or more heteroaryl rings having a chalcogen atom are bonded to each other through a single bond (3) A group including a combination of one or more heteroaryl rings having a chalcogen atom and a methine chain having one to four methine groups (4) A group in which one or more heteroaryl rings having a chalcogen atom and one or more heteroaryl rings not having a chalcogen atom are bonded to each other through a single bond or a methine chain having one to four methine groups (5) A group in which one or more heteroaryl rings having a chalcogen atom and one or more aromatic hydrocarbon rings are bonded to each other through a single bond or a methine chain having one to four methine groups $Ar^1$ and $Ar^2$ each independently represent preferably a thiophene ring, a thiazole ring, a fused ring including at least one selected from the group consisting of a thiophene ring and a thiazole ring, or a divalent conjugated group including a thiophene ring or a thiazole ring, more preferably a thiophene ring, a thiazole ring, or a fused ring including at least one selected from the group consisting of a thiophene ring and a thiazole ring, and still more preferably a fused ring including at least one selected from the group consisting of a thiophene ring and a thiazole ring.

In addition, it is also preferable that $Ar^1$ and $Ar^2$ each independently represent a divalent conjugated group which has a π-conjugated plane having 8 or more atoms (preferably 8 to 14 atoms and more preferably 8 to 12 atoms). According to this aspect, a film having excellent visible transparency and infrared shielding properties can be easily manufactured.

As the divalent conjugated group which has a π-conjugated plane having 8 or more atoms, a fused ring including at least one selected from the group consisting of a thiophene ring and a thiazole ring, or a divalent conjugated group including at least one selected from the group consisting of a thiophene ring, a thiazole ring, and a fused ring including the above-described ring is preferable, and a fused ring including at least one selected from the group consisting of a thiophene ring and a thiazole ring is more preferable. In the present invention, the π-conjugated plane is composed of atoms other than a hydrogen atom. In (A) conjugated group, the number of atoms in a π-conjugated plane is 10. In (B) conjugated group, the number of atoms in a π-conjugated plane is 12. In (C) conjugated group, the number of atoms in a π-conjugated plane is 8.

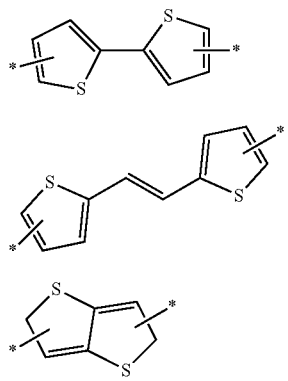

It is preferable that a portion interposed between —$NR^1R^2$ and —$NR^3R^4$ in Formula (1) has a π-conjugated plane having 16 to 54 atoms (preferably 16 to 44 atoms and more preferably 16 to 34 atoms). According to this aspect, visible transparency and infrared shielding properties can be further improved. In the present invention, the t-conjugated plane is composed of atoms other than a hydrogen atom. For example, in the following compound, a portion interposed between —$NR^1R^2$ and —$NR^3R^4$ has a π-conjugated plane having 22 atoms. In a case $Ar^1$ and/or $Ar^2$ has a substituent, the number of atoms described herein refers to the number of atoms in a portion excluding the substituent. Specifically, the number of atoms described herein refers to the number of atoms in a π-conjugated plane that is formed by a structure in which the substituent is substituted with a hydrogen atom.

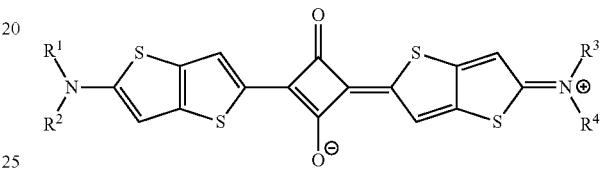

In Formula (1), $R^1$ to $R^4$ each independently represent a hydrogen atom or a substituent. In this case, in a case where $Ar^1$ represents a thiophene ring or a thiazole ring, $R^1$ and $R^2$ each independently represent an aryl group or a heteroaryl group, and in a case where $Ar^2$ represents a thiophene ring or a thiazole ring, $R^3$ and $R^4$ each independently represent an aryl group or a heteroaryl group.

Examples of the substituent represented by $R^1$ to $R^4$ include groups in the substituent group T and the group represented by Formula (W) described below. Among these, an alkyl group, an aryl group, or a heteroaryl group is preferable, and an aryl group or a heteroaryl group is more preferable.

The number of carbon atoms in the alkyl group is preferably 1 to 20, more preferably 1 to 15, and still more preferably 1 to 8. The alkyl group may be linear, branched, or cyclic and is preferably linear or branched.

The number of carbon atoms in the aryl group is preferably 6 to 30, more preferably 6 to 20, and still more preferably 6 to 12. It is preferable that the aryl group is a naphthyl group.

The heteroaryl group is preferably a monocycle or a fused ring, more preferably a monocycle or a fused ring composed of 2 to 8 rings, and still more preferably a monocycle or a fused ring composed of 2 to 4 rings. The number of heteroatoms constituting the ring of the heteroaryl group is preferably 1 to 3. It is preferable that the heteroatoms constituting the ring of the heteroaryl group are a nitrogen atom, an oxygen atom, or a sulfur atom. In the heteroaryl group, the number of atoms constituting a ring is preferably 5 or more, more preferably 6 or more, and still more preferably 8 or more. For example, the upper limit is preferably 30 or less, more preferably 18 or less, and still more preferably 12 or less.

The alkyl group, the aryl group, and the heteroaryl group may have a substituent or may be unsubstituted. Examples of the substituent include the following substituent group T. In addition, the group represented by Formula (W) described below may be used as the substituent.

(Substituent Group T)

The substituent group T includes a halogen atom, a cyano group, a nitro group, an alkyl group, an alkenyl group, an alkynyl group, an aryl group, a heteroaryl group, an aralkyl group, $-OR_Z^1$, $-COR_Z^1$, $-COOR_Z^1$, $-OCOR_Z^1$, $-NR_Z^1R_Z^2$, $-NHCOR_Z^1$, $-CONR_Z^1R_Z^2$, $-NHCONR_Z^1R_Z^2$, $-NHCOOR_Z^1$, $-SR_Z^1$, $-SO_2R_Z^1$, $-SO_2OR_Z^1$, $-NHSO_2R_Z^1$, and $-SO_2NR_Z^1R_Z^2$. $R_Z^1$ to $R_Z^2$ each independently represent a hydrogen atom, an alkyl group, an alkenyl group, an alkynyl group, an aryl group, a heteroaryl group, or an aralkyl group, and $R_Z^1$ to $R^2$ may be bonded to each other to form a ring. In a case where $R_Z^1$ in $-COOR_Z^1$ represents a hydrogen atom (that is, a carboxyl group), the hydrogen atom may be dissociable (that is, a carbonate group) or may be in the form of a salt. In a case where $R_Z^1$ in $-SO_2OR_Z^1$ represents a hydrogen atom (that is, a sulfo group), the hydrogen atom may be dissociable (that is, a sulfonate group) or may be in the form of a salt.

Examples of the halogen atom include a fluorine atom, a chlorine atom, a bromine atom, and an iodine atom.

The number of carbon atoms in the alkyl group is preferably 1 to 20, more preferably 1 to 15, and still more preferably 1 to 8. The alkyl group may be linear, branched, or cyclic and is preferably linear or branched.

The number of carbon atoms in the alkenyl group is preferably 2 to 20, more preferably 2 to 12, and still more preferably 2 to 8. The alkenyl group may be linear, branched, or cyclic and is preferably linear or branched.

The number of carbon atoms in the alkynyl group is preferably 2 to 40, more preferably 2 to 30, and still more preferably 2 to 25. The alkynyl group may be linear, branched, or cyclic and is preferably linear or branched.

The number of carbon atoms in the aryl group is preferably 6 to 30, more preferably 6 to 20, and still more preferably 6 to 12.

An alkyl portion of the aralkyl group is the same as the above-described alkyl group. An aryl portion of the aralkyl group is the same as the above-described aryl group. The number of carbon atoms in the aralkyl group is preferably 7 to 40, more preferably 7 to 30, and still more preferably 7 to 25.

The heteroaryl group is preferably a monocycle or a fused ring, more preferably a monocycle or a fused ring composed of 2 to 8 rings, and still more preferably a monocycle or a fused ring composed of 2 to 4 rings. The number of heteroatoms constituting the ring of the heteroaryl group is preferably 1 to 3. It is preferable that the heteroatoms constituting the ring of the heteroaryl group are a nitrogen atom, an oxygen atom, or a sulfur atom. It is preferable that the heteroaryl group is a 5-membered or 6-membered ring. The number of carbon atoms constituting the ring of the heteroaryl group is preferably 3 to 30, more preferably 3 to 18, and still more preferably 3 to 12.

The alkyl group, the alkenyl group, the alkynyl group, the aralkyl group, the aryl group, and the heteroaryl group may have a substituent or may be unsubstituted. Examples of the substituent include the substituent group T. For example, an alkyl group, an aryl group, or a heteroaryl group can be used. In addition, the group represented by Formula (W) described below may be used as the substituent.

In Formula (1), $R^1$ may be bonded to $R^2$ or $Ar^1$ to form a ring, and $R^3$ may be bonded to $R^4$ or $Ar^2$ to form a ring. Examples of the ring which is formed by $R^1$ being bonded to $R^2$ or $Ar^1$ or the ring which is formed by $R^3$ being bonded to $R^4$ or $Ar^2$ include an alicyclic ring (a nonaromatic hydrocarbon ring), an aromatic ring, and a heterocycle. The ring may be a monocycle or a polycycle. Examples of a linking group for forming the ring include a divalent linking group selected from the group consisting of $-CO-$, $-O-$, $-NH-$, an alkylene group having 1 to 10 carbon atoms, and a combination thereof.

Examples of a structure in which $R^1$ ($R^3$) is bonded to $R^2$ ($R^4$) or $Ar^1$ ($Ar^2$) to form a ring include the following structure. In the following structural formula, X represents a hydrogen atom or a substituent.

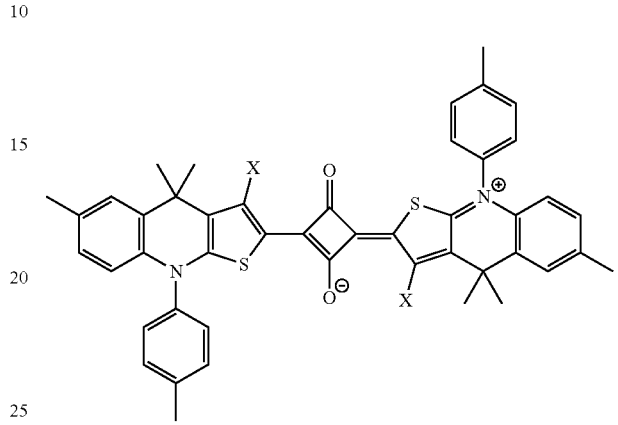

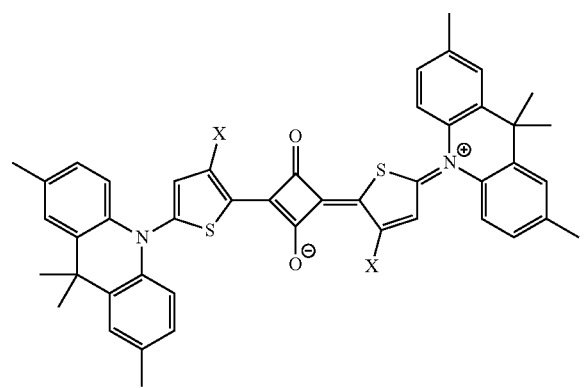

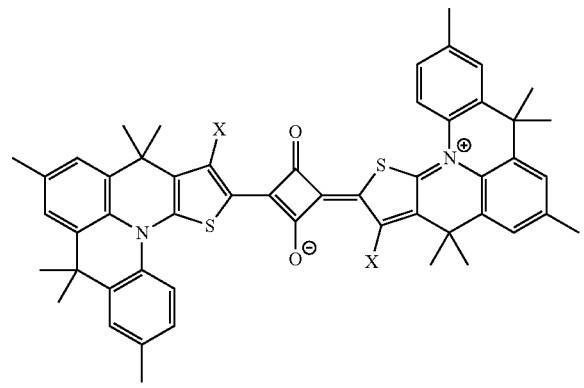

-continued

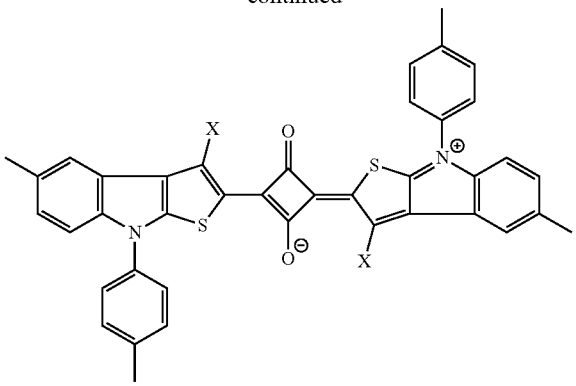

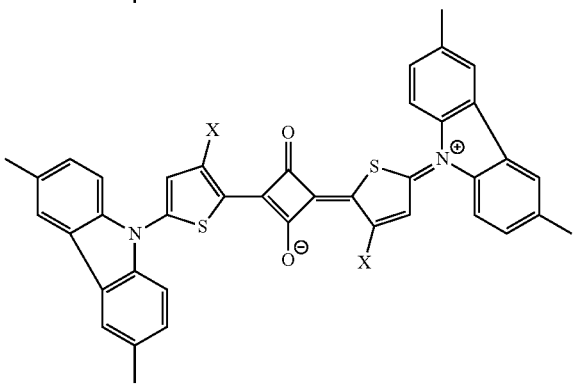

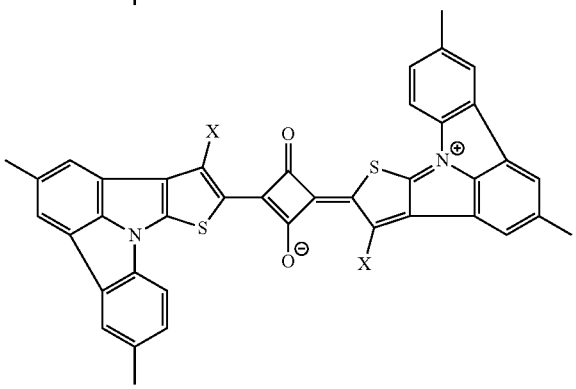

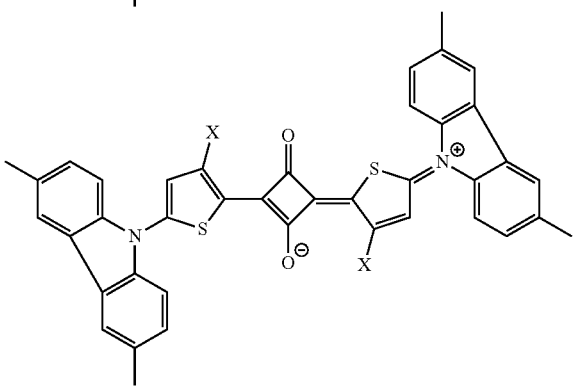

Examples of a preferable aspect of Formula (1) include the following <1> and <2>. Among these, <2> is preferable.

<1> In Formula (1), $Ar^1$ and $Ar^2$ each independently include a thiophene ring or a thiazole ring, and $R^1$ to $R^4$ each independently represent an aryl group or a heteroaryl group <2> In Formula (1), $Ar^1$ and $Ar^2$ each independently represent a divalent conjugated group which has a π-conjugated plane having 8 or more atoms, and $R^1$ to $R^4$ each independently represent an alkyl group, an aryl group, or a heteroaryl group In the aspect <1>, it is preferable that at least one of $R^1$, $R^2$, $R^3$, or $R^4$ represents an aryl group in which the number of atoms constituting a ring is 8 or more or a heteroaryl group in which the number of atoms constituting a ring is 8 or more. According to this aspect, visible transparency and infrared shielding properties can be further improved. In addition, it is preferable that the aryl group or the heteroaryl group is a fused ring. Specific examples of the fused ring include a naphthyl group and the following group. Among these, a naphthyl group is preferable. In the following structural formula, * represents a direct bond to a nitrogen atom.

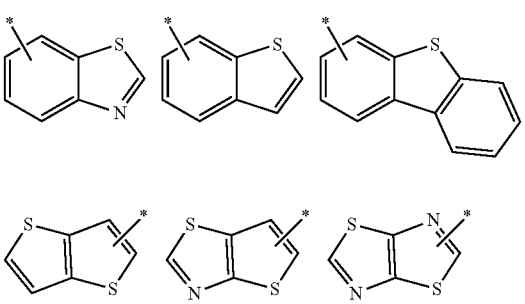

In the aspect <2>, it is preferable that $Ar^1$ and $Ar^2$ each independently represent a fused ring including at least one selected from the group consisting of a thiophene ring and a thiazole ring, or a divalent conjugated group including at least one selected from the group consisting of a thiophene ring, a thiazole ring, and a fused ring including the above-described ring, and it is more preferable that $Ar^1$ and $Ar^2$ each independently represent a fused ring including at least one selected from the group consisting of a thiophene ring and a thiazole ring. According to this aspect, visible transparency and infrared shielding properties can be further improved.

In the squarylium compound (1), it is also preferable that at least one selected from the group consisting of $Ar^1$, $Ar^2$, $R^1$, $R^2$, $R^3$, and $R^4$ has a group represented by the following Formula (W).

According to this aspect, solubility of the compound in a solvent, a resin, or the like can be improved, and aggregation, precipitation, or the like of the compound in the composition can be suppressed. Therefore, in a case where a film is manufactured using the composition according to the present invention, defects derived from insoluble matter or the like can be suppressed, a uniform and high-quality film can be manufactured.

In a case where $Ar^1$ ($Ar^2$) has a substituent, it is preferable that $Ar^1$ ($Ar^2$) does not have an aryl group and a heteroaryl group in the ortho-position with respect to the squaric acid site. For example, in a case where an aryl group is present in the ortho-position as in the following compound, a bond is twisted due to a steric hindrance, which is likely to cause a shift of the absorption maximum to the short wavelength side or deterioration of fastness. Further, subsidiary absorption increases due to transition from the aryl group in the ortho-position, visible transparency may deteriorate.

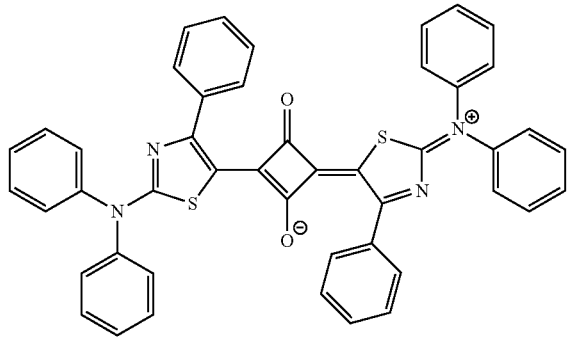 [SMILES: O=C1C(c2sc(N(c3ccccc3)c3ccccc3)nc2-c2ccccc2)=C([O-])/C1=C1/SC(=[N+](c2ccccc2)c2ccccc2)N=C1c1ccccc1]

(Group Represented by Formula (W))

The group represented by Formula (W) will be described.

In Formula (W), $S^1$ represents a single bond, an arylene group, or a heteroarylene group.

$L^1$ represents an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, —OR$^{L2}$—, or a group including a combination of two or more kinds selected from the group consisting of an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, and —OR$^{L2}$—. R$^{L1}$ represents a hydrogen atom or an alkyl group, and R$^{L2}$ represents an alkylene group.

$T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group.

In a case where $S^1$ represents a single bond, $L^1$ represents an alkylene group, and $T^1$ represents an alkyl group, the total number of carbon atoms included in $L^1$ and $T^1$ is 5 or more.

In a case where $S^1$ represents an arylene group or a heteroarylene group, the total number of carbon atoms included in $L^1$ and $T^1$ is 5 or more.

In Formula (W), $S^1$ represents a single bond, an arylene group, or a heteroarylene group. It is preferable that $S^1$ represents a single bond.

The arylene group may be a monocycle or a polycycle. It is preferable that the arylene group is a monocycle. The number of carbon atoms in the arylene group is preferably 6 to 20 and more preferably 6 to 12.

The heteroarylene group may be a monocycle or a polycycle. It is preferable that the heteroarylene group is a monocycle. The number of heteroatoms constituting the ring of the heteroarylene group is preferably 1 to 3. It is preferable that the heteroatoms constituting the ring of the heteroarylene group are a nitrogen atom, an oxygen atom, a sulfur atom, or a selenium atom. The number of carbon atoms constituting the ring of the heteroarylene group is preferably 3 to 30, more preferably 3 to 18, and still more preferably 3 to 12.

In Formula (W), $L^1$ represents an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, —OR$^{L2}$—, or a group including a combination of two or more kinds selected from the group consisting of an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, and —OR$^{L2}$—. R$^{L1}$ represents a hydrogen atom or an alkyl group, and R$^{L2}$ represents an alkylene group. It is preferable that $L^1$ represents an alkylene group, an alkenylene group, an alkynylene group, —O—, —S—, —NR$^{L1}$—, —COO—, —OCO—, —CONR$^{L1}$—, —SO$_2$—, —OR$^{L2}$—, or a group including a combination of the above-described groups. From the viewpoints of flexibility and solvent solubility, an alkylene group, an alkenylene group, —O—, —OR$^{L2}$—, or a group including a combination of the above-described groups is more preferable, an alkylene group, an alkenylene group, —O—, or —OR$^{L2}$— is still more preferable, and an alkylene group, —O—, or —OR$^{L2}$— is even still more preferable.

The number of carbon atoms in the alkylene group represented by $L^1$ is preferably 1 to 40. The lower limit is more preferably 3 or more, still more preferably 5 or more, even still more preferably 10 or more, and even yet still more preferably 13 or more. The upper limit is more preferably 35 or less and still more preferably 30 or less. The alkylene group may be linear, branched, or cyclic and is preferably linear or branched and more preferably branched. For example, the number of branches is preferably 2 to 10 and more preferably 2 to 8. In a case where the number of branches is in the above-described range, solvent solubility is excellent.

The number of carbon atoms in the alkenylene group or the alkynylene group represented by $L^1$ is preferably 2 to 40. For example, the lower limit is more preferably 3 or more, still more preferably 5 or more, even still more preferably 8 or more, and even yet still more preferably 10 or more. The upper limit is more preferably 35 or less and still more preferably 30 or less. The alkenylene group and the alkynylene group may be linear or branched, and is preferably linear or branched, and is still more preferably branched. The number of branches is preferably 2 to 10 and more preferably 2 to 8. In a case where the number of branches is in the above-described range, solvent solubility is excellent.

R$^{L1}$ represents a hydrogen atom or an alkyl group and preferably a hydrogen atom. The number of carbon atoms in the alkyl group is preferably 1 to 20, more preferably 1 to 10, still more preferably 1 to 4, and even still more preferably 1 or 2. The alkyl group may be linear or branched.

R$^{L2}$ represents an alkylene group. The alkylene group represented by R$^{L2}$ has the same definition and the same preferable range as the alkylene group described above regarding $L^1$.

In Formula (W), $T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group.

The number of carbon atoms in the alkyl group, the alkyl group having a trialkylsilyl group, or the alkyl group having a trialkoxysilyl group is preferably 1 to 40. The lower limit is more preferably 3 or more, still more preferably 5 or more, even still more preferably 10 or more, and even yet still more preferably 13 or more. The upper limit is more preferably 35 or less and still more preferably 30 or less. The alkyl group may be linear, branched, or cyclic and is preferably linear or branched.

The aryl group and the heteroaryl group have the same definitions and the same preferable ranges as the aryl group and the heteroaryl group described above regarding $R^1$ and $R^2$.

In a case where $S^1$ represents a single bond, $L^1$ represents an alkylene group, and $T^1$ represents an alkyl group in Formula (W), the total number of carbon atoms in $L^1$ and $T^1$ is preferably 5 or more, and from the viewpoint of solvent solubility, is more preferably 6 or more, and still more preferably 8 or more. For example, the upper limit is preferably 40 or less and more preferably 35 or less. In addition, in a case where $S^1$ represents an arylene group or a heteroarylene group, the total number of carbon atoms in $L^1$ and $T^1$ is preferably 5 or more, and from the viewpoint of solvent solubility, is more preferably 6 or more, and still more preferably 8 or more. For example, the upper limit is preferably 40 or less and more preferably 35 or less.

In a case where the number of carbon atoms in the -$L^1$-$T^1$ portion is 5 or more, solvent solubility is excellent, defects derived from insoluble matter or the like can be suppressed, and a uniform and high-quality film can be manufactured. Further, by adjusting the number of carbon atoms in the -$L^1$-$T^1$ portion to be 5 or more, crystallinity can be suppressed. In general, in a case where the crystallinity of a compound is high, crystallization of the compound progresses during heating of the film, and absorption properties of the film may change. However, since the crystallinity of the compound can be suppressed, crystallization of the compound during heating can be suppressed, and a variation in the absorption properties of the film after heating can be suppressed.

In the present invention, in a preferable aspect of Formula (W), $S^1$ represents a single bond, $L^1$ represents an alkylene group, an alkenylene group, an alkynylene group, —O—, —S—, —NR$^{L1}$—, —COO—, —OCO—, —CONR$^{L1}$—, —SO$_2$—, —OR$^{L2}$—, or a group including a combination of the above-described groups, and $T^1$ represents an alkyl group or a trialkylsilyl group. As $L^1$, an alkylene group, an alkenylene group, —O—, —OR$^{L2}$—, or a group including a combination of the above-described groups is more preferable, an alkylene group, an alkenylene group, —O—, or —OR$^{L2}$— is still more preferable, and an alkylene group, —O—, or —OR$^{L2}$— is even still more preferable. As $T^1$, an alkyl group is more preferable.

It is preferable that the -$L^1$-$T^1$ portion in Formula (W) has a branched alkyl structure. Specifically, it is more preferable that the -$L^1$-$T^1$ portion is a branched alkyl group or a branched alkoxy group. The number of branches in the -$L^1$-$T^1$ portion is preferably 2 to 10 and more preferably 2 to 8. The number of carbon atoms in the -$L^1$-$T^1$ portion is preferably 5 or more, more preferably 9 or more, and still more preferably 10 or more. For example, the upper limit is preferably 40 or less and more preferably 35 or less.

It is preferable that the -$L^1$-$T^1$ portion in Formula (W) has asymmetric carbon. According to this aspect, the squarylium compound (1) can include a plurality of optical isomers. As a result, the solvent solubility of the compound (1) can be further improved. The number of asymmetric carbon atoms is preferably 1 or more. The upper limit of asymmetric carbon atoms is not particularly limited and, for example, is preferably 4 or less.

As shown below, cations in Formula (1) are present without localized.

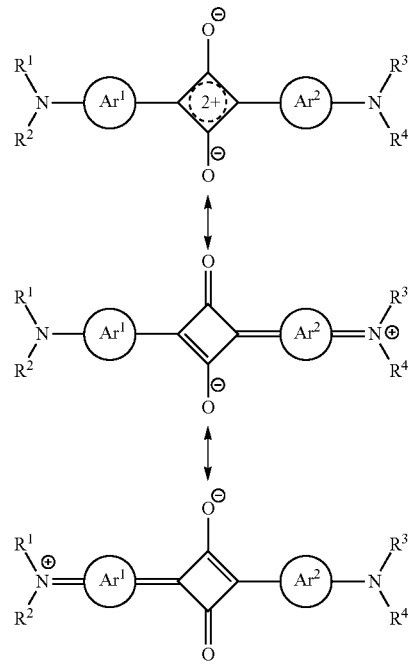

In the present invention, it is preferable that the squarylium compound (1) is a compound represented by the following Formula (1a). The compound represented by Formula (1a) is also the compound according to the present invention.

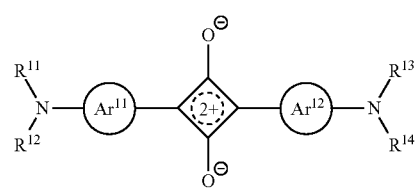

(1a)

In the formula, $Ar^{11}$ and $Ar^{12}$ each independently represent a thiophene ring, a thiazole ring, or a fused ring including at least one of a thiophene ring or a thiazole ring.

$R^{11}$ to $R^{14}$ each independently represent an alkyl group, an aryl group, or a heteroaryl group.

$R^{11}$ may be bonded to $R^{12}$ or $Ar^{11}$ form a ring.

$R^{13}$ may be bonded to $R^{14}$ or $Ar^{12}$ to form a ring.

In a case where $Ar^{11}$ represents a thiophene ring or a thiazole ring, at least one of $R^{11}$ or $R^{12}$ represents an aryl group having 8 or more atoms, or a heteroaryl group.

In a case where $Ar^{12}$ represents a thiophene ring or a thiazole ring, at least one of $R^{13}$ or $R^{14}$ represents an aryl group having 8 or more atoms, or a heteroaryl group.

Examples of the fused ring including at least one selected from the group consisting of a thiophene ring and a thiazole ring which is represented by $Ar^{11}$ and $Ar^{12}$ are the same as the examples of the fused ring described above regarding $Ar^1$ and $Ar^2$, and preferable ranges thereof are also the same. The ring represented by $Ar^{11}$ and $Ar^{12}$ may have a substituent or may be unsubstituted. Examples of the substituent include the substituent group T and the group represented by Formula (W). Among these, the group represented by Formula (W) is preferable.

The alkyl group, the aryl group, and the heteroaryl group represented by $R^1$ to $R^{14}$ have the same definitions and the same preferable ranges as the alkyl group, the aryl group, and the heteroaryl group described above regarding $R^1$ to $R^4$. The alkyl group, the aryl group, and the heteroaryl group represented by $R^{11}$ to $R^{14}$ may have a substituent or may be unsubstituted. Examples of the substituent include the substituent group T and the group represented by Formula (W). Among these, the group represented by Formula (W) is preferable.

Examples of the ring which is formed by $R^{11}$ being bonded to $R^{12}$ or $Ar^{11}$ and the ring which is formed by $R^{13}$ being bonded to $R^{14}$ or $Ar^{12}$ are the same as the examples of the ring which is formed by $R^1$ being bonded to $R^2$ or $Ar^1$ described above regarding Formula (1), and preferable ranges thereof are also the same.

In Formula (1a), it is also preferable that at least one selected from the group consisting of $Ar^{11}$, $Ar^{12}$, $R^{11}$, $R^{12}$, $R^{13}$, and $R^{14}$ has the group represented by Formula (W).

Specific examples of the squarylium compound (1) include compounds shown below, but the squarylium compound (1) is not limited thereto.

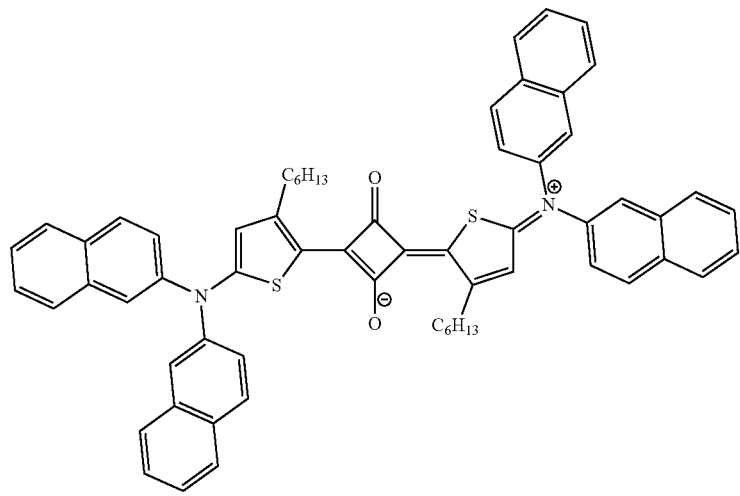

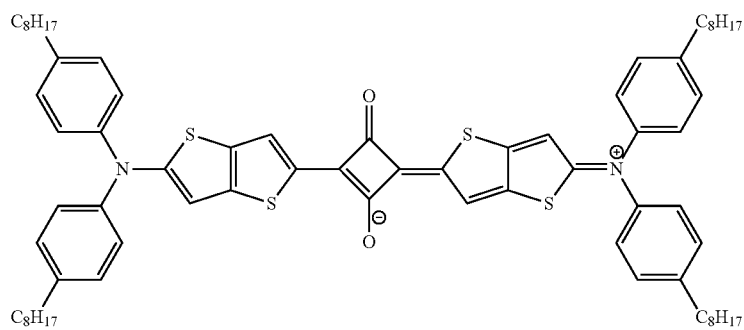

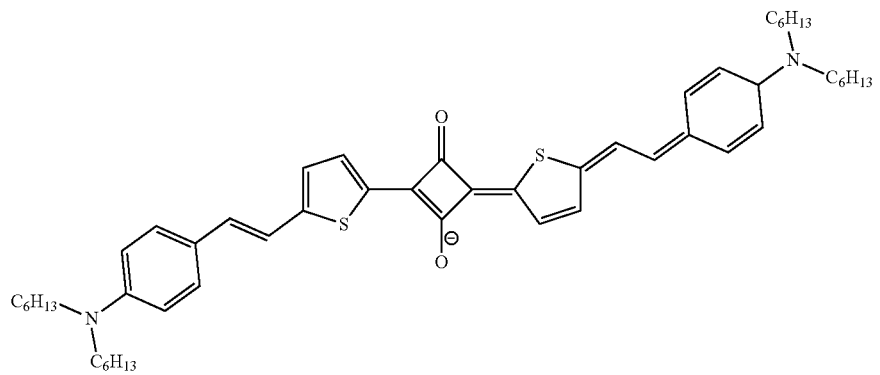

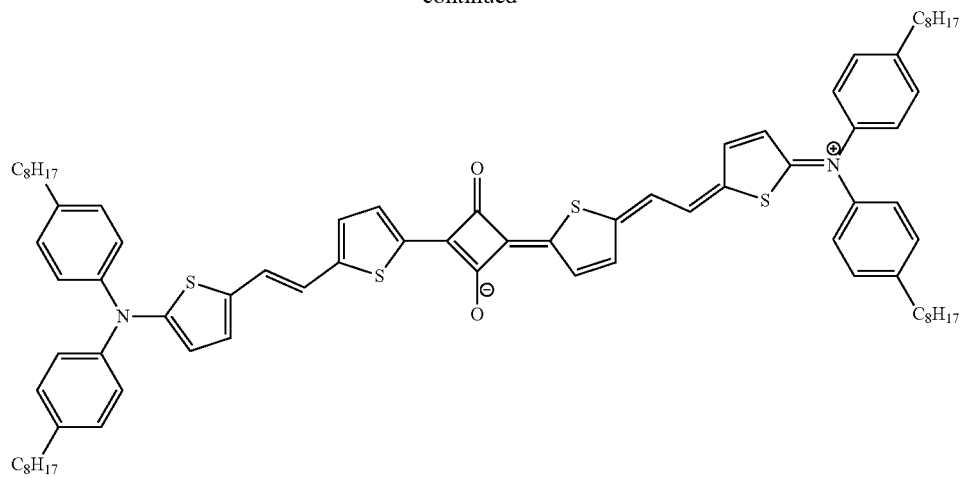
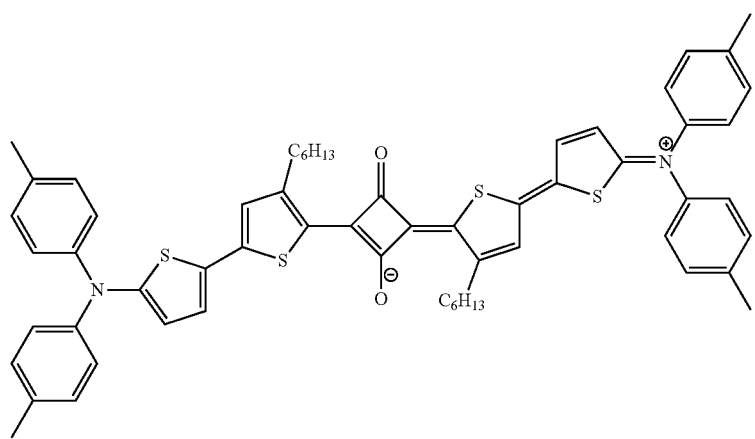
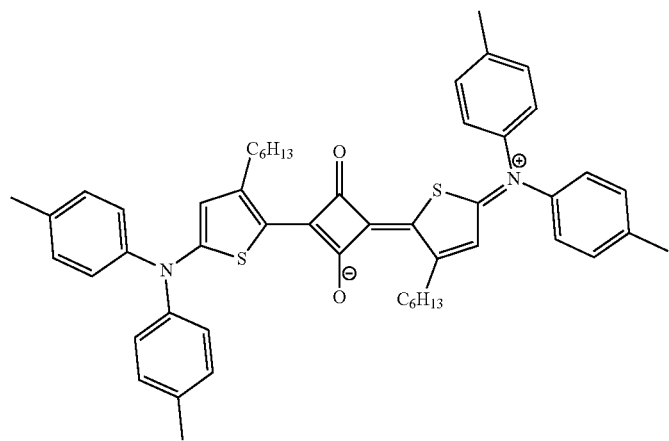

-continued
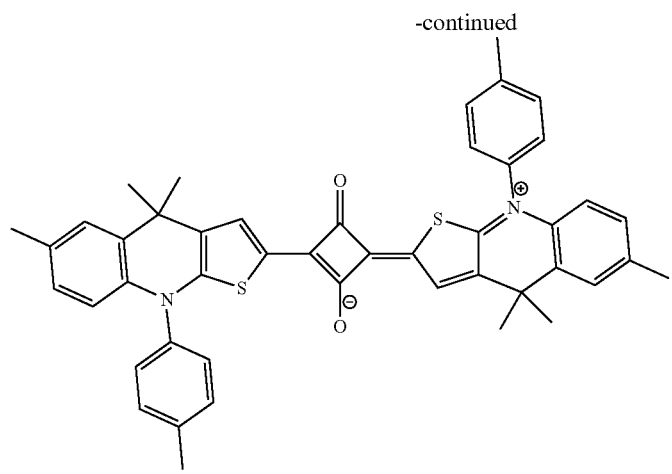
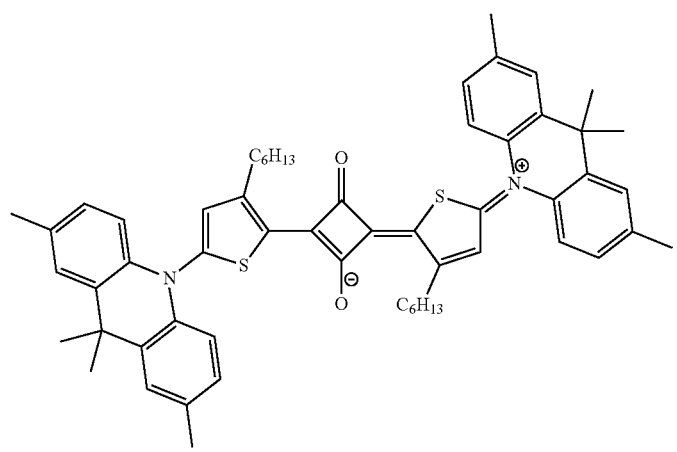
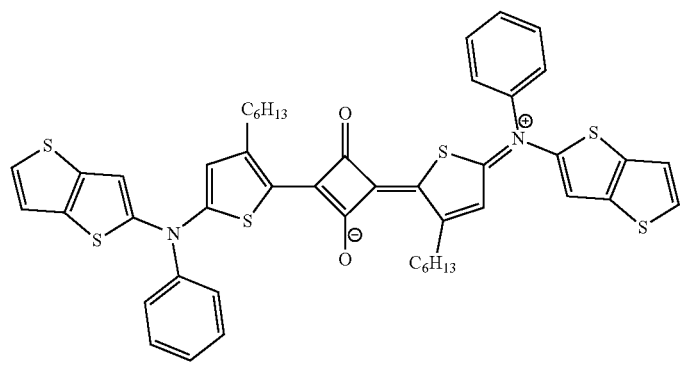

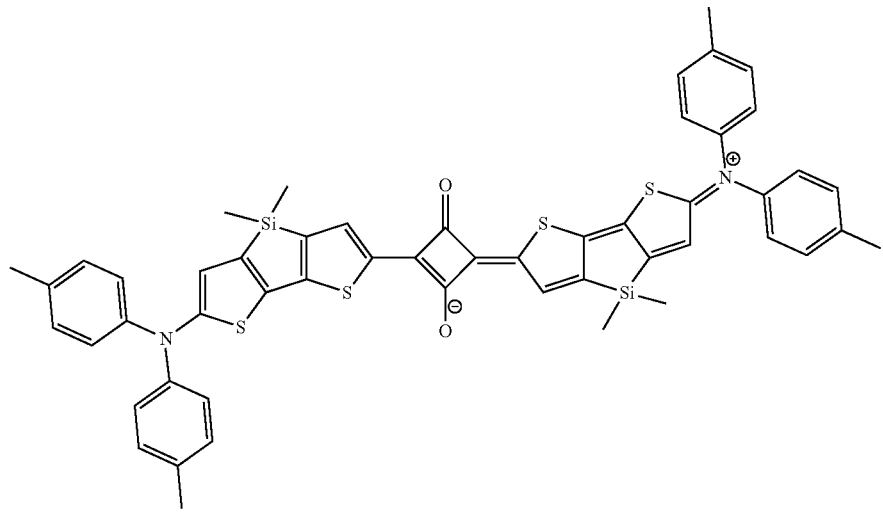
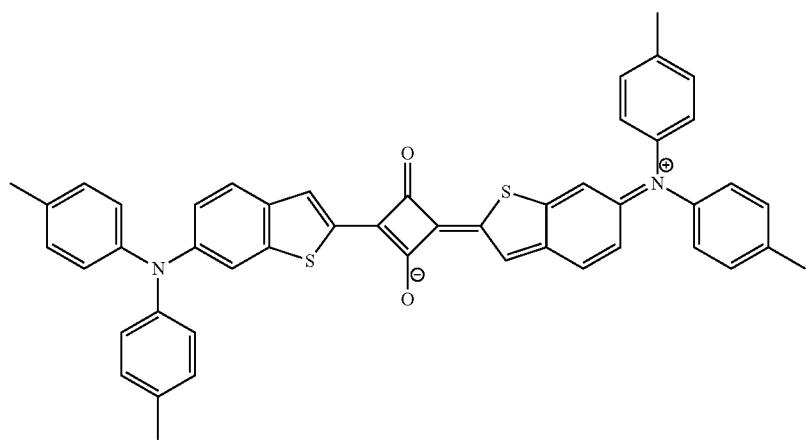
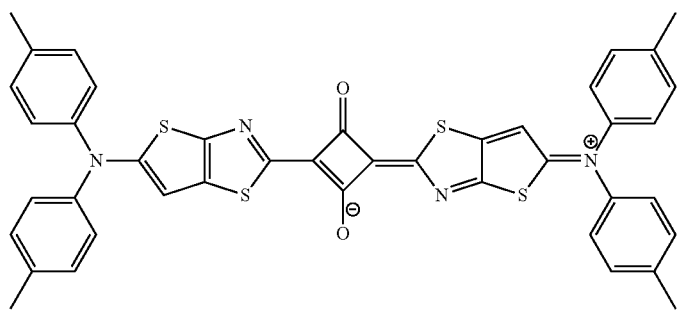
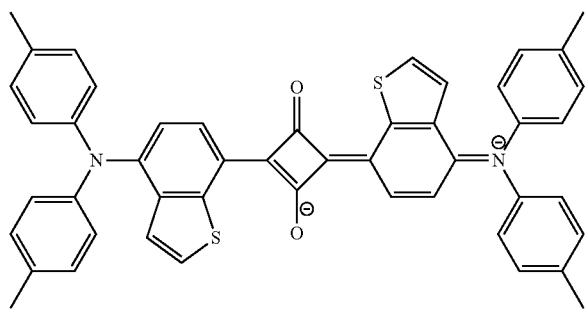

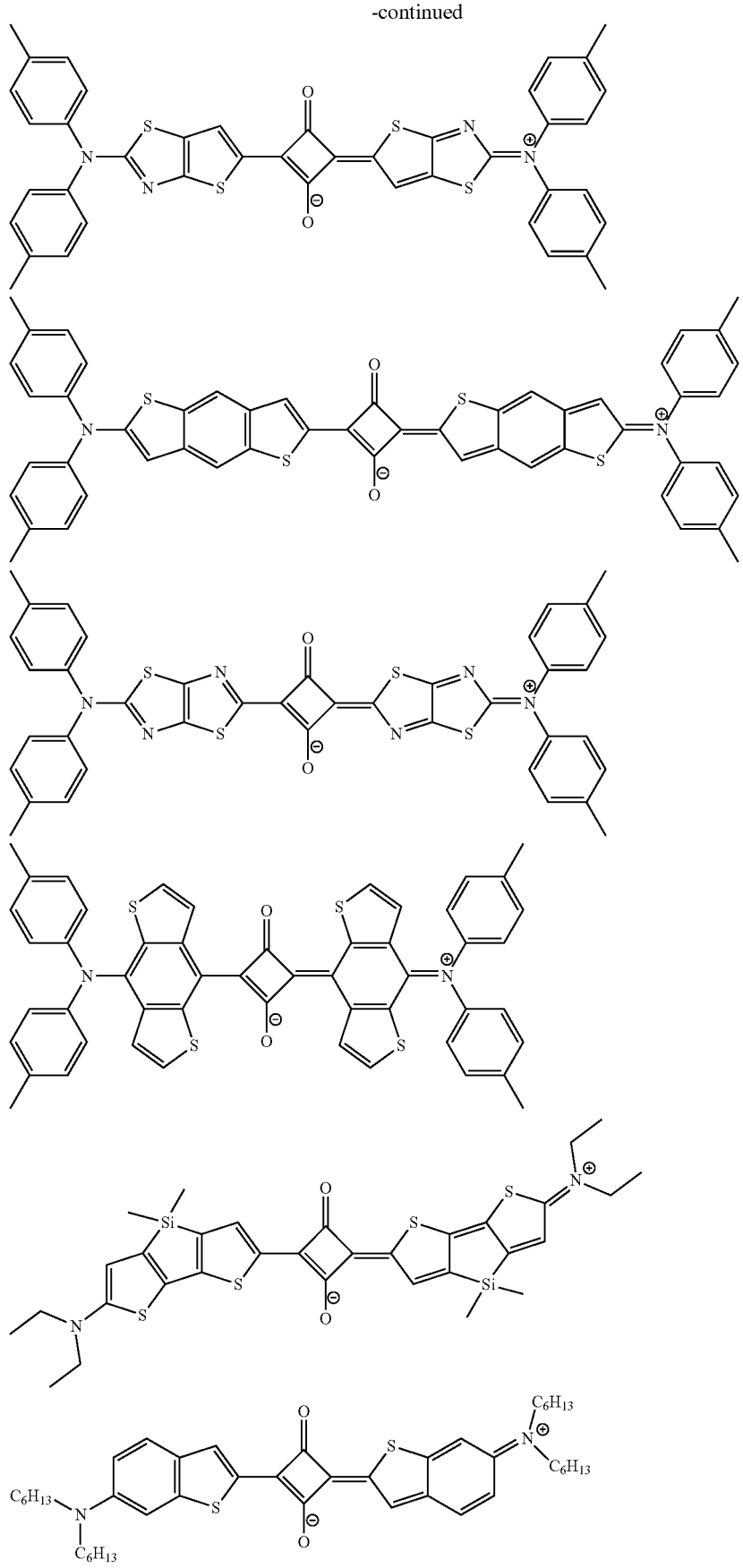

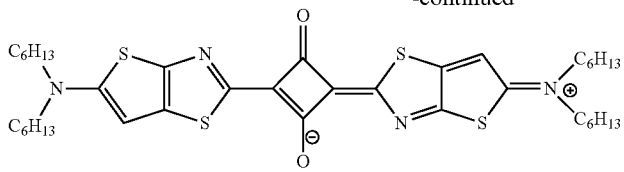

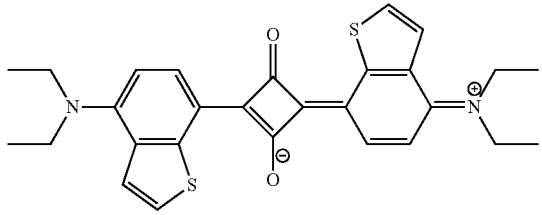

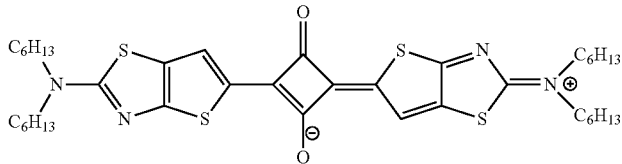

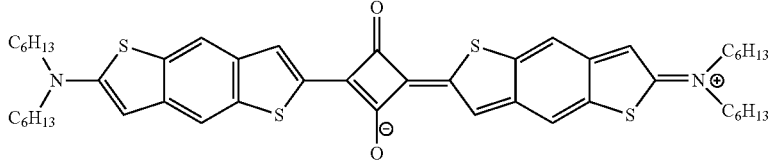

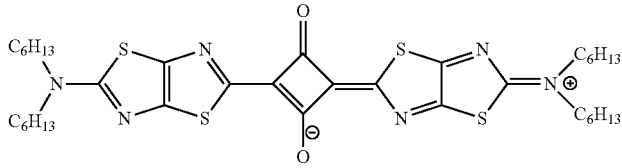

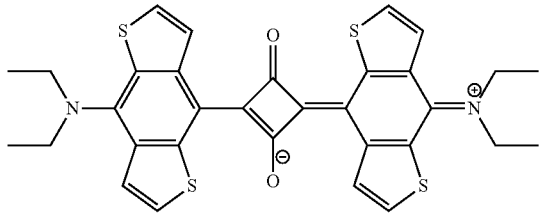

(Synthesis Method of Squarylium Compound (1))

The squarylium compound (1) can be synthesized using a well-known method of the related art. For example, the squarylium compound (1) can be synthesized using a method described in Chem. Eur. J., 2008, 14, 11082-11091, or a method described in paragraphs "0057" to "0062" of JP2009-15114A.

In addition, the squarylium compound (1) can be synthesized by synthesizing the following intermediate (A) using a cross-coupling method and causing the obtained intermediate (A) and the following compound (B) to react with each other. This synthesis method is preferable from the viewpoint of obtaining a desired compound with high yield.

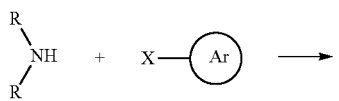

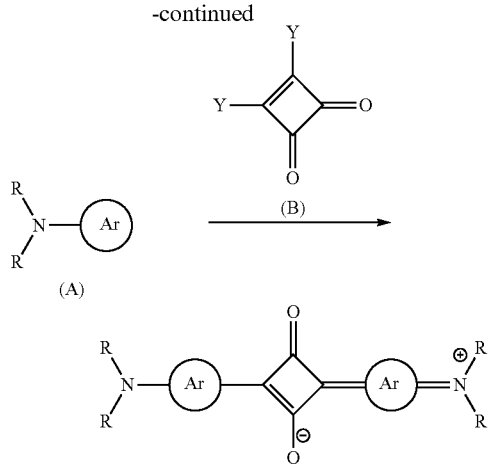

In the formula, Ar represents a divalent conjugated group which has a heteroaryl ring having a chalcogen atom. R's each independently represent a hydrogen atom or a substituent. X represents a halogen atom such as chlorine, bromine, or iodine, or a leaving group such as a trifluoromethanesulfonyloxy group or a nonafluorobutanesulfonyloxy group. Y's each independently represent OH, Cl, or OR', and R' represents an aryl group.

It is preferable that the intermediate (A) is synthesized with a cross-coupling method using a transition metal catalyst. Examples of the transition metal catalyst include a palladium catalyst, a copper catalyst, and a nickel catalyst.

<<Other Near Infrared Absorbing Compounds>>

The composition according to the present invention may further include near infrared absorbing compounds (hereinafter, also referred to as "other near infrared absorbing compounds") other than the squarylium compound (1). As the other near infrared absorbing compounds, a compound having an absorption maximum in a range of 700 to 1200 nm is preferable, and a compound having an absorption maximum in a range of 700 to 1000 nm is more preferable.

Examples of the other near infrared absorbing compounds include a phthalocyanine compound, a naphthalocyanine compound, a perylene compound, a pyrrolopyrrole compound, a cyanine compound, a dithiol metal complex compound, a naphthoquinone compound, an iminium compound, and an azo compound. Examples of the pyrrolopyrrole compound include a compound described in paragraphs "0016" to "0058" of JP2009-263614A. In addition, a squarylium compound other than the squarylium compound (1) may also be used. As the phthalocyanine compound, the naphthalocyanine compound, the iminium compound, the cyanine compound, the squarylium compound, or the croconium compound, for example, one of compounds described in paragraphs "0010" to "0081" of JP2010-111750A may be used, the content of which are incorporated in this specification. In addition the cyanine compound can be found in, for example, "Functional Colorants by Makoto Okawara, Masaru Matsuoka, Teijiro Kitao, and Tsuneoka Hirashima, published by Kodansha Scientific Ltd.", the content of which is incorporated herein by reference.

In a case where the composition according to the present invention includes the other near infrared absorbing compounds, the content of the other near infrared absorbing compound is preferably 0.1 to 70 mass % with respect to the total solid content of the composition according to the present invention. The lower limit is preferably 0.5 mass % or higher and more preferably 1.0 mass % or higher. The upper limit is preferably 60 mass % or lower, and more preferably 50 mass % or lower. In a case where the composition according to the present invention includes two or more other near infrared absorbing compound, it is preferable that the total content of the two or more near infrared absorbing compounds is in the above-described range.

In addition, the composition according to the present invention may include substantially no other near infrared absorbing compounds. The composition according to the present invention including substantially no other near infrared absorbing compounds denotes that, for example, the content of the other near infrared absorbing compounds is preferably 0.05 mass % or lower, more preferably 0.01 mass % or lower, and still more preferably 0 mass % with respect to the total solid content of the composition according to the present invention.

<<Chromatic Colorant>>

The composition according to the present invention may include a chromatic colorant. In the present invention, "chromatic colorant" denotes a colorant other than a white colorant and a black colorant. It is preferable that the chromatic colorant is a colorant having an absorption maximum in a wavelength range of 400 to 650 nm.

In the present invention, the chromatic colorant may be a pigment or a dye. It is preferable that the chromatic colorant is a pigment.

The pigment is preferably an organic pigment, and examples thereof are as follows. However, the present invention is not limited to the examples:

Color Index (C.I.) Pigment Yellow 1, 2, 3, 4, 5, 6, 10, 11, 12, 13, 14, 15, 16, 17, 18, 20, 24, 31, 32, 34, 35, 35:1, 36, 36:1, 37, 37:1, 40, 42, 43, 53, 55, 60, 61, 62, 63, 65, 73, 74, 77, 81, 83, 86, 93, 94, 95, 97, 98, 100, 101, 104, 106, 108, 109, 110, 113, 114, 115, 116, 117, 118, 119, 120, 123, 125, 126, 127, 128, 129, 137, 138, 139, 147, 148, 150, 151, 152, 153, 154, 155, 156, 161, 162, 164, 166, 167, 168, 169, 170, 171, 172, 173, 174, 175, 176, 177, 179, 180, 181, 182, 185, 187, 188, 193, 194, 199, 213, and 214 (all of which are yellow pigments);

C.I. Pigment Orange 2, 5, 13, 16, 17:1, 31, 34, 36, 38, 43, 46, 48, 49, 51, 52, 55, 59, 60, 61, 62, 64, 71, and 73 (all of which are orange pigments);

C.I. Pigment Red 1, 2, 3, 4, 5, 6, 7, 9, 10, 14, 17, 22, 23, 31, 38, 41, 48:1, 48:2, 48:3, 48:4, 49, 49:1, 49:2, 52:1, 52:2, 53:1, 57:1, 60:1, 63:1, 66, 67, 81:1, 81:2, 81:3, 83, 88, 90, 105, 112, 119, 122, 123, 144, 146, 149, 150, 155, 166, 168, 169, 170, 171, 172, 175, 176, 177, 178, 179, 184, 185, 187, 188, 190, 200, 202, 206, 207, 208, 209, 210, 216, 220, 224, 226, 242, 246, 254, 255, 264, 270, 272, and 279 (all of which are red pigments);

C.I. Pigment Green 7, 10, 36, 37, 58, and 59 (all of which are green pigments);

C.I. Pigment Violet 1, 19, 23, 27, 32, 37, and 42 (all of which are violet pigments); and C.I. Pigment Blue 1, 2, 15, 15:1, 15:2, 15:3, 15:4, 15:6, 16, 22, 60, 64, 66, 79, and 80 (all of which are blue pigments).

Among these organic pigments, one kind may be used alone, or two or more kinds may be used in combination.

As the dye, well-known dyes can be used without any particular limitation. In terms of a chemical structure, a dye such as a pyrazole azo dye, an anilino azo dye, a triphenylmethane dye, an anthraquinone dye, an anthrapyridone dye, a benzylidene dye, an oxonol dye, a pyrazolotriazole azo dye, a pyridone azo dye, a cyanine dye, a phenothiazine dye, a pyrrolopyrazole azomethine dye, a xanthene dye, a phthalocyanine dye, a benzopyran dye, an indigo dye, or a pyrromethene dye can be used. In addition, a polymer of the above-described dyes may be used. In addition, dyes described in JP2015-028144A and JP2015-34966A can also be used.

In addition, as the dye, an acid dye and/or a derivative thereof may be suitably used.

Furthermore, for example, a direct dye, a basic dye, a mordant dye, an acid mordant dye, an azoic dye, a dispersed dye, an oil-soluble dye, a food dye, and/or a derivative thereof can be suitably used.

Specific examples of the acid dye are shown below, but the present invention is not limited to these examples. For example, the following dyes and derivatives thereof can be used:

acid alizarin violet N;
acid blue 1, 7, 9, 15, 18, 23, 25, 27, 29, 40 to 45, 62, 70, 74, 80, 83, 86, 87, 90, 92, 103, 112, 113, 120, 129, 138, 147, 158, 171, 182, 192, 243, and 324:1;
acid chrome violet K;
acid Fuchsin and acid green 1, 3, 5, 9, 16, 25, 27, and 50;
acid orange 6, 7, 8, 10, 12, 50, 51, 52, 56, 63, 74, and 95;

acid red 1, 4, 8, 14, 17, 18, 26, 27, 29, 31, 34, 35, 37, 42, 44, 50, 51, 52, 57, 66, 73, 80, 87, 88, 91, 92, 94, 97, 103, 111, 114, 129, 133, 134, 138, 143, 145, 150, 151, 158, 176, 183, 198, 211, 215, 216, 217, 249, 252, 257, 260, 266, and 274;

acid violet 6B, 7, 9, 17, and 19;

acid yellow 1, 3, 7, 9, 11, 17, 23, 25, 29, 34, 36, 42, 54, 72, 73, 76, 79, 98, 99, 111, 112, 114, 116, 184, and 243; and Food Yellow 3.

In addition to the above-described examples, an azo acid dye, a xanthene acid dye, and a phthalocyanine acid dye are preferably used, and acid dyes, such as C.I. Solvent Blue 44 and 38, C.I. Solvent Orange 45, Rhodamine B, and Rhodamine 110 and derivatives of the dyes are also preferably used.

Among these, it is preferable that the dye is a colorant selected from the group consisting of a triarylmethane dye, an anthraquinone dye, an azomethine dye, a benzylidene dye, an oxonol dye, a cyanine dye, a phenothiazine dye, a pyrrolopyrazole azo methine dye, a xanthene dye, a phthalocyanine dye, a benzopyran dye, an indigo dye, a pyrazole azo dye, an anilino azo dye, a pyrazolotriazole azo dye, a pyridone azo dye, an anthrapyridone dye, and a pyrromethene dye.

Further, a combination of a pigment and a dye may be used.

In a case where the composition according to the present invention includes a chromatic colorant, the content of the chromatic colorant is preferably 0.1 to 70 mass % with respect to the total solid content of the composition according to the present invention. The lower limit is preferably 0.5 mass % or higher and more preferably 1.0 mass % or higher. The upper limit is preferably 60 mass % or lower, and more preferably 50 mass % or lower.

The content of the chromatic colorant is preferably 10 to 1000 parts by mass and more preferably 50 to 800 parts by mass with respect to 100 parts by mass of the squarylium compound (1).

In addition, the total content of the chromatic colorant, the squarylium compound (1), and the other near infrared absorbing compounds is preferably 1 to 80 mass % with respect to the total solid content of the composition according to the present invention. The lower limit is preferably 5 mass % or higher and more preferably 10 mass % or higher. The upper limit is preferably 70 mass % or lower, and more preferably 60 mass % or lower.

In a case where the composition according to the present invention includes two or more chromatic colorants, it is preferable that the total content of the two or more chromatic colorants is in the above-described range.

<<Coloring Material that Allows Transmission of at Least Part of Light in Infrared Range and Shields Light in Visible Range (Coloring Material that Shields Visible Light)>>

The composition according to the present invention may include a coloring material that shields visible light. The content of a pigment in the coloring material that shields visible light is preferably 90 mass % or higher, more preferably 95 mass % or higher, and still more preferably 99 mass % or higher with respect to the total mass of coloring material that shields visible light. In addition, it is preferable that black, gray, or a color similar to black or gray is exhibited using a combination of a plurality of coloring materials that shields visible light. In addition, it is preferable that the coloring material that shields visible light is a material that absorbs light in a wavelength range of violet to red. In addition, it is preferable that the coloring material that shields visible light is a material that shields light in a wavelength range of 450 to 650 nm.

In the present invention, it is preferable that the coloring material that shields visible light satisfies at least one of the following requirement (1) or (2), and it is more preferable that the coloring material that shields visible light satisfies the requirement (1).

(1): An aspect in which the coloring material that shields visible light includes two or more chromatic colorants (2): An aspect in which the coloring material that shields visible light includes an organic black colorant In addition, in the present invention, the organic black colorant as the coloring material that shields visible light denotes a material that absorbs light in a visible range and allows transmission of at least a part of light in an infrared range. Accordingly, in the present invention, the organic black colorant as the coloring material that shields visible light does not denote a black colorant that absorbs both light in an infrared range and light in a visible range, for example, carbon black or titanium black.

Examples of the chromatic colorant are as described above. Examples of the organic black colorant include a bisbenzofuranone compound, an azomethine compound, a perylene compound, and an azo compound. Among these, a bisbenzofuranone compound or a perylene compound is preferable. Examples of the bisbenzofuranone compound include compounds described in JP2010-534726A, JP2012-515233A, and JP2012-515234A. For example, "Irgaphor Black" (manufactured by BASF SE) is available. Examples of the perylene compound include C.I. Pigment Black 31 and 32. Examples of the azomethine compound include compounds described in JP1989-170601A (JP-H1-170601A) and JP1990-34664A (JP-H2-34664A). For example, "CHROMOFINE BLACK A1103" (manufactured by Dainichiseika Color & Chemicals Mfg. Co., Ltd.) is available.

In the present invention, it is preferable that the coloring material that shields visible light is a material in which a ratio A/B of a minimum value A of an absorbance in a wavelength range of 450 to 650 nm to a minimum value B of an absorbance in a wavelength range of 900 to 1300 nm is 4.5 or higher.

The above-described characteristics may be satisfied using one material alone or using a combination of a plurality of materials. For example, in the aspect (1), it is preferable that the spectral characteristics are satisfied using a combination of a plurality of chromatic colorants.

In a case where the coloring material that shields visible light includes two or more chromatic colorants, it is preferable that the chromatic colorants are selected from the group consisting of a red colorant, a green colorant, a blue colorant, a yellow colorant, a violet colorant, and an orange colorant.

In a case where the coloring material that shields visible light is formed using a combination of two or more chromatic colorants, examples of the combination of chromatic colorants are as follows.

(1) An aspect in which the coloring material that shields visible light includes a yellow colorant, a blue colorant, a violet colorant, and a red colorant (2) An aspect in which the coloring material that shields visible light includes a yellow colorant, a blue colorant, and a red colorant (3) An aspect in which the coloring material that shields visible light includes a yellow colorant, a violet colorant, and a red colorant (4) An aspect in which the coloring material that shields visible light includes a yellow colorant and a violet colorant (5) An aspect in which the coloring material that shields visible light includes a green colorant, a blue colorant, a violet colorant, and a red colorant (6) An aspect in which the coloring material that shields visible light includes a violet colorant and an orange colorant (7) An aspect in which the coloring material that shields visible light includes a green colorant, a violet colorant, and a red colorant (8) An aspect in which the coloring material that shields visible light includes a green colorant and a red colorant Specific examples of the aspect (1) include C.I. Pigment Yellow 139 or 185 as a yellow pigment, C.I. Pigment Blue 15:6 as a blue pigment, C.I. Pigment Violet 23 as a violet pigment, and C.I. Pigment Red 254 or 224 as a red pigment.

Specific examples of the aspect (2) include C.I. Pigment Yellow 139 or 185 as a yellow pigment, C.I. Pigment Blue 15:6 as a blue pigment, and C.I. Pigment Red 254 or 224 as a red pigment.

Specific examples of the aspect (3) include C.I. Pigment Yellow 139 or 185 as a yellow pigment, C.I. Pigment Violet 23 as a violet pigment, and C.I. Pigment Red 254 or 224 as a red pigment.

Specific examples of the aspect (4) include C.I. Pigment Yellow 139 or 185 as a yellow pigment, and C.I. Pigment Violet 23 as a violet pigment.

Specific examples of the aspect (5) include C.I. Pigment Green 7 or 36 as a green pigment, C.I. Pigment Blue 15:6 as a blue pigment, C.I. Pigment Violet 23 as a violet pigment, and C.I. Pigment Red 254 or 224 as a red pigment.

Specific examples of the aspect (6) include C.I. Pigment Violet 23 as a violet pigment, and C.I. Pigment Orange 71 as an orange pigment.

Specific examples of the aspect (7) include C.I. Pigment Green 7 or 36 as a green pigment, C.I. Pigment Violet 23 as a violet pigment, and C.I. Pigment Red 254 or 224 as a red pigment.

Specific examples of the aspect (8) include C.I. Pigment Green 7 or 36 as a green pigment, and C.I. Pigment Red 254 or 224 as a red pigment.

For example, ratios (mass ratios) between the respective colorants are as follows.

TABLE 1

| No. | Yellow Colorant | Green Colorant | Blue Colorant | Violet Colorant | Red Colorant | Orange Colorant |
|---|---|---|---|---|---|---|
| 1 | 0.1 to 0.4 | | 0.1 to 0.6 | 0.01 to 0.3 | 0.1 to 0.6 | |
| 2 | 0.1 to 0.4 | | 0.1 to 0.6 | | 0.2 to 0.7 | |
| 3 | 0.1 to 0.6 | | | 0.1 to 0.6 | 0.1 to 0.6 | |
| 4 | 0.2 to 0.8 | | | 0.2 to 0.8 | | |
| 5 | | 0.1 to 0.4 | 0.1 to 0.4 | 0.1 to 0.4 | 0.1 to 0.4 | |
| 6 | | | | 0.2 to 0.6 | | 0.4 to 0.8 |
| 7 | | 0.1 to 0.5 | | 0.2 to 0.7 | 0.1 to 0.4 | |
| 8 | | 0.5 to 0.8 | | | 0.2 to 0.5 | |

In a case where the composition according to the present invention includes the coloring material that shields visible light, the content of the coloring material that shields visible light is preferably 30 mass % or lower, more preferably 20 mass % or lower, and still more preferably 15 mass % or lower with respect to the total solid content of the composition. The lower limit is, for example, 0.01 mass % or higher or 0.5 mass % or higher.

In addition, the composition according to the present invention may not substantially include the coloring material that shields visible light. The composition substantially not including the coloring material that shields visible light represents that the content of the coloring material that shields visible light is preferably 0.005 mass % or lower, more preferably 0.001 mass % or lower, and still more preferably 0% with respect to the total solid content of the composition according to the present invention.

<<Pigment Derivative>>

The composition according to the present invention may include a pigment derivative. Examples of the pigment derivative include a compound having a structure in which a portion of a pigment is substituted with an acidic group, or a basic group. It is preferable that the pigment derivative has an acidic group or a basic group from the viewpoints of dispersibility and dispersion stability.

<<Resin>>

The composition according to the present invention includes a resin. The weight-average molecular weight (Mw) of the resin is preferably 2000 to 2000000. The upper limit is preferably 1000000 or lower and more preferably 500000 or lower. The lower limit is preferably 3000 or higher and more preferably 5000 or higher.

In addition, in a case where the resin is an epoxy resin, the weight-average molecular weight (Mw) of the epoxy resin is preferably 100 or higher and more preferably 200 to 2000000. The upper limit is preferably 1000000 or lower and more preferably 500000 or lower. The lower limit is preferably 100 or higher and more preferably 200 or higher.

Examples of the resin include a (meth)acrylic resin, an epoxy resin, an enethiol resin, a polycarbonate resin, a polyether resin, a polyarylate resin, a polysulfone resin, a polyethersulfone resin, a polyparaphenylene resin, a polyarylene ether phosphine oxide resin, a polyimide resin, a polyamide imide resin, a polyolefin resin, a cyclic olefin resin, and a polyester resin. Among these resins, one kind may be used alone, or two or more kinds may be used in combination.

Among these, from the viewpoint of solubility of the squarylium compound (1) in the resin and visible transparency, a (meth)acrylic resin, a polyester resin, or an epoxy resin is preferable, and a (meth)acrylic resin is more preferable.

Examples of the (meth)acrylic resin include a polymer including a constitutional unit derived from (meth)acrylic acid and/or an ester thereof. Specific examples of the (meth)acrylic resin include a polymer obtained by polymerization of at least one selected from the group consisting of (meth)acrylic acid, a (meth)acrylic acid ester, a (meth)acrylamide, and a (meth)acrylonitrile.

Examples of the polyester resin include: a polymer obtained by a reaction of a polyol (for example, ethylene glycol, propylene glycol, glycerin, or trimethylolpropane) and a polybasic acid (for example, an aromatic dicarboxylic acid such as terephthalic acid, isophthalic acid, or naphthalenedicarboxylic acid, an aromatic dicarboxylic acid in which an aromatic hydrogen atom of the above-described aromatic dicarboxylic acid is substituted with a methyl group, an ethyl group, a phenyl group, or the like, an aliphatic dicarboxylic acid having 2 to 20 carbon atoms such as adipic acid, sebacic acid, or dodecanedicarboxylic acid, or an alicyclic dicarboxylic acid such as cyclohexanedicarboxylic acid); and a polymer (for example, polycaprolactone) obtained by ring-opening polymerization of a cyclic ester compound such as a caprolactone monomer.

Examples of the epoxy resin include a bisphenol A epoxy resin, a bisphenol F epoxy resin, a phenol novolac epoxy resin, a cresol novolac epoxy resin, and an aliphatic epoxy resin.

Examples of the bisphenol A epoxy resin include JER827, JER828, JER834, JER1001, JER1002, JER1003, JER1055, JER1007, JER1009, and JER1010 (all of which are manufactured by Mitsubishi Chemical Corporation) and EPICLON860, EPICLON1050, EPICLON1051, and EPICLON1055 (all of which are manufactured by DIC Corporation).

Examples of the bisphenol F epoxy resin include JER806, JER807, JER4004, JER4005, JER4007, and JER4010 (all of which are manufactured by Mitsubishi Chemical Corporation), EPICLON830 and EPICLON835 (all of which are manufactured by DIC Corporation), and LCE-21 and RE-602S (all of which are manufactured by Nippon Kayaku Co., Ltd.).

Examples of the phenol novolac epoxy resin include JER152, JER154, JER157S70, and JER157S65 (all of which are manufactured by Mitsubishi Chemical Corporation) and EPICLON N-740, EPICLON N-770, and EPICLON N-775 (all of which are manufactured by DIC Corporation).

Examples of the cresol novolac epoxy resin include EPICLON N-660, EPICLON N-665, EPICLON N-670, EPICLON N-673, EPICLON N-680, EPICLON N-690, and EPICLON N-695 (all of which are manufactured by DIC Corporation) and EOCN-1020 (manufactured by Nippon Kayaku Co., Ltd.).

Examples of the aliphatic epoxy resin include ADEKA RESIN EP-4080S, ADEKA RESIN EP-4085S, and ADEKA RESIN EP-4088S (all of which are manufactured by Adeka Corporation), CELLOXIDE 2021P, CELLOXIDE 2081, CELLOXIDE 2083, CELLOXIDE 2085, EHPE3150, EPOLEAD PB 3600, and EPOLEAD PB 4700 (all of which are manufactured by Daicel Corporation), and DENACOL EX-212L, DENACOL EX-214L, DENACOL EX-216L, DENACOL EX-321L, and DENACOL EX-850L (all of which are manufactured by Nagase ChemteX Corporation).

Other examples of the commercially available product include ADEKA RESIN EP-4000S, ADEKA RESIN EP-4003S, ADEKA RESIN EP-4010S, and ADEKA RESIN EP-4011S (all of which are manufactured by Adeka Corporation), NC-2000, NC-3000, NC-7300, XD-1000, EPPN-501, and EPPN-502 (all of which are manufactured by Adeka Corporation), JER1031S (manufactured by Mitsubishi Chemical Corporation), and RIPOXY SPCF-9X (manufactured by Showa Denko K.K.).

In addition, the resin may have an acid group. Examples of the acid group include a carboxyl group, a phosphate group, a sulfonate group, and a phenolic hydroxyl group. Among these acid groups, one kind may be used alone, or two or more kinds may be used in combination.

As the resin having an acid group, a polymer having a carboxyl group at a side chain thereof is preferable, and examples thereof include: an alkali-soluble phenol resin such as a methacrylic acid copolymer, an acrylic acid copolymer, an itaconic acid copolymer, a crotonic acid copolymer, a maleic acid copolymer, a partially esterified maleic acid copolymer, or a novolac type resin; an acidic cellulose derivative having a carboxyl group at a side chain thereof; and a resin obtained by adding an acid anhydride to a polymer having a hydroxyl group. In particular, a copolymer of (meth)acrylic acid and another monomer which is copolymerizable with the (meth)acrylic acid is preferable. Examples of the monomer which is copolymerizable with the (meth)acrylic acid include an alkyl (meth)acrylate, an aryl (meth)acrylate, and a vinyl compound. Examples of the alkyl (meth)acrylate and the aryl (meth)acrylate include methyl (meth)acrylate, ethyl (meth)acrylate, propyl (meth)acrylate, butyl (meth)acrylate, isobutyl (meth)acrylate, pentyl (meth)acrylate, hexyl (meth)acrylate, octyl (meth)acrylate, phenyl (meth)acrylate, benzyl (meth)acrylate, tolyl (meth)acrylate, naphthyl (meth)acrylate, and cyclohexyl (meth)acrylate. Examples of the vinyl compound include styrene, α-methylstyrene, vinyl toluene, glycidyl methacrylate, acrylonitrile, vinyl acetate, N-vinylpyrrolidone, tetrahydrofurfuryl methacrylate, a polystyrene macromonomer, and a polymethyl methacrylate macromonomer. Examples of the N-position-substituted maleimide monomer copolymer described in JP1998-300922A (JP-H10-300922A) include N-phenylmaleimide and N-cyclohexylmaleimide. Among these monomers which are copolymerizable with the (meth)acrylic acid, one kind may be used alone, or two or more kinds may be used in combination.

As the resin having an acid group, a copolymer including benzyl (meth)acrylate and (meth)acrylic acid; a copolymer including benzyl (meth)acrylate, (meth)acrylic acid, and 2-hydroxyethyl (meth)acrylate; or a multi-component copolymer including benzyl (meth)acrylate, (meth)acrylic acid, and another monomer can be preferably used. In addition, copolymers described in JP1995-140654A (JP-H7-140654A) obtained by copolymerization of 2-hydroxyethyl (meth)acrylate can be preferably used, and examples thereof include: a copolymer including 2-hydroxypropyl (meth)acrylate, a polystyrene macromonomer, benzyl methacrylate, and methacrylic acid; a copolymer including 2-hydroxy-3-phenoxypropyl acrylate, a polymethyl methacrylate macromonomer, benzyl methacrylate, and methacrylic acid; a copolymer including 2-hydroxyethyl methacrylate, a polystyrene macromonomer, methyl methacrylate, and methacrylic acid; or a copolymer including 2-hydroxyethyl methacrylate, a polystyrene macromonomer, benzyl methacrylate, and methacrylic acid.

As the resin having an acid group, a polymer obtained by copolymerization of monomer components including a compound represented by the following Formula (ED1) and/or a compound represented by the following Formula (ED2) (hereinafter, these compounds will also be referred to as "ether dimer") is also preferable.

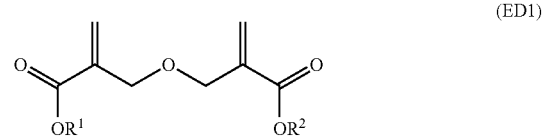

(ED1)

In Formula (ED1), $R^1$ and $R^2$ each independently represent a hydrogen atom or a hydrocarbon group having 1 to 25 carbon atoms which may have a substituent.

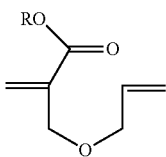

(ED2)

In Formula (ED2), R represents a hydrogen atom or an organic group having 1 to 30 carbon atoms. Specific examples of Formula (ED2) can be found in the description of JP2010-168539A.

The hydrocarbon group having 1 to 25 carbon atoms represented by $R^1$ and $R^2$ in Formula (ED1) which may have a substituent is not particularly limited, and examples thereof include a linear or branched alkyl group such as methyl, ethyl, n-propyl, isopropyl, n-butyl, isobutyl, tert-butyl, tert-amyl, stearyl, lauryl, or 2-ethylhexyl; an aryl group such as phenyl; an alicyclic group such as cyclohexyl, tert-butylcyclohexyl, dicyclopentadienyl, tricyclodecanyl, isobornyl, adamantyl, or 2-methyl-2-adamantyl; an alkyl group substituted with alkoxy such as 1-methoxyethyl or 1-ethoxyethyl; and an alkyl group substituted with an aryl group such as benzyl. Among these, a primary or secondary carbon substituent which is not likely to leave due to an acid or heat, for example, methyl, ethyl, cyclohexyl, or benzyl is preferable from the viewpoint of heat resistance.

Specific examples of the ether dimer can be found in paragraph "0317" of JP2013-29760A, the content of which is incorporated herein by reference. Among these ether dimers, one kind may be used alone, or two or more kinds may be used in combination. A structure derived from the compound represented by Formula (ED) may be copolymerized with other monomers.

The resin having an acid group may include a structural unit which is derived from a compound represented by the following Formula (X).

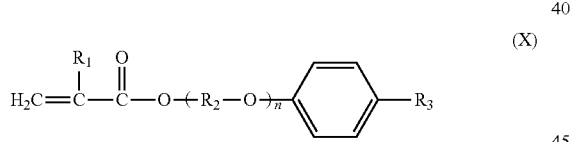

(X)

In Formula (X), $R_1$ represents a hydrogen atom or a methyl group, $R_2$ represents an alkylene group having 2 to 10 carbon atoms, and $R_3$ represents a hydrogen atom or an alkyl group having 1 to 20 carbon atoms which may have a benzene ring. n represents an integer of 1 to 15.

In Formula (X), the number of carbon atoms in the alkylene group of $R_2$ is preferably 2 to 3. In addition, the number of carbon atoms in the alkyl group of $R_3$ is preferably 1 to 20 and more preferably 1 to 10, and the alkyl group of $R_3$ may have a benzene ring. Examples of the alkyl group having a benzene ring represented by $R_3$ include a benzyl group and a 2-phenyl(iso)propyl group.

The details of the resin having an acid group can be found in paragraphs "0558" to "0571" of JP2012-208494A (corresponding to paragraphs "0685" to "0700" of US2012/0235099A) and paragraphs "0076" to "0099" of JP2012-198408A, the contents of which are incorporated herein by reference.

The acid value of the resin having an acid group is preferably 30 to 200 mgKOH/g. The lower limit is preferably 50 mgKOH/g or higher and more preferably 70 mgKOH/g or higher. The upper limit is preferably 150 mgKOH/g or lower and more preferably 120 mgKOH/g or lower.

The resin may have a crosslinking group. In the present invention, the crosslinking group refers to a group which reacts due to the action of heat, light or a radical to form a chemical bond. Specific examples of the crosslinking group include a group having an ethylenically unsaturated bond, a cyclic ether group, a methylol group, an alkoxysilyl group, and a chlorosilyl group. Examples of the resin having a crosslinking group include a resin including a constitutional unit having a crosslinking group and the above-described epoxy resin. Examples of the constitutional unit having a crosslinking group include the following (A2-1) to (A2-4).

(A2-1)

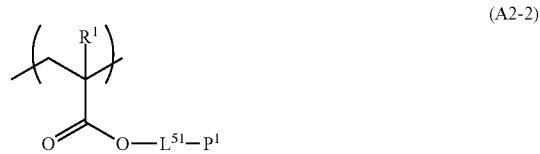

(A2-2)

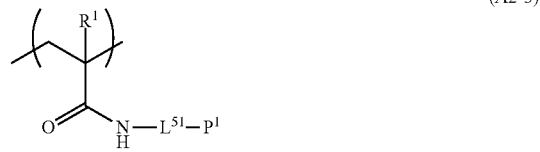

(A2-3)

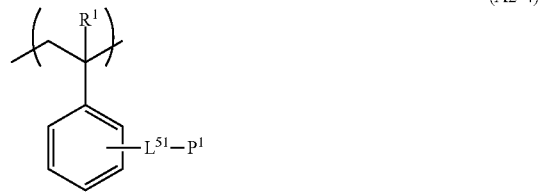

(A2-4)

$R^1$ represents a hydrogen atom or an alkyl group. The number of carbon atoms in the alkyl group is preferably 1 to 5, more preferably 1 to 3, and still more preferably 1. It is preferable that $R^1$ represents a hydrogen atom or a methyl group.

$L^{51}$ represents a single bond or a divalent linking group. Examples of the divalent linking group include an alkylene group, an arylene group, —O—, —S—, —CO—, —COO—, —OCO—, —SO$_2$—, —NR$^{10}$— ($R^{10}$ represents a hydrogen atom or an alkyl group and preferably a hydrogen atom), and a group including a combination thereof. Among these, a group including a combination —O— and at least one of an alkylene group, an arylene group, or an alkylene group is preferable. The number of carbon atoms in the alkylene group is preferably 1 to 30, more preferably 1 to 15, and still more preferably 1 to 10. The alkylene group may have a substituent but is preferably unsubstituted. The alkylene group may be linear, branched, or cyclic. In addition, the cyclic alkylene group may be monocyclic or polycyclic. The number of carbon atoms in the arylene group is preferably 6 to 18, more preferably 6 to 14, and still more preferably 6 to 10.

P¹ represents a crosslinking group. Examples of the crosslinking group include a group having an ethylenically unsaturated bond, a cyclic ether group, a methylol group, an alkoxysilyl group, and a chlorosilyl group. Among these, a group having an ethylenically unsaturated bond, a cyclic ether group, an alkoxysilyl group, or a chlorosilyl group is preferable. Examples of the group having an ethylenically unsaturated bond include a vinyl group, a (meth)allyl group, a (meth)acryloyl group, and a (meth)acryloyloxy group.

Examples of the cyclic ether group include an epoxy group (an oxiranyl group) and an oxetanyl group. Examples of the alkoxysilyl group include a monoalkoxysilyl group, a dialkoxysilyl group, and a trialkoxysilyl group. As the group having an ethylenically unsaturated bond, a (meth)acryloyl group or a (meth)acryloyloxy group is preferable. As the cyclic ether group, an epoxy group is preferable. As the alkoxysilyl group, a dialkoxysilyl group or a trialkoxysilyl group is preferable. In addition, the number of carbon atoms in the alkoxy group of the alkoxysilyl group is preferably 1 to 5, more preferably 1 to 3, and still more preferably 1 or 2. Examples of the chlorosilyl group include a monochlorosilyl group, a dichlorosilyl group, and a trichlorosilyl group. Among these, a dichlorosilyl group or a trichlorosilyl group is preferable, and a trichlorosilyl group is more preferable.

Examples of the resin having a crosslinking group include DIANAL NR series (manufactured by Mitsubishi Rayon Co., Ltd.), PHOTOMER 6173 (a COOH-containing polyurethane acrylic oligomer; manufactured by Diamond Shamrock Co., Ltd.), BISCOAT R-264 and KS Resist 106 (both of which are manufactured by Osaka Organic Chemical Industry Ltd.), CYCLOMER-P series (for example, ACA230AA) and PLAKCEL CF200 series (both of which manufactured by Daicel Corporation), EBECRYL 3800 (manufactured by Daicel-UCB Co., Ltd.), and ACRYCURE RD-F8 (manufactured by Nippon Shokubai Co., Ltd.). In addition, for example, the above-described epoxy resin can also be used.

It is also preferable that the resin has a constitutional unit represented by any one of Formulae (A3-1) to (A3-7).

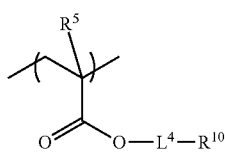

(A3-1)

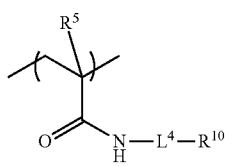

(A3-2)

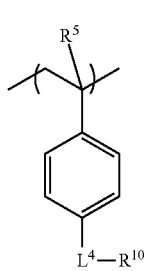

(A3-3)

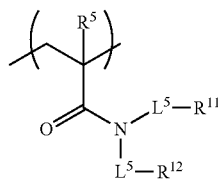

(A3-4)

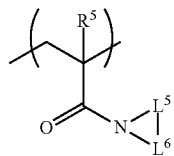

(A3-5)

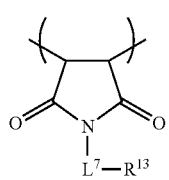

(A3-6)

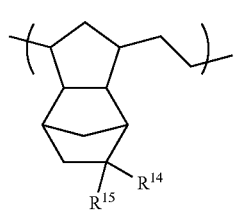

(A3-7)

In the formulae, $R^5$ represents a hydrogen atom or an alkyl group, $L^4$ to $L^7$ each independently represent a single bond or a divalent linking group, and $R^{10}$ to $R^{13}$ each independently represent an alkyl group or an aryl group. $R^{14}$ and $R^{15}$ each independently represent a hydrogen atom or a substituent.

$R^5$ has the same definition and the same preferable range as $R^1$ in Formulae (A2-1) to (A2-4).

$L^4$ to $L^7$ have the same definition and the same preferable range as $L^1$ in Formulae (A2-1) to (A2-4).

The alkyl group represented by $R^{10}$ may be linear, branched, or cyclic and is preferably cyclic. The alkyl group may have a substituent or may be unsubstituted. The number of carbon atoms in the alkyl group is preferably 1 to 30, more preferably 1 to 20, and still more preferably 1 to 10. The number of carbon atoms in the aryl group represented by $R^{10}$ is preferably 6 to 18, more preferably 6 to 12, and still more preferably 6. It is preferable that $R^{10}$ represents a cyclic alkyl group or an aryl group.

The alkyl group represented by $R^{11}$ and $R^{12}$ may be linear, branched, or cyclic and is preferably linear or branched. The alkyl group may have a substituent or may be unsubstituted. The number of carbon atoms in the alkyl group is preferably 1 to 12, more preferably 1 to 6, and still more preferably 1 to 4. The number of carbon atoms in the aryl group represented by $R^{11}$ and $R^{12}$ is preferably 6 to 18, more preferably 6 to 12, and still more preferably 6. It is preferable that $R^{11}$ and $R^{12}$ represent a linear or branched alkyl group.

The alkyl group represented by $R^{13}$ may be linear, branched, or cyclic and is preferably linear or branched. The alkyl group may have a substituent or may be unsubstituted. The number of carbon atoms in the alkyl group is preferably 1 to 12, more preferably 1 to 6, and still more preferably 1 to 4. The number of carbon atoms in the aryl group represented by $R^{13}$ is preferably 6 to 18, more preferably 6 to 12, and still more preferably 6. It is preferable that $R^{13}$ represents a linear or branched alkyl group or an aryl group.

Examples of the substituent represented by $R^{14}$ and $R^{15}$ include the groups described in the substituent group T. In particular, it is preferable that at least one of $R^{14}$ or $R^{15}$ represents a cyano group or —COOR$^a$. Ra represents a hydrogen atom or a substituent. Examples of the substituent represented by Ra include the groups described in the substituent group T. For example, an alkyl group or an aryl group is preferable.

The content of the resin is preferably 1 to 80 mass % with respect to the total solid content of the composition. The lower limit is preferably 5 mass % or higher and more preferably 7 mass % or higher. The upper limit is preferably 50 mass % or lower and more preferably 30 mass % or lower.

<<Compound Having Crosslinking Group (Crosslinking Compound)>>

The composition according to the present invention may include a compound having a crosslinking group (crosslinking compound). By the composition including the crosslinking compound, a film having excellent heat resistance and solvent resistance can be formed. As the crosslinking compound, a well-known compound which is crosslinkable by a radical, an acid, or heat can be used. Examples of the crosslinking compound include a compound which has a group having an ethylenically unsaturated bond, a compound having a cyclic ether group, a compound having a methylol group, a compound having an alkoxysilyl group, and a compound having a chlorosilyl group. The details of the group having an ethylenically unsaturated bond, the cyclic ether group, the alkoxysilyl group, and the chlorosilyl group can be found in the description of the groups regarding the resin.

The crosslinking compound may be in the form of a monomer or a polymer and is preferably a monomer. The molecular weight of the monomer type crosslinking compound is preferably 100 to 3000. The upper limit is preferably 2000 or lower and more preferably 1500 or lower. The lower limit is preferably 150 or higher and more preferably 250 or higher. In addition, it is preferable that the crosslinking compound is a compound substantially not having a molecular weight distribution. Here, the compound substantially not having a molecular weight distribution represent that the dispersity (weight-average molecular weight (Mw)/number-average molecular weight (Mn)) of the compound is preferably 1.0 to 1.5 and more preferably 1.0 to 1.3.

[Compound which has Group Having Ethylenically Unsaturated Bond]

In the present invention, as the crosslinking compound, a compound which has a group having an ethylenically unsaturated bond can be used. It is preferable that the compound which has a group having an ethylenically unsaturated bond is a monomer. The molecular weight of the compound which has a group having an ethylenically unsaturated bond is preferably 100 to 3000. The upper limit is preferably 2000 or lower and more preferably 1500 or lower. The lower limit is preferably 150 or higher and more preferably 250 or higher. The compound which has a group having an ethylenically unsaturated bond is preferably a (meth)acrylate compound having 3 to 15 functional groups and more preferably a (meth)acrylate compound having 3 to 6 functional groups.

Examples of the compound can be found in paragraphs "0033" and "0034" of JP2013-253224A, the content of which is incorporated herein by reference. As the compound, ethyleneoxy-modified pentaerythritol tetraacrylate (as a commercially available product, NK ESTER ATM-35E manufactured by Shin-Nakamura Chemical Co., Ltd.), dipentaerythritol triacrylate (as a commercially available product, KAYARAD D-330 manufactured by Nippon Kayaku Co., Ltd.), dipentaerythritol tetraacrylate (as a commercially available product, KAYARAD D-320 manufactured by Nippon Kayaku Co., Ltd.), dipentaerythritol penta(meth)acrylate (as a commercially available product, KAYARAD D-310 manufactured by Nippon Kayaku Co., Ltd.), dipentaerythritol hexa(meth)acrylate (as a commercially available product, KAYARAD DPHA manufactured by Nippon Kayaku Co., Ltd., A-DPH-12E, manufactured by Shin-Nakamura Chemical Co., Ltd.), or a structure in which the (meth)acryloyl group is bonded through an ethylene glycol or a propylene glycol residue is preferable. In addition, oligomers of the above-described examples can be used.

In addition, the compound having an ethylenically unsaturated bond can be found in the description of a polymerizable compound in paragraphs "0034" to "0038" of JP2013-253224A, the content of which is incorporated herein by reference. Examples of the compound having an ethylenically unsaturated bond include a polymerizable monomer in paragraph "0477" of JP2012-208494A (corresponding to paragraph "0585" of US2012/0235099A), the content of which is incorporated herein by reference.

In addition, diglycerin ethylene oxide (EO)-modified (meth)acrylate (as a commercially available product, M-460 manufactured by Toagosei Co., Ltd.) is preferable. Pentaerythritol tetraacrylate (A-TMMT manufactured by Shin-Nakamura Chemical Co., Ltd.) or 1,6-hexanediol diacrylate (KAYARAD HDDA manufactured by Nippon Kayaku Co., Ltd.) is also preferable. Oligomers of the above-described examples can be used. For examples, RP-1040 (manufactured by Nippon Kayaku Co., Ltd.) is used.

The compound which has a group having an ethylenically unsaturated bond may have an acid group such as a carboxyl group, a sulfo group, or a phosphate group. Examples of the compound having an acid group include an ester of an aliphatic polyhydroxy compound and an unsaturated carboxylic acid. A compound having an acid group obtained by causing a nonaromatic carboxylic anhydride to react with an unreacted hydroxyl group of an aliphatic polyhydroxy compound is preferable. In particular, it is more preferable that, in this ester, the aliphatic polyhydroxy compound is pentaerythritol and/or dipentaerythritol. Examples of a commercially available product of the monomer having an acid group include M-305, M-510, and M-520 of ARONIX series as polybasic acid-modified acrylic oligomer (manufactured by Toagosei Co., Ltd.). The acid value of the compound having an acid group is preferably 0.1 to 40 mgKOH/g. The lower limit is preferably 5 mgKOH/g or higher. The upper limit is preferably 30 mgKOH/g or lower.

In addition, a compound having a caprolactone structure is also preferable as the compound which has a group having an ethylenically unsaturated bond. The compound having a caprolactone structure is not particularly limited as long as it has a caprolactone structure in the molecule thereof, and examples thereof include ε-caprolactone-modified polyfunctional (meth)acrylate obtained by esterification of a polyhydric alcohol, (meth)acrylic acid, and ε-caprolactone, the polyhydric alcohol being, for example, trimethylolethane, ditrimethylolethane, trimethylolpropane, ditrimethylolpropane, pentaerythritol, dipentaerythritol, tripentaerythritol, glycerin, diglycerol, or trimethylolmelamine. Examples of the compound having a caprolactone structure can be found in paragraphs "0042" to "0045" of JP2013-253224A, the content of which is incorporated herein by reference. Examples of the compound having a caprolactone structure include: DPCA-20, DPCA-30, DPCA-60, and DPCA-120 which are commercially available as KAYARADDPCA series manufactured by Nippon Kayaku Co., Ltd.; SR-494 (manufactured by Sartomer) which is a tetrafunctional acrylate having four ethyleneoxy chains; and TPA-330 (manufactured by Nippon Kayaku Co., Ltd.) which is a trifunctional acrylate having three isobutyleneoxy chains.

As the compound which has a group having an ethylenically unsaturated bond, a urethane acrylate described in JP1973-41708B (JP-S48-41708B), JP1976-37193A (JP-S51-37193A), JP1990-32293B (JP-H2-32293B), or JP1990-16765B (JP-H2-16765B), or a urethane compound having a ethylene oxide skeleton described in JP1983-49860B (JP-S58-49860B), JP1981-17654B (JP-S56-17654B), JP1987-39417B (JP-S62-39417B), or JP1987-39418B (JP-S62-39418B) is also preferable. In addition, the compound which has a group having an ethylenically unsaturated bond can be obtained by using an addition-polymerizable compound having an amino structure or a sulfide structure in the molecules described in JP1988-277653A (JP-S63-277653A), JP1988-260909A (JP-S63-260909A), or JP1989-105238A (JP-H1-105238A).

Examples of a commercially available product of the compound include URETHANE OLIGOMER UAS-10 and UAB-140 (manufactured by Sanyo-Kokusaku Pulp Co., Ltd.), UA-7200 (manufactured by Shin-Nakamura Chemical Co., Ltd.), DPHA-40H (manufactured by Nippon Kayaku Co., Ltd.), and UA-306H, UA-306T, UA-306I, AH-600, T-600 and AI-600 (manufactured by Kyoeisha Chemical Co., Ltd.).

[Compound Having Cyclic Ether Group]

In the present invention, as the crosslinking compound, a compound having a cyclic ether group can also be used. Examples of the cyclic ether group include an epoxy group and an oxetanyl group. Among these, an epoxy group is preferable. Examples of the compound having a cyclic ether group include a monofunctional or polyfunctional glycidyl ether compound, and a polyfunctional aliphatic glycidyl ether compound. As the epoxy group such as glycidyl (meth)acrylate or allyl glycidyl ether, a compound having a glycidyl group or a compound having an alicyclic epoxy group can also be used. Examples of the compound having an epoxy group can be found in, for example, paragraph "0045" of JP2009-265518A, the content of which is incorporated herein by reference. In addition, for example, the epoxy resin described above regarding the resin can also be used. As the compound having a cyclic ether group, a commercially available product can also be used. Examples of a commercially available product of the compound having a cyclic ether group can be found in, for example, paragraph "0191" JP2012-155288A, the content of which is incorporated herein by reference.

[Compound Having Alkoxysilyl Group]

In the present invention, as the crosslinking compound, a compound having an alkoxysilyl group can also be used. The number of carbon atoms in the alkoxy group of the alkoxysilyl group is preferably 1 to 5, more preferably 1 to 3, and still more preferably 1 or 2. As the alkoxysilyl group, a dialkoxysilyl group or a trialkoxysilyl group is preferable. It is preferable that two or more alkoxysilyl groups are present in one molecule, and it is more preferable that two or three alkoxysilyl groups are present in one molecule. Specific examples of the compound having an alkoxysilyl group include methyl trimethoxysilane, dimethyl dimethoxysilane, phenyl trimethoxysilane, methyltriethoxysilane, and dimethyl diethoxysilane, phenyltriethoxysilane, n-propyltrimethoxysilane, n-propyltriethoxysilane, hexyl trimethoxysilane, hexyl triethoxysilane, octyl triethoxysilane, decyl trimethoxysilane, 1,6-bis(trimethoxysilyl)hexane, trifluoropropyltrimethoxysilane, hexamethyldisilazane, vinyl trimethoxysilane, vinyltriethoxysilane, 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, 3-triethoxysilyl-N-(1,3-dimethylbutylidene)propylamine, N-phenyl-3-aminopropyltrimethoxysilane, N-(vinylbenzyl)-2-aminoethyl-3-aminopropyltrimethoxysilane hydrochloride, tris-(trimethoxysilylpropyl)isocyanurate, 3-ureidopropyltriethoxysilane, 3-mercaptopropylmethyldimethoxysilane, 3-mercaptopropyltrimethoxysilane, and bis(triethoxysilylpropyl)tetrasulfide, and 3-isocyanatepropyltriethoxysilane. In addition to the above-described examples, an alkoxy oligomer can be used. In addition, the following compounds can also be used.

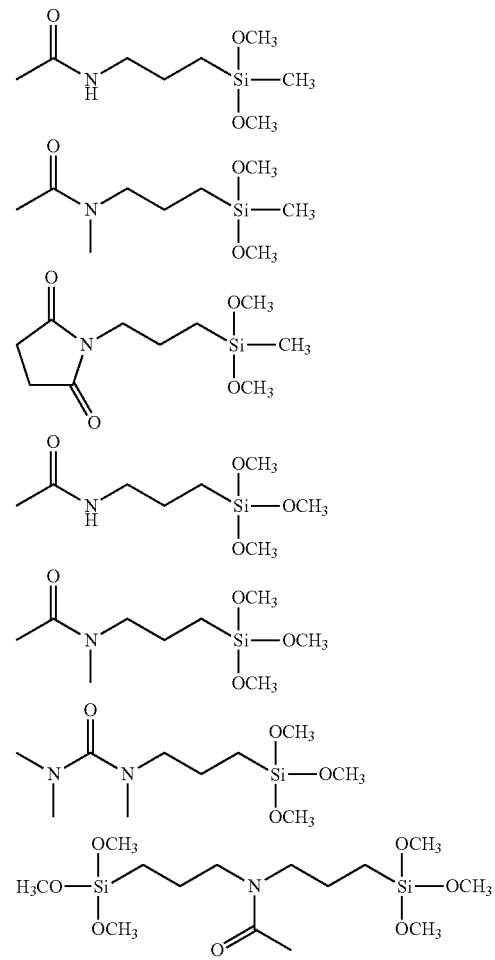

Examples of a commercially available product of the silane coupling agent include KBM-13, KBM-22, KBM-103, KBE-13, KBE-22, KBE-103, KBM-3033, KBE-3033, KBM-3063, KBM-3066, KBM-3086, KBE-3063, KBE-3083, KBM-3103, KBM-3066, KBM-7103, SZ-31, KPN-3504, KBM-1003, KBE-1003, KBM-303, KBM-402, KBM-403, KBE-402, KBE-403, KBM-1403, KBM-502, KBM-503, KBE-502, KBE-503, KBM-5103, KBM-602, KBM-603, KBM-903, KBE-903, KBE-9103, KBM-573, KBM-575, KBM-9659, KBE-585, KBM-802, KBM-803, KBE-846, KBE-9007, X-40-1053, X-41-1059A, X-41-1056, X-41-1805, X-41-1818, X-41-1810, X-40-2651, X-40-2655A, KR-513, KC-89S, KR-500, X-40-9225, X-40-9246, X-40-9250, KR-401N, X-40-9227, X-40-9247, KR-510, KR-9218, KR-213, X-40-2308, and X-40-9238 (all of which are manufactured by Shin-Etsu Chemical Co., Ltd.).

[Compound Having Chlorosilyl Group]

In the present invention, as the crosslinking compound, a compound having a chlorosilyl group can also be used. As the chlorosilyl group, a dichlorosilyl group or a trichlorosilyl group is preferable. It is preferable that two or more chlorosilyl groups are present in one molecule, and it is more preferable that two or three chlorosilyl groups are present in one molecule. Examples of the compound having a chlorosilyl group include methyltrichlorosilane, ethyltrichlorosilane, phenyltrichlorosilane, dichloro(methyl)phenylsilane, dimethyldichlorosilane, and diethyldichlorosilane.

The content of the crosslinking compound is preferably 1 to 90 mass % with respect to the total solid content of the composition. The lower limit is preferably 2 mass % or higher, more preferably 5 mass % or higher, and still more preferably 10 mass % or higher. The upper limit is preferably 80 mass % or lower, and more preferably 75 mass % or lower.

As the crosslinking compound, one kind may be used alone, or two or more kinds may be used. In a case where two or more antioxidants are used in combination, it is preferable that the total content of the two or more antioxidants is in the above-described range.

<<Photopolymerization Initiator>>

The composition according to the present invention may include a photopolymerization initiator. In particular, in case where the composition includes a radically polymerizable component such as a resin which includes a group having an ethylenically unsaturated bond or a crosslinking compound, it is preferable that the composition includes a photopolymerization initiator. The photopolymerization initiator is not particularly limited and can be appropriately selected from well-known photopolymerization initiators. For example, a photopolymerization initiator having photosensitivity to light in a range from the ultraviolet range to the visible range is preferable. it is preferable that the photopolymerization initiator is a photoradical polymerization initiator. In addition, it is preferable that the photopolymerization initiator is at least one compound having a molar absorption coefficient of at least 50 in a range of about 300 nm to 800 nm (preferably 330 nm to 500 nm).

Examples of the photopolymerization initiator include: a halogenated hydrocarbon derivative (having, for example, a triazine skeleton or an oxadiazole skeleton); an acylphosphine compound such as acylphosphine oxide; an oxime compound such as hexaarylbiimidazole or an oxime derivative; an organic peroxide, a thio compound, a ketone compound, an aromatic onium salt, keto oxime ether, an aminoacetophenone compound, and hydroxyacetophenone. Examples of the halogenated hydrocarbon compound having a triazine skeleton include a compound described in Bull. Chem. Soc. Japan, 42, 2924 (1969) by Wakabayshi et al., a compound described in Great Britain Patent No. 1388492, a compound described in JP1978-133428A (JP-S53-133428A), a compound described in Great German Patent No. 3337024, a compound described in J. Org. Chem.; 29, 1527 (1964) by F. C. Schaefer et al., a compound described in JP1987-58241A (JP-S62-58241A), a compound described in JP1993-281728A (JP-H5-281728A), a compound described in JP1993-34920A (JP-S5-34920A), and a compound described in U.S. Pat. No. 4,212,976A (for example, a compound having an oxadiazole skeleton).

In addition, from the viewpoint of exposure sensitivity, a compound selected from the group consisting of a trihalomethyltriazine compound, a benzyldimethylketanol compound, an $\alpha$-hydroxy ketone compound, an $\alpha$-amino ketone compound, an acylphosphine compound, a phosphine oxide compound, a metallocene compound, an oxime compound, a triarylimidazole dimer, an onium compound, a benzothiazole compound, a benzophenone compound, an acetophenone compound and a derivative thereof, a cyclopentadiene-benzene-iron complex and a salt thereof, and a halomethyl oxadiazole compound, a 3-aryl-substituted coumarin compound is preferable.

As the photopolymerization initiator, a hydroxyacetophenone compound, an aminoacetophenone compound, or an acylphosphine compound can also be preferably used. More specifically, for example, an aminoacetophenone initiator described in JP1998-291969A (JP-H10-291969A) or an acylphosphine initiator described in JP4225898B can also be used. As the hydroxyacetophenone initiator, for example, IRGACURE-184, DAROCUR-1173, IRGACURE-500, IRGACURE-2959, or IRGACURE-127 (trade name, all of which are manufactured by BASF SE) can be used. As the aminoacetophenone initiator, IRGACURE-907, IRGACURE-369, or IRGACURE-379EG (trade name, all of which are manufactured by BASF SE) which is a commercially available product can be used. As the aminoacetophenone initiator, a compound described in JP2009-191179A whose absorption wavelength is adjusted to match with that of a light source having a long wavelength of, for example, 365 nm or 405 nm can also be used.

As the acylphosphine initiator, IRGACURE-819, or DAROCUR-TPO (trade name, all of which are manufactured by BASF SE) which is a commercially available product can be used.

As the photopolymerization initiator, for example, an oxime compound is more preferable. Specific examples of the oxime compound include a compound described in JP2001-233842A, a compound described in JP2000-80068A, and a compound described in JP2006-342166A.

Examples of the oxime compound which can be preferably used include 3-benzoyloxyiminobutane-2-one, 3-acetoxyiminobutane-2-one, 3-propionyloxyiminobutane-2-one, 2-acetoxyiminopentane-3-one, 2-acetoxyimino-1-phenylpropane-1-one, 2-benzoyloxyimino-1-phenylpropane-1-one, 3-(4-toluene sulfonyloxy)iminobutane-2-one, and 2-ethoxycarbonyloxyimino-1-phenylpropane-1-one. In addition, examples of the oxime compound include a compound described in J.C.S. Perkin II (1979), pp. 1653-1660, J.C.S. Perkin II (1979), pp. 156-162 and Journal of Photopolymer Science and Technology (1995), pp. 202-232, or JP2000-66385A; and a compound described in JP2000-80068A, JP2004-534797A, or JP2006-342166A. As a commercially available product of the oxime compound, IRGACURE-OXE01 (manufactured by BASF SE) and IRGACURE-OXE02 (manufactured by BASF SE) can also be preferably used. In addition, TR-PBG-304 (manufactured by Changzhou Tronly New Electronic Materials Co., Ltd.), and ADEKA ARKLS NCI-930 (manufactured by Adeka Corporation) can also be used.

In addition, in addition to the above-described oxime compounds, for example, a compound described in JP2009-519904A in which oxime is linked to a N-position of carbazole, a compound described in U.S. Pat. No. 7,626,957B in which a hetero substituent is introduced into the benzophenone site, a compound described in JP2010-15025A or US2009/292039A in which a nitro group is introduced into a colorant site, a ketoxime compound described in WO2009/131189A, a compound described in U.S. Pat. No. 7,556,910B having a triazine skeleton and an oxime skeleton in the same molecule, a compound described in JP2009-221114A having an absorption maximum at 405 nm and having excellent sensitivity to a light source of g-rays, or a compound described in paragraphs "0076" to "0079" of JP2014-137466A may be used.

Other preferable examples of the oxime compound can be found in paragraphs "0274" to "0275" of JP2013-29760A, the content of which is incorporated herein by reference.

Specifically, as the oxime compound, a compound represented by the following Formula (OX-1) is preferable. In the oxime compound, an N—O bond of oxime may form an (E) isomer, a (Z) isomer, or a mixture of an (E) isomer and a (Z) isomer.

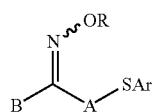

(OX-1)

In Formula (OX-1), R and B each independently represent a monovalent substituent, A represents a divalent organic group, and Ar represents an aryl group.

In Formula (OX-1), it is preferable that the monovalent substituent represented by R is a monovalent non-metal atomic group.

Examples of the monovalent non-metal atomic group include an alkyl group, an aryl group, an acyl group, an alkoxycarbonyl group, an aryloxycarbonyl group, a heterocyclic group, an alkylthiocarbonyl group, and an arylthiocarbonyl group. In addition, these groups may have one or more substituents. In addition, the above-described substituent may have another substituent.

Examples of the substituent include a halogen atom, an aryloxy group, an alkoxycarbonyl group or aryloxycarbonyl group, an acyloxy group, an acyl group, an alkyl group, and an aryl group.

In Formula (OX-1), as the monovalent substituent represented by B, an aryl group, a heterocyclic group, an arylcarbonyl group, or a heterocyclic carbonyl group is preferable. These groups may have one or more substituents. Examples of the substituent are as described above.

In Formula (OX-1), as the divalent organic group represented by A, an alkylene group having 1 to 12 carbon atoms, a cycloalkylene group, or an alkynylene group is preferable. These groups may have one or more substituents. Examples of the substituent are as described above.

In the present invention, an oxime compound having a fluorene ring can also be used as the photopolymerization initiator. Specific examples of the oxime compound having a fluorene ring include a compound described in JP2014-137466A. The content is incorporated herein by reference.

As the photopolymerization initiator, an oxime compound having a fluorine atom can also be used. Specific examples of the oxime compound having a fluorine atom include a compound described in JP2010-262028A, Compound 24 and 36 to 40 described in JP2014-500852A, and Compound (C-3) described in JP2013-164471A. The content is incorporated herein by reference.

As the photopolymerization initiator, an oxime compound having a nitro group can be used. Specific examples of the oxime compound having a nitro group include compounds described in paragraphs "0031" to "0047" of JP2013-114249A and paragraphs "0008" to "0012" and "0070" to "0079" of JP2014-137466A, and ADEKA ARKLS NCI-831 (manufactured by Adeka Corporation).

Hereinafter, specific examples of the oxime compound which are preferably used will be shown below, but the present invention is not limited thereto.

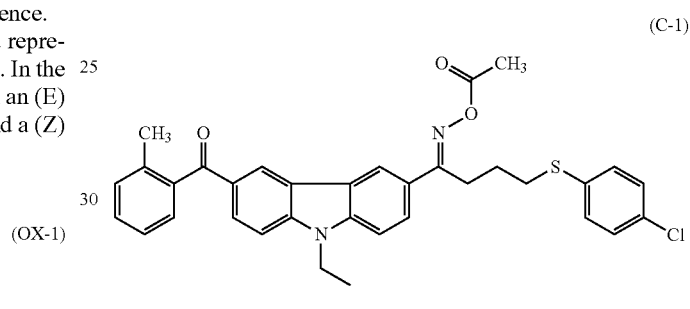

(C-1)

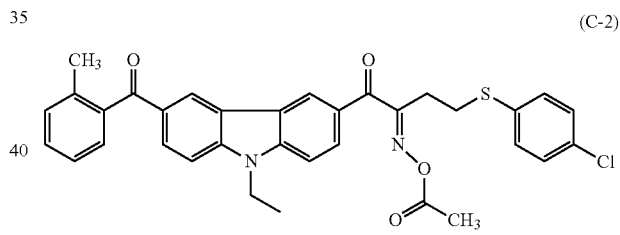

(C-2)

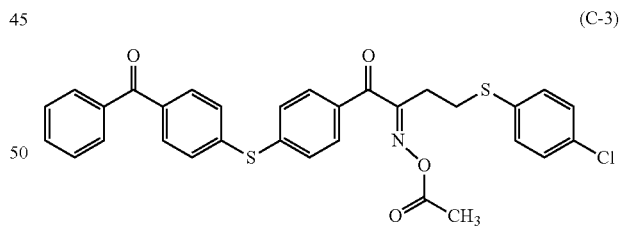

(C-3)

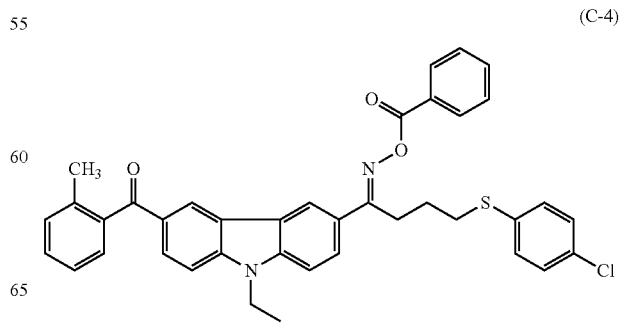

(C-4)

(C-5)
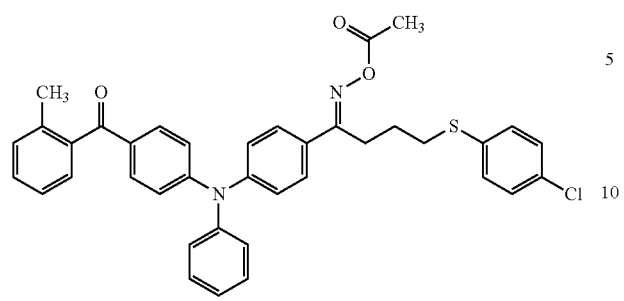
(C-6)
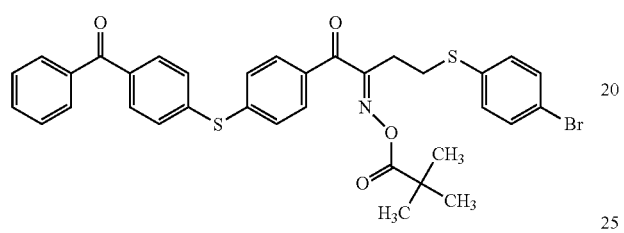
(C-7)
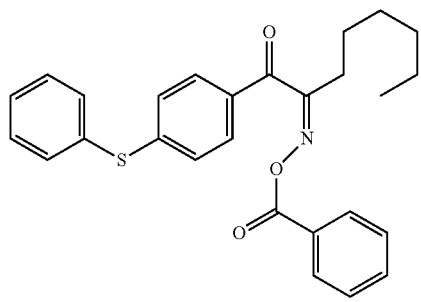
(C-8)
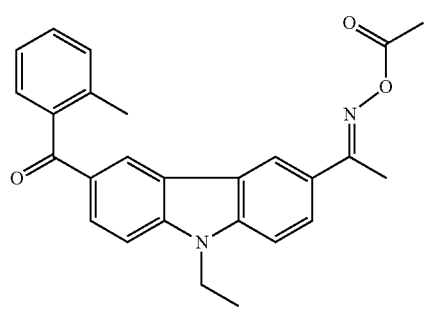
(C-9)
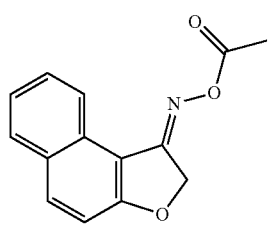
(C-10)
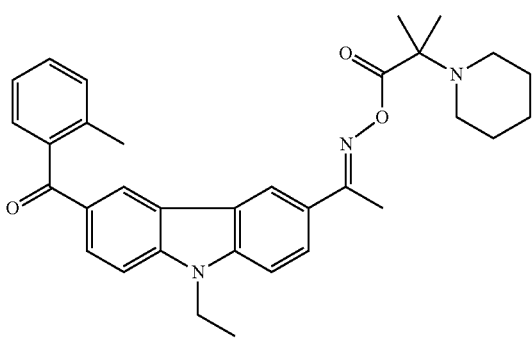
(C-11)
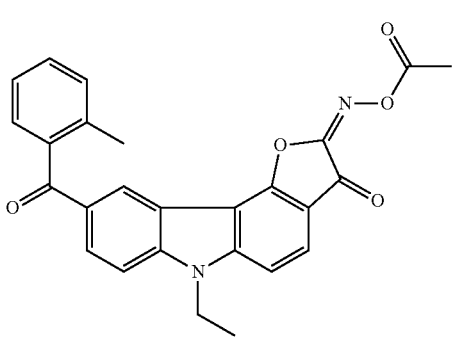
(C-12)
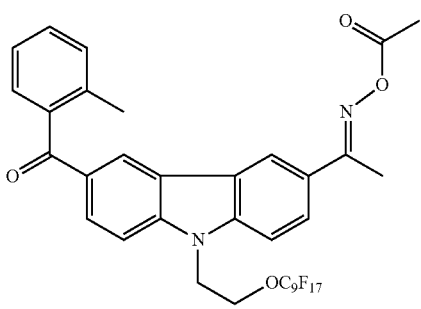
(C-13)
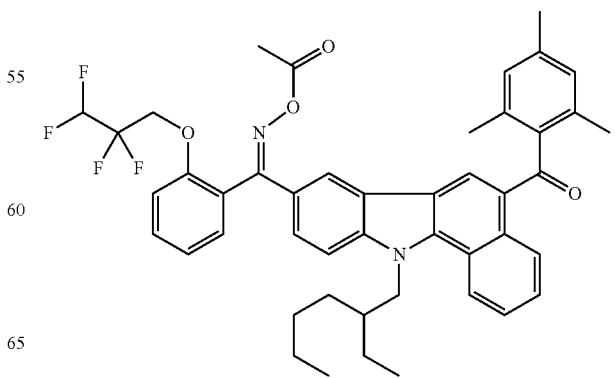

(C-14)

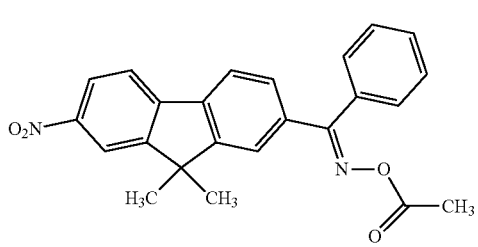

As the oxime compound, a compound having an absorption maximum in a wavelength range of 350 nm to 500 nm is preferable, a compound having an absorption wavelength in a wavelength range of 360 nm to 480 nm is more preferable, and a compound having a high absorbance at 365 nm and 405 nm is still more preferable.

The molar absorption coefficient of the oxime compound at 365 nm or 405 nm is preferably 1000 to 300000, more preferably 2000 to 300000, and still more preferably 5000 to 200000 from the viewpoint of sensitivity. The molar absorption coefficient of the compound can be measured using a well-known method. Specifically, for example, it is preferable that the molar absorption coefficient of the compound is measured using an ultraviolet-visible spectrophotometer (Cary-5 spectrophotometer, manufactured by Varian Medical Systems, Inc.) and an ethyl acetate solvent at a concentration of 0.01 g/L.

The content of the photopolymerization initiator is preferably 0.1 to 50 mass %, more preferably 0.5 to 30 mass %, and still more preferably 1 to 20 mass % with respect to the total solid content of the composition. In the above-described range, excellent sensitivity and pattern formability can be obtained. The composition may include one photopolymerization initiator or two or more photopolymerization initiators. In a case where the composition includes two or more photopolymerization initiators, it is preferable that the total content of the two or more photopolymerization initiators is in the above-described range.

<<Acid Generator>>

The composition according to the present invention may include an acid generator. In particular, in case where the composition includes a cationically polymerizable component such as a resin having a cyclic ether group or a crosslinking compound, it is preferable that the composition includes an acid generator. As the acid generator, a compound (photoacid generator) which generates an acid by light irradiation is preferable. Examples of the acid generator include compounds which are decomposed by light irradiation to generate an acid including: an onium salt compound such as a diazonium salt, a phosphonium salt, a sulfonium salt, or an iodonium salt; and a sulfonate compound such as imidosulfonate, oximesulfonate, diazodisulfone, disulfone, or ortho-nitrobenzyl sulfonate. The kind, specific compounds, and preferable examples of the acid generator can be found in the description of a compound in paragraphs "0066" to "0122" of JP2008-13646A, the content of which is also applicable to the present invention.

Examples of a compound which is preferable as the acid generator include compounds represented by the following Formulae (b1), (b2), and (b3).

$$R^{202}-\overset{\overset{R^{201}}{|}}{\underset{\underset{R^{203}}{|}}{S^+}} \quad X^- \tag{b1}$$

$$R^{204}-I^+-R^{205} \atop X^- \tag{b2}$$

$$R^{206}-\overset{O}{\underset{O}{\overset{\|}{S}}}-\overset{N_2}{\overset{\|}{\underset{\|}{C}}}-\overset{O}{\underset{O}{\overset{\|}{S}}}-R^{207} \tag{b3}$$

In Formula (b1), $R^{201}$, $R^{202}$, and $R^{203}$ each independently represent an organic group. $X^-$ represents a non-nucleophilic anion, preferably a sulfonate anion, a carboxylate anion, a bis(alkylsulfonyl)amide anion, a tris(alkylsulfonyl)methide anion, $BF_4^-$, $PF_6^-$, $SbF_6^-$, or a group shown below and more preferably $BF_4^-$, $PF_6^-$, or $SbF_6^-$.

Examples of a commercially available product of the acid generator include WPAG-469 (manufactured by Wako Pure Chemical Industries, Ltd.) and CPI-100P (manufactured by San-Apro Ltd.).

The content of the acid generator is preferably 0.1 to 50 mass %, more preferably 0.5 to 30 mass %, and still more preferably 1 to 20 mass % with respect to the total solid content of the composition. The composition according to the present invention may include one acid generator or two or more acid generators. In a case where the composition includes two or more acid generators, it is preferable that the total content of the two or more acid generators is in the above-described range.

<<Crosslinking Aid>>

It is preferable that the composition according to the present invention includes a crosslinking aid in order to promote a crosslinking reaction of a crosslinking component (the resin having a crosslinking group or the crosslinking compound). As the crosslinking aid, at least one selected from the group consisting of a polyfunctional thiol, an alcohol, an amine, and a carboxylic acid is preferable. The content of the crosslinking aid is preferably 1 to 1000 parts by mass, more preferably 1 to 500 parts by mass, and still more preferably 1 to 200 parts by mass with respect to 100 parts by mass of the crosslinking compound. The composition may include one crosslinking aids or two or more crosslinking aids. In a case where the composition includes two or more crosslinking aids, it is preferable that the total content of the two or more crosslinking aids is in the above-described range.

(Polyfunctional Thiol)

Examples of the polyfunctional thiol include a compound having two or more thiol groups in a molecule. The polyfunctional thiol is preferably a secondary alkanethiol and more preferably a compound having a structure represented by the following Formula (T1).

Formula (T1)

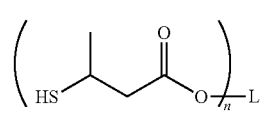

(In Formula (T1), n represents an integer of 2 to 4, and L represents a divalent to tetravalent linking group.)

In Formula (T1), it is preferable that a linking group L is an aliphatic group having 2 to 12 carbon atoms, and it is more preferable that n represents 2 and L represents an alkylene group having 2 to 12 carbon atoms. Specific examples of the polyfunctional thiol compound include compounds represented by the following Structural Formulae (T2) to (T4). Among these, a compound represented by Structural Formula (T2) is preferable. Among these polyfunctional thiol compounds, one kind may be used alone, or two or more kinds may be used in combination.

(T2)

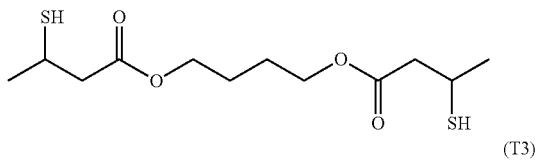

(T3)

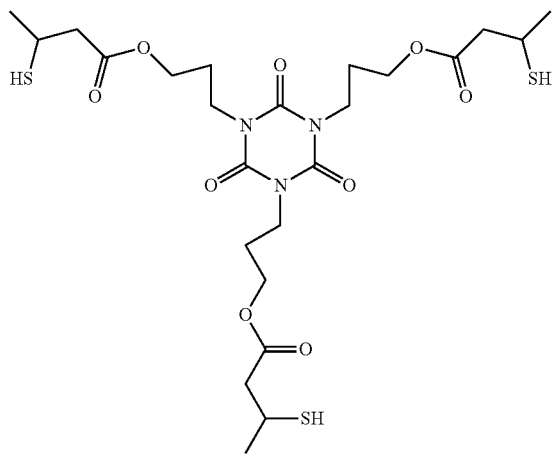

(T4)

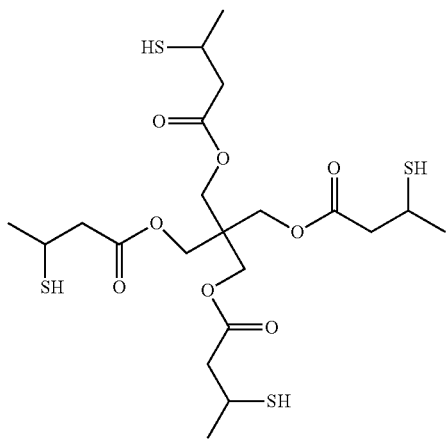

The amine as the crosslinking aid is preferably polyamine and more preferably diamine. Examples of the amine include hexamethylenediamine, triethylenetetramine, and polyethyleneimine.

(Alcohol)

The alcohol as the crosslinking aid is preferably polyhydric alcohol and more preferably diol. Examples of the alcohol include a polyether diol compound, a polyester diol compound, and a polycarbonate diol compound. Specific examples of the alcohol can be found in paragraphs "0128" to "0163" and "0172" of JP2013-253224A, the content of which is incorporated herein by reference.

(Carboxylic Acid)

Examples of the carboxylic acid as the crosslinking aid include 3,3',4,4'-biphenyltetracarboxylic anhydride, maleic acid, phthalic acid, and trimellitic acid.

<<Crosslinking Catalyst>>

The composition according to the present invention may include a crosslinking catalyst. In particular, in a case where the composition according to the present invention includes an alkoxysilyl group or a compound having a chlorosilyl group as the crosslinking compound, a sol-gel reaction is promoted and a strong cured film is obtained by including the crosslinking catalyst. Examples of the crosslinking catalyst include an acid catalyst and a base catalyst. Examples of the acid catalyst include hydrochloric acid, nitric acid, sulfuric acid, sulfurous acid, hydrogen sulfide, perchloric acid, hydrogen peroxide, carbonic acid, a carboxylic acid such as formic acid or acetic acid, a substituted carboxylic acid in which R in a structural formula represented by RCOOH is substituted with another atom or a substituent, a sulfonic acid such as benzenesulfonic acid, and phosphoric acid. Further, Lewis acid such as aluminum chloride, aluminum acetylacetonate, zinc chloride, tin chloride, a boron trifluoride diethyl ether complex, or iodotrimethylsilane may be used. In addition, examples of the base catalyst include an ammonia base compound such as ammonia water and an organic amine such as ethylamine or aniline. In addition, as the crosslinking catalyst, a catalyst described in paragraphs "0070" to "0076" of JP2013-201007A can also be used.

The content of the crosslinking catalyst is preferably 0.1 to 100 parts by mass, more preferably 0.1 to 50 parts by mass, and still more preferably 0.1 to 20 parts by mass with respect to 100 parts by mass of the crosslinking compound. The composition may include one crosslinking catalyst or two or more crosslinking catalysts. In a case where the composition includes two or more crosslinking catalysts, it is preferable that the total content of the two or more crosslinking catalysts is in the above-described range.

<<Solvent>>

The composition according to the present invention may include a solvent. Examples of the solvent include water and an organic solvent. Basically, the solvent is not particularly limited as long as it satisfies the solubility of each component and the coating properties of the composition. However, it is preferable that the organic solvent is selected in consideration of the coating properties and safety of the composition.

Preferable examples of the organic solvent are the following solvents:

an ester, for example, ethyl acetate, n-butyl acetate, isobutyl acetate, cyclohexyl acetate, amyl formate, isoamyl acetate, butyl propionate, isopropyl butyrate, ethyl butyrate, butyl butyrate, methyl lactate, ethyl lactate, an alkyl oxyacetate (for example, methyl oxyacetate, ethyl oxyacetate, or butyl oxyacetate (for example, methyl methoxyacetate, ethyl methoxyacetate, butyl methoxyacetate, methyl ethoxyacetate, or ethyl ethoxyacetate)), a 3-oxypropionic acid alkyl ester (for example, 3-methyl oxypropionate or 3-ethyl oxypropionate (for example, methyl 3-methoxypropionate, ethyl 3-methoxypropionate, methyl 3-ethoxypropionate, or ethyl 3-ethoxypropionate)), a 2-oxypropionic acid alkyl ester (for example, methyl 2-oxypropionate, ethyl 2-oxypropionate, or propyl 2-oxypropionate (for example, methyl 2-methoxypropionate, ethyl 2-methoxypropionate, propyl 2-methoxypropionate, methyl 2-ethoxypropionate, or ethyl 2-ethoxypropionate)), methyl 2-oxy-2-methylpropionate or ethyl 2-oxy-2-methylpropionate (for example, methyl 2-methoxy-2-methylpropionate or ethyl 2-ethoxy-2-methylpropionate), methyl pyruvate, ethyl pyruvate, propyl pyruvate, methyl acetoacetate, ethyl acetoacetate, methyl 2-oxobutanoate or ethyl 2-oxobutanoate;

an ether, for example, diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate, or propylene glycol monopropyl ether acetate;

a ketone, for example, methyl ethyl ketone, cyclohexanone, cyclopentanone, 2-heptanone, or 3-heptanone; and an aromatic hydrocarbon, for example, toluene or xylene.

Among these organic solvents, one kind may be used alone, or two or more kinds may be used in combination. In a case where two or more organic solvents are used in combination, in particular, a mixed solution is preferable, the mixed solution including two or more organic solvents selected from the group consisting of methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol methyl ether acetate.

As the solvent, an solvent having a low metal content is preferable. For example, the metal content in the solvent is preferably 10 ppb or lower. Optionally, a solvent having a metal content at a ppt level may be used. For example, such a high-purity solvent is available from Toyo Gosei Co., Ltd.

Examples of a method of removing impurities such as metal from the solvent include distillation (for example, molecular distillation or thin-film distillation) and filtering using a filter. During the filtering using a filter, the pore size of a filter is preferably 10 nm or less, more preferably 5 nm or less, and still more preferably 3 nm or less. As a material of the filter, polytetrafluoroethylene, polyethylene, or nylon is preferable.

The solvent may include an isomer (a compound having the same number of atoms and a different structure). In addition, the organic solvent may include only one isomer or a plurality of isomers.

As the organic solvent, an organic solvent containing 0.8 mmol/L or lower of a peroxide is preferable, and an organic solvent containing no peroxide is more preferable.

The content of the solvent is preferably 10 to 90 mass %, more preferably 20 to 80 mass %, and still more preferably 25 to 75 mass % with respect to the total mass of the composition.

<<Polymerization Inhibitor>>

The composition according to the present invention may include a polymerization inhibitor in order to prevent unnecessary thermal polymerization of the crosslinking compound during the manufacturing or storage of the composition.

Examples of the polymerization inhibitor include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitrosophenylhydroxyamine salt (for example, an ammonium salt or a cerium (III) salt). Among these, p-methoxyphenol is preferable.

The content of the polymerization inhibitor is preferably 0.01 to 5 mass % with respect to the total solid content of the composition.

<<Surfactant>>

The composition according to the present invention may include various surfactants from the viewpoint of further improving coating properties. As the surfactants, various surfactants such as a fluorine surfactant, a nonionic surfactant, a cationic surfactant, an anionic surfactant, or a silicone surfactant can be used.

By the composition including a fluorine surfactant, liquid characteristics (for example, fluidity) of a coating solution prepared from the composition are further improved, and the uniformity in coating thickness and liquid saving properties can be further improved. That is, in a case where a film is formed using a coating solution prepared using the composition including a fluorine surfactant, the interfacial tension between a coated surface and the coating solution decreases, the wettability on the coated surface is improved, and the coating properties on the coated surface are improved. Therefore, a film having a uniform thickness with reduced unevenness in thickness can be formed more suitably.

The fluorine content in the fluorine surfactant is preferably 3 to 40 mass %, more preferably 5 to 30 mass %, and still more preferably 7 to 25 mass %. The fluorine surfactant in which the fluorine content is in the above-described range is effective from the viewpoints of the uniformity in the thickness of the coating film and liquid saving properties, and the solubility thereof in the composition is also excellent.

Examples of the fluorine surfactant include a surfactant described in paragraphs "0060" to "0064" of JP2014-41318A (paragraphs "0060" to "0064" of corresponding WO2014/17669), the content of which is incorporated herein by reference. Examples of a commercially available product of the fluorine surfactant include: MEGAFACE F171, F172, F173, F176, F177, F141, F142, F143, F144, R30, F437, F475, F479, F482, F554, F780, and RS-72-K (all of which are manufactured by DIC Corporation); FLUORAD FC430, FC431, and FC171 (all of which are manufactured by Sumitomo 3M Ltd.); SURFLON S-382, SC-101, SC-103, SC-104, SC-105, SC-1068, SC-381, SC-383, S-393, and KH-40 (all of which are manufactured by Asahi Glass Co., Ltd.); and PF636, PF656, PF6320, PF6520, and PF7002 (all of which are manufactured by OMNOVA Solutions Inc.).

As the fluorine surfactant, a block polymer can also be used, and specific examples thereof include a compound described in JP2011-89090A. As the fluorine surfactant, a fluorine-containing polymer compound can be preferably used, the fluorine-containing polymer compound including: a repeating unit derived from a (meth)acrylate compound having a fluorine atom; and a repeating unit derived from a (meth)acrylate compound having 2 or more (preferably 5 or more) alkyleneoxy groups (preferably an ethyleneoxy group and a propyleneoxy group). For example, the following compound can also be used as the fluorine surfactant used in the present invention.

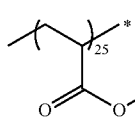 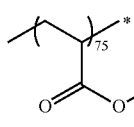
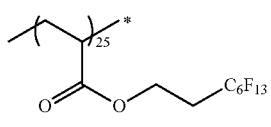 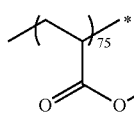 
Mixture

The weight-average molecular weight of the compound is preferably 3000 to 50000 and, for example, 14000.

In addition, a fluorine-containing polymer having an ethylenically unsaturated group at a side chain can also be preferably used as the fluorine surfactant. Specific examples include compounds described in paragraphs "0050" to "0090" and paragraphs "0289" to "0295" of JP2010-164965A, for example, MEGAFACE RS-101, RS-102, RS-718K, and RS-72-K manufactured by DIC Corporation. The fluorine-containing polymer having an ethylenically unsaturated group at a side chain corresponds to a surfactant and is a different component from the resin having a crosslinking group and the crosslinking compound. As the fluorine surfactant, a compound described in paragraphs "0015" to "0158" of JP2015-117327A can also be used.

Specific examples of the nonionic surfactant include glycerol, trimethylolpropane, trimethylolethane, an ethoxylate and a propoxylate thereof (for example, glycerol propoxylate or glycerin propoxylate), polyoxyethylene lauryl ether, polyoxyethylene stearyl ether, polyoxyethylene oleyl ether, polyoxyethylene octylphenyl ether, polyoxyethylene nonylphenyl ether, polyethylene glycol dilaurate, polyethylene glycol distearate, and sorbitan fatty acid esters (PLURONIC L10, L31, L61, L62, 10R5, 17R2, and 25R2 and TETRONIC 304, 701, 704, 901, 904, and 150R1 (all of which are manufactured by BASF SE); and SOLSPERSE 20000 (manufactured by Lubrication Technology Inc.). In addition, NCW-101, NCW-1001, or NCW-1002 (manufactured by Wako Pure Chemical Industries, Ltd.) can also be used.

Specific examples of the cationic surfactant include a phthalocyanine derivative (trade name: EFKA-745, manufactured by Morishita Co., Ltd.), an organosiloxane polymer KP341 (manufactured by Shin-Etsu Chemical Co., Ltd.), a (meth)acrylic acid (co)polymer POLYFLOW No. 75, No. 90, or No. 95 (manufactured by Kyoeisha Chemical Co., Ltd.), and W001 (manufactured by Yusho Co., Ltd.).

Specific examples of the anionic surfactant include W004, W005, and W017 (manufactured by Yusho Co., Ltd.), and SANDET BL (manufactured by Sanyo Chemical Industries Ltd.).

Examples of the silicone surfactant include: TORAY SILICONE DC3PA, TORAY SILICONE SH7PA, TORAY SILICONE DC11PA, TORAY SILICONE SH21PA, TORAY SILICONE SH28PA, TORAY SILICONE SH29PA, TORAY SILICONE SH30PA, and TORAY SILICONE SH8400 (all of which are manufactured by Dow Corning Corporation); TSF-4440, TSF-4300, TSF-4445, TSF-4460, and TSF-4452 (all of which are manufactured by Momentive Performance Materials Inc.); KP341, KF6001, and KF6002 (all of which are manufactured by Shin-Etsu Chemical Co., Ltd.); and BYK307, BYK323, and BYK330 (all of which are manufactured by BYK-Chemie Japan K.K.).

Among these surfactants, one kind may be used alone, or two or more kinds may be used in combination.

The content of the surfactant is preferably 0.001 to 2.0 mass % and more preferably 0.005 to 1.0 mass % with respect to the total solid content of the composition.

<<Ultraviolet Absorber>>

The composition according to the present invention may include an ultraviolet absorber. The ultraviolet absorber is preferably a conjugated diene compound and more preferably a compound represented by the following Formula (1).

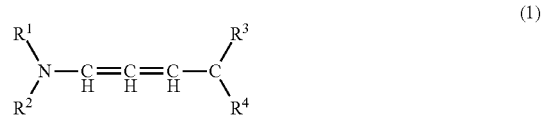

(1)

$R^1$ and $R^2$ each independently represent a hydrogen atom, an alkyl group having 1 to 20 carbon atoms, or an aryl group having 6 to 20 carbon atoms, and may be the same as or different from each other but does not represent a hydrogen atom at the same time.

$R^3$ and $R^4$ represent an electron-withdrawing group. Here, the electron-withdrawing group is an electron-withdrawing group having a Hammett substituent constant σp value (hereinafter, simply referred to as "σp value") of 0.20 to 1.0. The σp value in the electron-withdrawing group is preferably 0.30 to 0.8. $R^3$ and $R^4$ represent preferably an acyl group, a carbamoyl group, an alkyloxycarbonyl group, an aryloxycarbonyl group, a cyano group, a nitro group, an alkylsulfonyl group, an arylsulfonyl group, a sulfonyloxy group, or a sulfamoyl group, and more preferably an acyl group, a carbamoyl group, an alkyloxycarbonyl group, an aryloxycarbonyl group, a cyano group, an alkylsulfonyl group, an arylsulfonyl group, a sulfonyloxy group, or a sulfamoyl group. The details of Formula (1) can be found in paragraphs "0148" to "0158" of JP2010-049029A, the content of which is incorporated herein by reference.

Specific examples of the compound represented by Formula (1) include the following compounds. Other examples of the compound represented by Formula (1) include a compound described in paragraphs "0160" to "0162" of JP2010-049029A, the content of which is incorporated herein by reference.

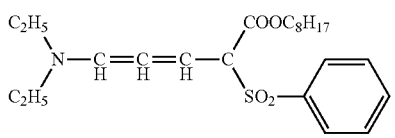

Examples of a commercially available product of the ultraviolet absorber include UV503 (manufactured by Daito Chemical Co., Ltd.).

The content of the ultraviolet absorber is preferably 0.01 to 10 mass % and more preferably 0.01 to 5 mass % with respect to the total solid content of the composition according to the present invention.

<<Other Components>>

Optionally, the near infrared absorbing composition may further include a dispersant, a sensitizer, a curing accelerator, a filler, a thermal curing accelerator, a thermal polymerization inhibitor, a plasticizer, an adhesion accelerator, and other auxiliary agents (for example, conductive particles, a filler, an antifoaming agent, a flame retardant, a leveling agent, a peeling accelerator, an antioxidant, an aromatic chemical, a surface tension adjuster, or a chain transfer agent). By the near infrared absorbing composition appropriately including the components, properties of a desired near infrared cut filter such as stability or film properties can be adjusted. The details of the components can be found in, for example, paragraph "0183" of JP2012-003225A (corresponding to "0237" of US2013/0034812A) and paragraphs "0101" to "0104" and "0107" to "0109" of JP2008-250074A, the content of which is incorporated herein by reference. In addition, examples of the antioxidant include a phenol compound, a phosphite compound, and a thioether compound. A phenol compound having a molecular weight of 500 or higher, a phosphite compound having a molecular weight of 500 or higher, or a thioether compound having a molecular weight of 500 or higher is more preferable. Among these compounds, a mixture of two or more kinds may be used. As the phenol compound, an arbitrary phenol compound which is known as a phenol antioxidant can be used. As the phenol compound, for example, a hindered phenol compound is preferable. In particular, a compound having a substituent at a position (ortho-position) adjacent to a phenolic hydroxyl group is preferable. As the substituent, a substituted or unsubstituted alkyl group having 1 to 22 carbon atoms is preferable, and a methyl group, an ethyl group, a propionyl group, an isopropionyl group, a butyl group, an isobutyl group, a t-butyl group, a pentyl group, an isopentyl group, a t-pentyl group, a hexyl group, an octyl group, an isooctyl group, or a 2-ethylhexyl group is more preferable. In addition, a compound (antioxidant) having a phenol group and a phosphite group in the same molecule is also preferable. In addition, as the antioxidant, a phosphorus-based antioxidant can also be preferably used. Examples of the phosphorus-based antioxidant include at least one compound selected from the group consisting of tris[2-[[2,4,8,10-tetrakis(1,1-dimethylethyl)dibenzo[d,f][1,3,2]dioxaphosphepin-6-yl]oxy]ethyl]amine, tris[2-[(4,6,9,11-tetra-t-butyldibenzo[d,f][1,3,2]dioxaphosphepin-2-yl)oxy]ethyl] amine, and ethyl bis(2,4-di-t-butyl-6-methylphenyl) phosphite. The phosphorus-based antioxidant is easily commercially available, and examples of the commercially available product include ADEKA STAB AO-20, ADEKA STAB AO-30, ADEKA STAB AO-40, ADEKA STAB AO-50, ADEKA STAB AO-50F, ADEKA STAB AO-60, ADEKA STAB AO-60G, ADEKA STAB AO-80, and ADEKA STAB AO-330 (all of which are manufactured by Adeka Corporation). The content of the antioxidant is preferably 0.01 to 20 mass % and more preferably 0.3 to 15 mass % with respect to the mass of the total solid content of the composition. As the antioxidant, one kind may be used alone, or two or more kinds may be used. In a case where two or more antioxidants are used in combination, it is preferable that the total content of the two or more antioxidants is in the above-described range.

<Method of Preparing Composition>

The composition according to the present invention can be prepared by mixing the above-described components with each other. During the preparation of the composition, the respective components may be mixed with each other collectively, or may be mixed with each other sequentially after dissolved and dispersed in a solvent. In addition, during mixing, the order of addition or working conditions is not particularly limited. For example, all the components may be dissolved or dispersed in a solvent at the same time to prepare the composition. Optionally, two or more solutions or dispersions may be appropriately prepared using the respective components, and the solutions or dispersions may be mixed with each other during use (during application) to prepare the composition.

During the preparation of the composition, it is preferable that each of the components is filtered through a filter, for example, in order to remove foreign matter or to reduce defects. As the filter, any filter which is used in the related art for filtering or the like can be used without any particular limitation. Examples of a material of the filter include: a fluororesin such as polytetrafluoroethylene (PTFE); a polyamide resin such as nylon (for example, nylon-6 or nylon-6,6); and a polyolefin resin (having a high density and an ultrahigh molecular weight) such as polyethylene or polypropylene (PP). Among these materials, polypropylene (including high-density polypropylene) or nylon is preferable.

The pore size of the filter is suitably about 0.01 to 7.0 μm and is preferably about 0.01 to 3.0 μm and more preferably about 0.05 to 0.5 μm. In the above-described range, fine foreign matter, which inhibits a fine and smooth composition in the next step, can be reliably removed. In addition, a fibrous filter material is also preferably used, and examples of the filter material include polypropylene fiber, nylon fiber, and glass fiber. Specifically, a filter cartridge of SBP type series (manufactured by Roki Techno Co., Ltd.; for example, SBP008), TPR type series (for example, TPR002 or TPR005), SHPX type series (for example, SHPX003), or the like can be used.

In a filter is used, a combination of different filters may be used. At this time, the filtering using a first filter may be performed once, or twice or more.

In addition, a combination of first filters having different pore sizes in the above-described range may be used. Here, the pore size of the filter can refer to a nominal value of a manufacturer of the filter. A commercially available filter can be selected from various filters manufactured by Pall Corporation (for example, DFA4201NXEY), Toyo Roshi Kaisha, Ltd., Entegris Japan Co., Ltd. (former Mykrolis Corporation), or Kits Microfilter Corporation.

A second filter may be formed of the same material as that of the first filter.

For example, the filtering using the first filter may be performed only on the dispersion, and the filtering using the second filter may be performed on a mixture of the dispersion and other components.

<Film and Near Infrared Cut Filter>

Next, a film according to the present invention will be described. The film according to the present invention is formed of the above-described composition according to the present invention. The film according to the present invention has excellent infrared shielding properties and visible transparency, and thus can be preferably used as an infrared cut filter or an infrared transmitting filter. Further heat resistance and light fastness are also excellent. The film according to the present invention may be a film having a pattern or a film (flat film) not having a pattern. In a case where the film according to the present invention is used as an infrared transmitting filter, examples of the infrared transmitting filter include a filter that shields visible light and allows transmission of light in a wavelength range of 900 nm or longer. In a case where the film according to the present invention is used as an infrared transmitting filter, it is preferable that infrared transmitting filter is a filter that is formed of a composition including the squarylium compound and the coloring material that shields visible light (preferably a coloring material including two or more chromatic colorants or a coloring material including at least an organic black colorant), or is a filter in which a layer of the coloring material that shields visible light is separately present in addition to a layer including the squarylium compound. In a case where the film according to the present invention is used as an infrared transmitting filter, the squarylium compound has a function of limiting an infrared range of light to be transmitted (infrared light) to a long wavelength side.

In addition, the infrared cut filter according to the present invention is formed of the above-described composition according to the present invention.

The thickness of the film according to the present invention can be adjusted according to the purpose. The thickness is preferably 20 µm or less, more preferably 10 µm or less, and still more preferably 5 µm or less. For example, the lower limit of the thickness is preferably 0.1 µm or more, more preferably 0.2 µm or more, and still more preferably 0.3 µm or more. The film according to the present invention can be preferably used as an infrared cut filter of a solid image pickup element such as a charge coupled device (CCD) or a complementary metal-oxide semiconductor (CMOS). In addition, the infrared cut filter according to the present invention can be used in various image display devices.

The film (infrared cut filter) according to the present invention can be used in combination with a color filter that includes a chromatic colorant.

The color filter can be manufactured using a coloring composition including a chromatic colorant. Examples of the chromatic colorant include the chromatic colorants described regarding the composition according to the present invention. The coloring composition may further include, for example, a resin, a compound having a cross-linking group, a photopolymerization initiator, a surfactant, a solvent, a polymerization inhibitor, and an ultraviolet absorber. In more detail, for example, the materials described above regarding the composition according to the present invention can be used. In addition, the film (infrared cut filter) according to the present invention may have not only a function as an infrared cut filter but also a function as a color filter by including a chromatic colorant.

In the present invention, "infrared cut filter" refers to a filter that allows transmission of light (visible light) in the visible range and shields light (infrared light) in the infrared range. The infrared cut filter may be a filter that allows transmission of light in the entire wavelength range of the visible range, or may be a filter that allows transmission of light in a specific wavelength range of the visible range and shields light in another specific wavelength range of the visible range. In addition, in the present invention, "color filter" refers to a filter that allows transmission of light in a specific wavelength range of the visible range and shields light in another specific wavelength range of the visible range. In addition, "infrared transmitting filter" refers to a filter that shields light (visible light) in the visible range and allows transmission of light (infrared light) in the infrared range.

In a case where the film according to the present invention is used as an infrared transmitting filter, it is preferable that the film according to the present invention has the following spectral characteristics (1). According to this aspect, a film capable of allowing transmission of infrared light in a state where noise generated from visible light is small can be formed.

(1) A light transmittance in a thickness direction of the film has a maximum value of 20% or lower in a wavelength range of 400 to 830 nm and has a minimum value of 80% or higher in a wavelength range of 1000 to 1300 nm The film having the above-described spectral characteristics can be preferably used as an infrared transmitting filter that shields light in a wavelength range of 400 to 750 nm and allows transmission of light in a wavelength range of 900 nm or longer.

The spectral characteristics of the film are values obtained by measuring the transmittance in a wavelength range of 300 to 1300 nm using an ultraviolet-visible-near infrared spectrophotometer (U-4100, manufactured by Hitachi High-Technologies Corporation).

In a case where the film according to the present invention is used as an infrared cut filter or an infrared transmitting filter, an infrared cut filter and an infrared transmitting filter can be used in combination. By using an infrared cut filter and an infrared transmitting filter in combination with an infrared transmitting filter, this combination can be preferably used for an infrared sensor that detects infrared light at a specific wavelength. In a case where both an infrared cut filter and an infrared transmitting filter are used in combination, either or both of the infrared cut filter and the infrared transmitting filter can be formed using the composition according to the present invention.

In addition, in a case where the film according to the present invention is used as an infrared cut filter, the infrared cut filter may be or may not be adjacent to a color filter in the thickness direction. In a case where the infrared cut filter is not adjacent to the color filter in the thickness direction, the infrared cut filter may be formed on another substrate other than a substrate on which the color filter is formed, or another member (for example, a microlens or a planarizing layer) constituting a solid image pickup element may be interposed between the infrared cut filter and the color filter.

In addition, the near infrared cut filter may further include a dielectric multi-layer film or an ultraviolet absorbing layer in addition to the film according to the present invention. By further including the dielectric multi-layer film, the infrared cut filter having a wide view angle and excellent infrared shielding properties can be easily obtained. In addition, by including the ultraviolet absorbing layer, the infrared cut filter according to the present invention having excellent ultraviolet shielding properties can be obtained. The details of the ultraviolet absorbing layer can be found in the description of an absorbing layer described in paragraphs "0040" to "0070" and paragraphs "0119" to "0145" of WO2015/099060. The details of the dielectric multi-layer film can be found in paragraphs "0255" to "0259" of JP2014-41318A <Pattern Forming Method>

A pattern forming method includes: a step of forming a layer formed of the composition according to the present invention on a support; and a step of forming a pattern on the composition layer using a photolithography method or a dry etching method.

In a case where a laminate in which the film according to the present invention and a color filter are laminated is manufactured, pattern formation on the film according to the present invention and pattern formation on the color filter may be separately performed. In addition, pattern formation may be performed on the laminate in which the film according to the present invention and the color filter are laminated (that is, pattern formation on the film according to the present invention and pattern formation on the color filter may be simultaneously performed).

The case where pattern formation on the film according to the present invention (infrared cut filter) and pattern formation on the color filter are separately performed denotes the following aspect. Pattern formation is performed on any one of the film according to the present invention (infrared cut filter) and the color filter. Next, the other filter layer is formed on the filter layer on which the pattern is formed. Next, pattern formation is performed on the filter layer on which a pattern is not formed.

A pattern forming method may be a pattern forming method using photolithography or a pattern forming method using dry etching.

In a case where the pattern forming method using photolithography is adopted, a dry etching step is not necessary, and an effect that the number of steps can be reduced can be obtained.

In a case where the pattern forming method using dry etching is adopted, a photolithography function is not necessary. Therefore, an effect that the concentration of an infrared absorber or the like in the composition according to the present invention can increase can be obtained.

In a case where the pattern formation on the film according to the present invention (infrared cut filter) and the pattern formation on the color filter are separately performed, the pattern formations on the respective filter layers may be performed using only the photolithography method or only the dry etching method. In addition, after performing the pattern formation on one filter layer using the photolithography method, the pattern formation may be performed on the other filter layer using the dry etching method. In a case where the pattern formation is performed using a combination of the dry etching method and the photolithography method, it is preferable that a pattern is formed on a first layer using the dry etching method and a pattern is formed on a second or subsequent layer using the photolithography method.

It is preferable that the pattern formation using the photolithography method includes: a step of forming a composition layer on a support; a step of exposing the composition layer in a pattern shape; and a step of forming a pattern by removing a non-exposed portion by development. Optionally, the pattern formation further includes: a step (pre-baking step) of baking the composition layer; and a step (post-baking step) of baking the developed pattern.

In addition, it is preferable that the pattern formation using the dry etching method includes: a step of forming a composition layer on a support and curing the cured composition layer; a step of forming a photoresist layer on the cured composition layer; a step of obtaining a resist pattern by patterning the photoresist layer by exposure and development; and a step of forming a pattern by dry-etching the cured composition layer by using the resist pattern as an etching mask. Hereinafter, the respective steps will be described.

<<Step of Forming Composition Layer>>

In the step of forming a composition layer, a composition is applied to the support to form a composition layer.

As the support, for example, a substrate for a solid image pickup element obtained by providing a solid image pickup element (light-receiving element) such as CCD or CMOS on a substrate (for example, a silicon substrate) can be used.

The pattern may be formed on a solid image pickup element-formed surface (front surface) of the substrate for a solid image pickup element, or may be formed on a solid image pickup element non-formed surface (back surface) thereof.

Optionally, an undercoat layer may be provided on the support to improve adhesion with a layer above the support, to prevent diffusion of materials, or to make a surface of the substrate flat.

As a method of applying the composition to the support, various methods such as slit coating, an ink jet method, spin coating, cast coating, roll coating, or screen printing can be used.

The composition layer formed on the support may be dried (pre-baked). In a case where a pattern is formed through a low-temperature process, pre-baking is not necessarily performed.

In a case where pre-baking is performed, the pre-baking temperature is preferably 150° C. or lower, more preferably 120° C. or lower, and still more preferably 110° C. or lower. The lower limit is, for example, 50° C. or higher or 80° C. or higher. By performing pre-baking at 150° C. or lower, the characteristics can be effectively maintained, for example, even in a case where a photoelectric conversion film of an image sensor is formed of an organic material.

The pre-baking time is preferably 10 to 300 seconds, more preferably 40 to 250 seconds, and still more preferably 80 to 220 seconds. Drying can be performed using a hot plate, an oven, or the like.

In a case where the pattern formation is simultaneously performed on a plurality of layers, it is preferable that a composition for forming another layer is applied to the composition layer to form another composition layer.

(Case where Pattern is Formed Using Photolithography Method)

<<Exposure Step>>

Next, the composition layer is exposed in a pattern shape (exposure step). For example, the composition layer is exposed in a pattern shape using an exposure device such as a stepper through a mask having a predetermined mask pattern, thereby exposing a pattern. As a result, an exposed portion can be cured.

As radiation (light) used during the exposure, ultraviolet rays such as g-rays or i-rays are preferably used (i-rays are more preferably used). The irradiation dose (exposure dose) is preferably 0.03 to 2.5 J/cm$^2$, more preferably 0.05 to 1.0 J/cm$^2$, and most preferably 0.08 to 0.5 J/cm$^2$.

The oxygen concentration during exposure can be appropriately selected. The exposure may be performed not only in air but also in a low-oxygen atmosphere having an oxygen concentration of 19 vol % or lower (for example, 15 vol %, 5 vol %, or substantially 0 vol %) or in a high-oxygen atmosphere having an oxygen concentration of higher than 21 vol % (for example, 22 vol %, 30 vol %, or 50 vol %).

In addition, the exposure illuminance can be appropriately set and typically can be selected in a range of 1000 W/m² to 100000 W/m² (for example, 5000 W/m², 15000 W/m², or 35000 W/m²). Conditions of the oxygen concentration and conditions of the exposure illuminance may be appropriately combined.

For example, conditions are oxygen concentration: 10 vol % and illuminance: 10000 W/m², or oxygen concentration: 35 vol % and illuminance: 20000 W/m².

<<Development Step>>

Next, a pattern is formed by removing a non-exposed portion by development. The non-exposed portion can be removed by development using a developer. As a result, a non-exposed portion of the composition layer in the exposure step is eluted into the developer, and only the photocured portion remains.

As the developer, an organic alkali developer which does not cause damages to a solid image pickup element as a substrate, a circuit or the like is desired.

For example, the temperature of the developer is preferably 20° C. to 30° C. The developing time is preferably 20 to 180 seconds. In addition, in order to further improve residue removing properties, a step of shaking the developer off per 60 seconds and supplying a new developer may be repeated multiple times.

Examples of an alkaline agent used in the developer include an organic alkaline compound such as ammonia water, ethylamine, diethylamine, dimethylethanolamine, tetramethylammonium hydroxide, tetraethylammonium hydroxide, tetrapropylammonium hydroxide, tetrabutylammonium hydroxide, benzyltrimethylammonium hydroxide, choline, pyrrole, piperidine, or 1,8-diazabicyclo-[5,4,0]-7-undecene. As the developer, an alkaline aqueous solution is preferably used in which the above alkaline agent is diluted with pure water such that a concentration thereof is 0.001 to 10 mass % and preferably 0.01 to 1 mass %.

In addition, an inorganic alkali may be used as the developer. Preferable examples of the inorganic alkali include sodium hydroxide, potassium hydroxide, sodium carbonate, sodium bicarbonate, sodium silicate, and sodium metasilicate. In addition, a surfactant may be used as the developer. Examples of the surfactant include the surfactants described above regarding the composition. Among these, a nonionic surfactant is preferable. In a case where a developer including the alkaline aqueous solution is used, in general, it is preferable that the film is rinsed with pure water after development.

After the development, it is preferable that the film is dried and then heated (post-baking). Post-baking is a heat treatment which is performed after development to completely cure the film. In a case where post-baking is performed, for example, the post-baking temperature is preferably 100° C. to 240° C. From the viewpoint of curing the film, the post-baking temperature is more preferably 200° C. to 230° C. In addition, in a case where an organic electroluminescence (organic EL) element is used as a light-emitting light source, or in a case where a photoelectric conversion film of an image sensor is formed of an organic material, the post-baking temperature is preferably 150° C. or lower, more preferably 120° C. or lower, still more preferably 100° C. or lower, and even still more preferably 90° C. or lower. The lower limit is, for example, 50° C. or higher. The film after the development is post-baked continuously or batch-wise using heating means such as a hot plate, a convection oven (hot air circulation dryer), a high-frequency heater under the above-described conditions. In addition, in a case where a pattern is formed through a low-temperature process, post-baking is not necessarily performed.

(Case where Pattern is Formed Using Dry Etching Method)

The pattern formation using the dry etching method can be performed by curing the composition layer formed on the support to form a cured composition layer, and then etching the cured composition layer with etching gas by using a patterned photoresist layer as a mask. Specifically, it is preferable that a positive type or negative type radiation sensitive composition is applied to the cured composition layer and is dried such that a photoresist layer is formed. It is preferable that pre-baking is further performed in order to form the photoresist layer. In particular, in a preferable aspect, as a process of forming the photoresist layer, baking after exposure or baking after development (post-baking) is performed. The details of the pattern formation using the dry etching method can be found in paragraphs "0010" to "0067" of JP2013-064993A, the content of which is incorporated herein by reference.

<Solid Image Pickup Element>

A solid image pickup element according to the present invention includes the film according to the present invention. The solid image pickup element includes the film according to the present invention (infrared cut filter). The configuration of the solid image pickup element is not particularly limited as long as the solid image pickup element functions. For example, the following configuration can be adopted.

For example, the solid image pickup element includes a support and components formed on the support including a plurality of photodiodes, a transfer electrode formed of polysilicon or the like, a light shielding film, a device protective film, and the film according to the present invention. The photodiodes configure a light receiving area of the solid image pickup element. The light shielding film formed of tungsten or the like is provided on the photodiodes and the transfer electrode, and has openings through only light receiving sections of the photodiodes. The device protective film formed of silicon nitride or the like is formed on the light shielding film so as to cover the entire surface of the light shielding film and the light receiving sections of the photodiodes. The film according to the present invention is formed on the device protective film.

The solid image pickup element may further include light collecting means (for example, a microlens). The light collecting means may be provided above the device protective film and below the film (infrared cut filter) according to the present invention (on a side thereof close to the support), or may be disposed above the film according to the present invention.

<Image Display Device>

The film according to the present invention can also be used in an image display device such as a liquid crystal display device or an organic electroluminescence (organic EL) display device. For example, by using the near infrared cut filter in combination with the respective colored pixels (for example, red, green, blue), the near infrared cut filter can be used for the purpose of shielding infrared light included in light emitted from a backlight (for example, a white light emitting diode (white LED)) of a display device to prevent a malfunction of a peripheral device, or for the purpose of forming an infrared pixel in addition to the respective color display pixels.

The definition of a display device and the details of each display device can be found in, for example, "Electronic Display Device (by Akiya Sasaki, Kogyo Chosakai Publishing Co., Ltd., 1990)" or "Display Device (Sumiaki Ibuki, Sangyo Tosho Co., Ltd.). In addition, the details of a liquid crystal display device can be found in, for example, "Next-Generation Liquid Crystal Display Techniques (Edited by Tatsuo Uchida, Kogyo Chosakai Publishing Co., Ltd., 1994)". The liquid crystal display device to which the present invention is applicable is not particularly limited. For example, the present invention is applicable to various liquid crystal display devices described in "Next-Generation Liquid Crystal Display Techniques".

The image display device may include a white organic EL element. It is preferable that the white organic EL element has a tandem structure. The tandem structure of the organic EL element is described in, for example, JP2003-45676A, or pp. 326-328 of "Forefront of Organic EL Technology Development-Know-How Collection of High Brightness, High Precision, and Long Life" (Technical Information Institute, 2008). It is preferable that a spectrum of white light emitted from the organic EL element has high maximum emission peaks in a blue range (430 nm to 485 nm), a green range (530 nm to 580 nm), and a yellow range (580 nm to 620 nm). It is more preferable that the spectrum has a maximum emission peak in a red range (650 nm to 700 nm) in addition to the above-described emission peaks.

<Infrared Absorber>

The compound (squarylium compound) represented by Formula (1a) described in the composition according to the present invention can be preferably used as an infrared absorber. A preferable range of the compound represented by Formula (1a) as the infrared absorber is the same as the preferable range of the squarylium compound.

The compound represented by Formula (1a) or the infrared absorber can be preferably used to form, for example, an infrared cut filter that shields light in a wavelength range of 700 to 1000 nm. In addition, the compound according to the present invention can be used as an infrared cut filter for a plasma display panel or a solid image pickup element, an optical filter such as a heat ray shielding film, or a photothermal conversion material such as a recordable optical disc (CD-R) or a flash melt fixing material. In addition, the compound according to the present invention can be used as an information display material for security ink or invisible barcode ink. In addition, the compound according to the present invention can also be used to form an infrared transmitting filter. In a case where the compound represented by Formula (1a) or the infrared absorber is used as an infrared transmitting filter, light (infrared light) having passed through the infrared transmitting filter is limited to infrared light on the longer wavelength side.

EXAMPLES

Hereinafter, the present invention will be described in detail using examples. Materials, used amounts, ratios, treatment details, treatment procedures, and the like shown in the following examples can be appropriately changed within a range not departing from the scope of the present invention. Accordingly, the scope of the present invention is not limited to the following specific examples. Unless specified otherwise, "part(s)" and "%" represent "part(s) by mass" and "mass %".

A compound used as an infrared absorber is the same as that the compound having the chemical structure described above regarding the infrared absorber.

<Measurement of Weight-Average Molecular Weight (Mw)>

The weight-average molecular weight (Mw) was a value in terms of polystyrene measured by gel permeation chromatography (GPC).

Kind of Column: TSKgel Super HZ4000 (manufactured by Tosoh Corporation, 4.6 mm (Inner diameter)×15 cm)

Developing solvent: tetrahydrofuran

Column temperature: 40° C.

Flow rate (sample injection volume): 60 µL

Device name: High-Speed GPC (HLC-8220GPC), manufactured by Tosoh Corporation

Calibration curve base resin: a polystyrene resin

Synthesis of Compound

Synthesis Example 1

Synthesis of Compound 1

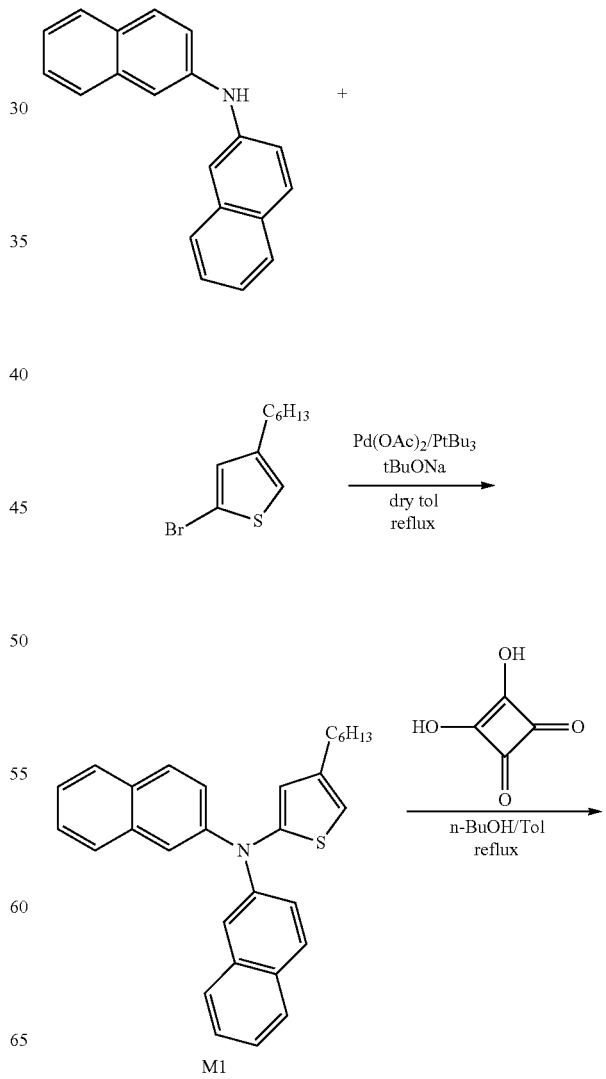

M1

-continued

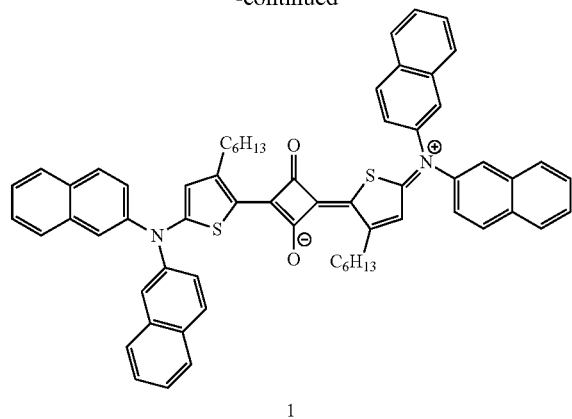

1

-continued

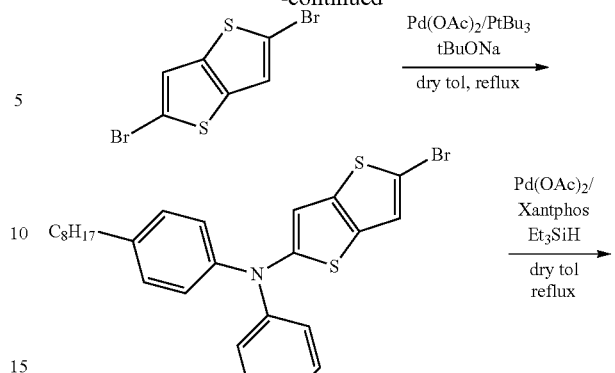

Synthesis of Intermediate M1:

palladium acetate (230 mg, 1.0 mmol), sodium tertiary butoxide (3.9 g, 40.4 mmol), and tri tertiary butyl phosphine (450 mg, 2.0 mmol) were added to 40 cm³ of toluene and were stirred at 60° C. for 10 minutes. The reaction solution was cooled to room temperature, 2,2'-dinaphthylamine (5.5 g, 20.2 mmol) and 2-bromo-4-hexylthiophene (5.0 g, 20.2 mmol) were added thereto, and the reaction solution was heated to reflux for 3 hours. The reaction solution was cooled to room temperature, was filtered through celite to remove an inorganic salt, and toluene (Tol) was removed under reduced pressure. The residue was purified by silica gel column chromatography (developing solvent: toluene/hexane), and the solution was removed under reduced pressure. As a result, an intermediate M1 was obtained (orange grease, 8.5 g, yield: 97%).

Synthesis of Compound 1

The intermediate M1 (8.5 g, 19.5 mmol) and squaric acid (0.92 g, 8.1 mmol) were heated to reflux for 12 hours under azeotropic dehydration in n-butanol/toluene (20 cc/60 cc).

The reaction solution was cooled, the solvent was removed by under reduced pressure, and the residue was ultrasonically dispersed in chloroform/methanol. The precipitated solid was filtered under reduced pressure. As a result, a desired compound 1 was obtained (green crystals, 5.9 g, yield: 78%).

Identification Data of Compound 1:

MALDI TOF-MASS (time-of-flight mass spectrometry) Calc for [M+H]+: 949.4, found: 949.3

NMR (400 MHz, CDCl₃): 0.91 (6H, t), 1.20 (8H, m), 1.32 (4H, m), 1.55 (4H, m), 3.22 (4H, t), 6.55 (2H, s), 7.44 (4H, d), 7.50 (8H, m), 7.73 (4H, m), 7.80-7.88 (12H, m)

Synthesis Example 2

Synthesis of Compound 2

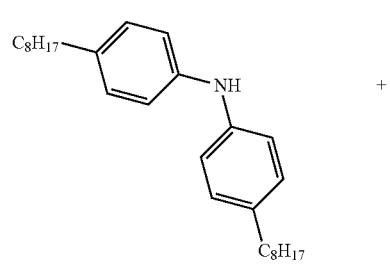

Synthesis of Intermediate M2:

An intermediate M2 was synthesized using the same synthesis method as that of the intermediate M1, except that 2,5-Dibromothieno[3,2-b]thiophene was used instead of 2-bromo-4-hexylthiophene, and di(4-octylphenyl)amine was used instead of 2,2'-dinaphthylamine.

Synthesis of Intermediate M3:

The intermediate M2 (1.0 g, 1.6 mmol), palladium acetate (18 mg, 0.082 mmol), 4,5-bis(diphenylphosphino)-9,9-dimethylxanthene (69 mg, 0.12 mmol, Xantphos), and triethylsilane (2.5 g, 21 mmol) were added to 16 cm³ of toluene and were heated to reflux for 7 hours. The reaction solution was cooled, the solvent was removed by distillation under reduced pressure, and the residue was purified by silica gel column chromatography (developing solvent: toluene/hexane). As a result, an intermediate M3 was obtained (yellow grease, 0.70 g, yield: 82%).

Synthesis of Compound 2

A compound 2 was synthesized using the same synthesis method as that of the compound 1, except that the intermediate M3 was used instead of the intermediate M1.

Identification Data of Compound 2:

MALDI TOF-MASS Calc for [M+H]+: 1141.6, found: 1141.6

Synthesis Example 3

Synthesis of Compound 3

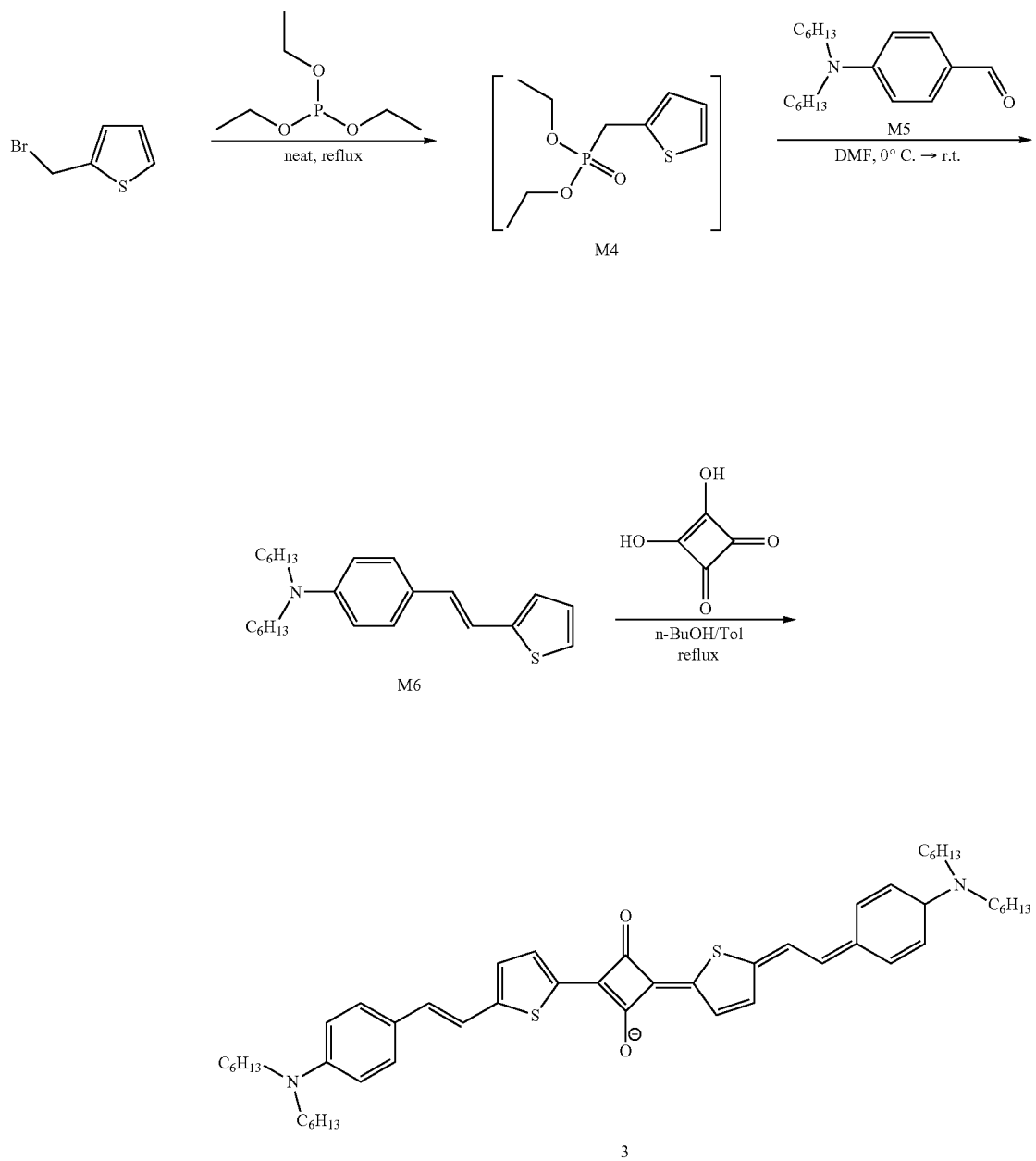

Synthesis of Intermediate M4:

2-bromomethyl thiophene (1.5 g, 8.6 mmol) and triethyl phosphite (1.44 g, 8.6 mmol) were heated at 160° C. for 2 hours. As a result, an intermediate M4 was obtained. The obtained intermediate M4 was used for the next reaction without being purified.

Synthesis of Intermediate M5:

An intermediate M5 was synthesized using a method described in "Dyes and Pigments", 2015, 120, 175-183.

Intermediate M6:

50 cm$^3$ of N,N-dimethylformamide (DMF) was added to the obtained intermediate M4, the solution was cooled in an ice bath at 0° C., sodium methoxide (1.4 g, 25.8 mmol) was added, and the solution was stirred for 30 minutes. 20 cm$^3$ of a DMF solution in which the intermediate M5 (2.5 g, 8.6 mmol) was dissolved was added dropwise. After the dropwise addition, the ice bath was removed, and the solution was stirred at room temperature for 3 hours. Water was poured into the reaction solution, and the precipitated solid was filtered and then washed with methanol. As a result, an intermediate M6 was obtained (light yellow crystals, 2.6 g, yield: 82%).

Synthesis of Compound 3

A compound 3 was synthesized using the same synthesis method as that of the compound 1, except that the intermediate M6 was used instead of the intermediate M1.

Identification Data of Compound 3:

MALDI TOF-MASS Calc for [M+H]+: 818.5, found: 818.4

Synthesis Example 4
Synthesis of Compound 4
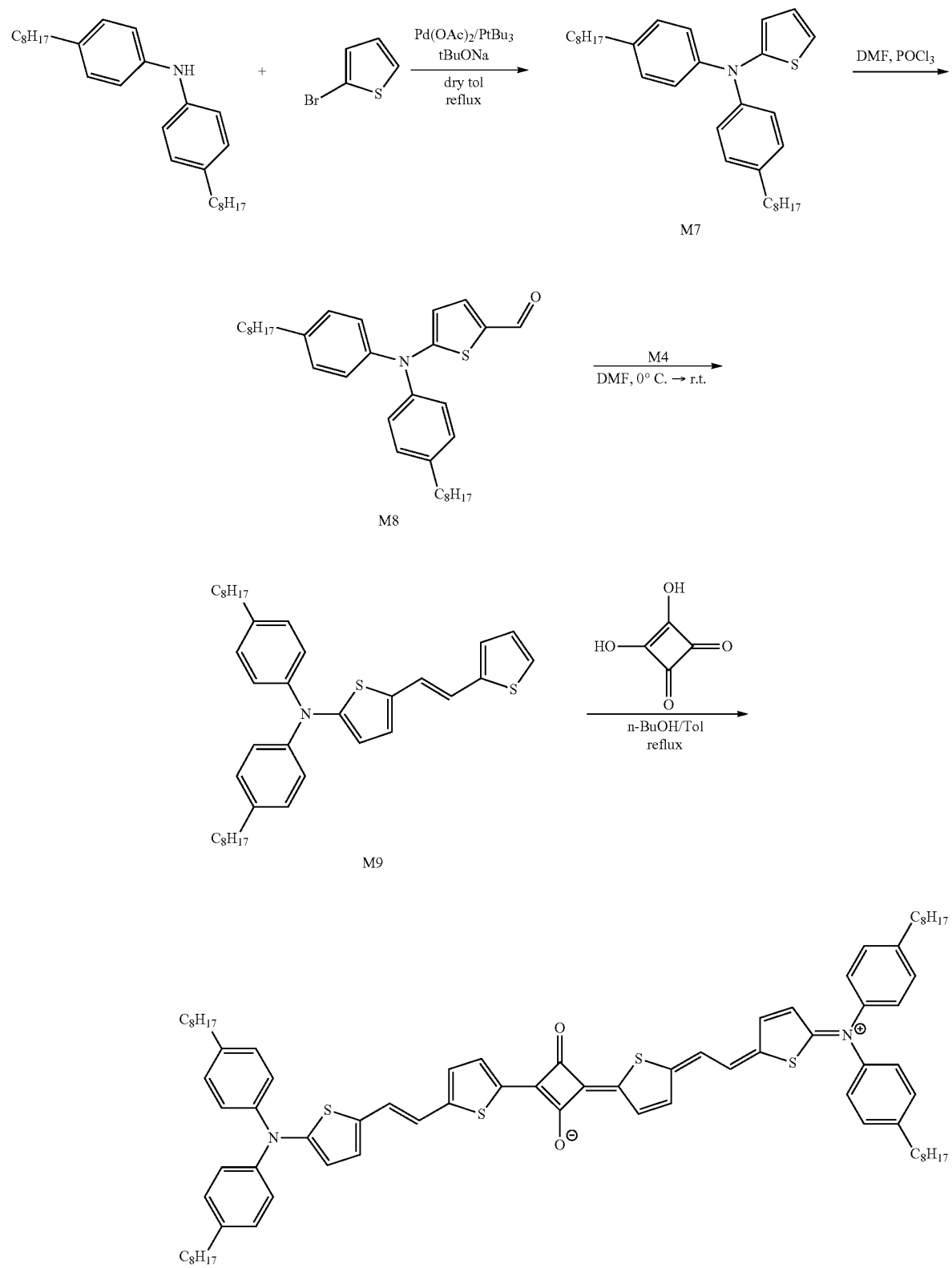

Synthesis of Intermediate M7:

An intermediate M7 was synthesized using the same synthesis method as that of the intermediate M2, except that 2-bromothiophene was used instead of 2-bromo-4-hexylthiophene.

Synthesis of Intermediate M8:

An intermediate M8 was synthesized from the intermediate M7 using a method described in Chem. Eur. J. 2007, 13, 9637-9646.

Synthesis of Intermediate M9:

An intermediate M9 was synthesized using the same synthesis method as that of the intermediate M6, except that the intermediate M8 was used instead of the intermediate M5.

Synthesis of Compound 4

A compound 4 was synthesized using the same synthesis method as that of the compound 1, except that the intermediate M9 was used instead of the intermediate M1.

Identification Data of Compound 4:

MALDI TOF-MASS Calc for [M+H]+: 1245.6, found: 1245.7

Synthesis Example 5

Synthesis of Compound 5

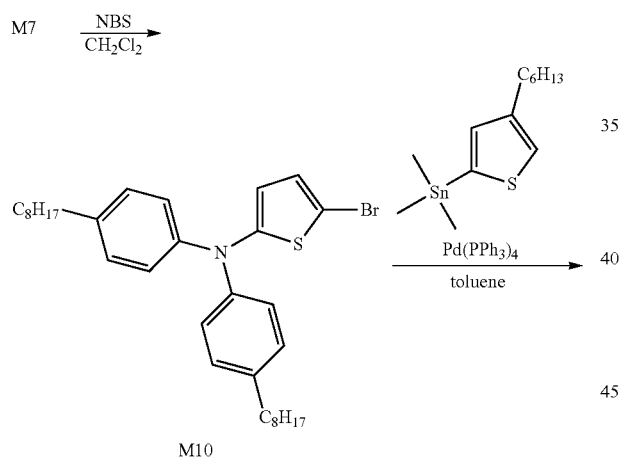

M10

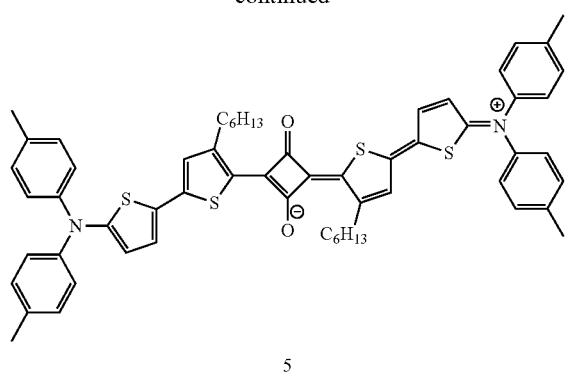

5

Synthesis of Intermediate M10:

An intermediate M10 was synthesized from the intermediate M7 using a method described in J. Photochem. Photobio. A2014, 294, 54-61. In the synthesis scheme, NBS is an abbreviation for N-bromosuccinimide.

Synthesis of Intermediate M11:

An intermediate M11 was synthesized from the intermediate M10 using a method described in EP2407465A1.

Synthesis of Compound 5

A compound 5 was synthesized using the same synthesis method as that of the compound 1, except that the intermediate M11 was used instead of the intermediate M1.

Identification Data of Compound 5:

MALDI TOF-MASS Calc for [M+H]+: 969.4, found: 969.4

Synthesis Example 6

Synthesis of Compound 6

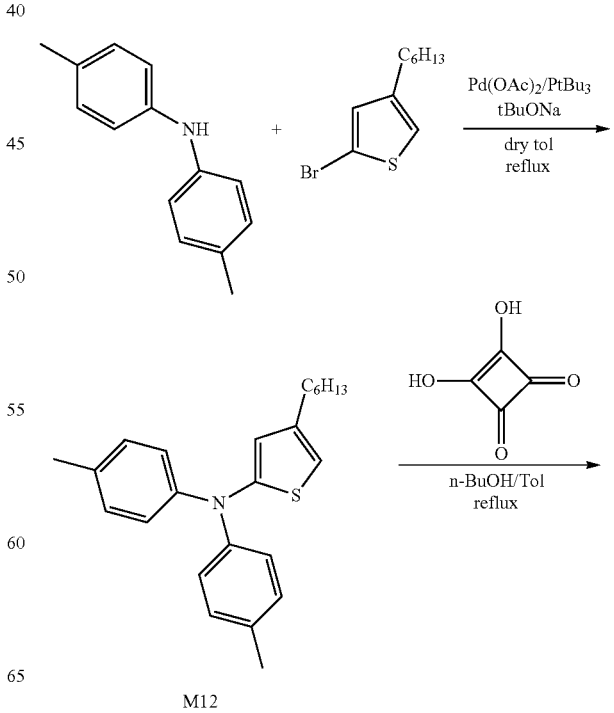

M11

M12

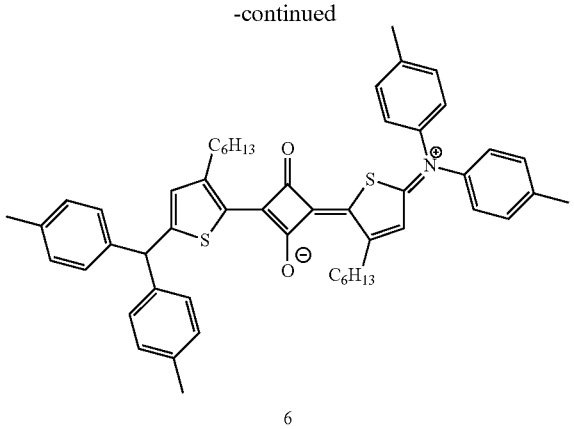

6

Synthesis of Intermediate M12:

An intermediate M12 was synthesized using the same synthesis method as that of the intermediate M1, except that p,p'-ditolylamine was used instead of 2,2'-dinaphthylamine.

Synthesis of Compound 6

A compound 6 was synthesized using the same synthesis method as that of the compound 1, except that the intermediate M12 was used instead of the intermediate M1.

Identification Data of Compound 6:

MALDI TOF-MASS Calc for [M+H]+: 805.4, found: 805.3

NMR (400 MHz, CDCl$_3$): 0.92 (6H, t), 1.18-1.27 (12H, m), 1.32 (4H, m), 2.36 (12H, s), 3.20 (4H, t), 6.33 (2H, s), 7.18 (16H, m)

<Absorption Maximum>

Each of the obtained compounds was dissolved in chloroform to prepare a solution having a concentration of 1 g/L. Next, the solution in which each of the compounds was dissolved was appropriately diluted such that an absorbance at an absorption maximum in an absorption spectrum thereof was in a range of 0.7 to 1.2, and the absorption maximum (λmax) thereof was measured using UV-1800 (manufactured by Shimadzu Corporation). The absorption maximum (λmax) of each of the compounds is shown in the following table.

<Solubility of Compound>

The solubility of each of the compounds in each of solvents (cyclohexanone, propylene glycol monomethyl ether acetate (PGMEA), toluene) at 25° C. was evaluated based on the following criteria.

A: the solubility of the compound in the solvent at 25° C. was 2 mass % or higher B: the solubility of the compound in the solvent at 25° C. was 1 mass % or higher and lower than 2 mass %

C: the solubility of the compound in the solvent at 25° C. was 0.5 mass % or higher and lower than 1 mass %

D: the solubility of the compound in the solvent at 25° C. was lower than 0.5 mass %

TABLE 2

| Compound | Absorption Maximum (nm) | Solubility Cyclohexanone | PGMEA | Toluene |
|---|---|---|---|---|
| Compound 1 | 719 nm | A | B | A |
| Compound 2 | 770 nm | A | B | B |
| Compound 3 | 845 nm | B | B | B |
| Compound 4 | 860 nm | A | B | B |
| Compound 5 | 720 nm | A | B | A |
| Compound 6 | 710 nm | A | B | A |

TABLE 2-continued

| Compound | Absorption Maximum (nm) | Solubility Cyclohexanone | PGMEA | Toluene |
|---|---|---|---|---|
| R-1 | 687 nm | C | D | C |
| R-2 | 653 nm | A | A | A |
| R-3 | 704 nm | B | D | B |

Regarding each of compounds R-1 to R-3, the absorption maximum was measured and the solubility was evaluated using the same methods as those of the compounds 1 to 6.

The compound R-1 is a compound described in DE4122563 and was synthesized using a method described in DE4122563. The compound R-2 is a compound described in JP2009-15114A and was synthesized using a method described in JP2009-15114A. The compound R-3 is a compound described in Chem. Eur. J., 2008, 14 11082-11091 and was synthesized using a method described in Chem. Eur. J., 2008, 14 11082-11091.

R-1

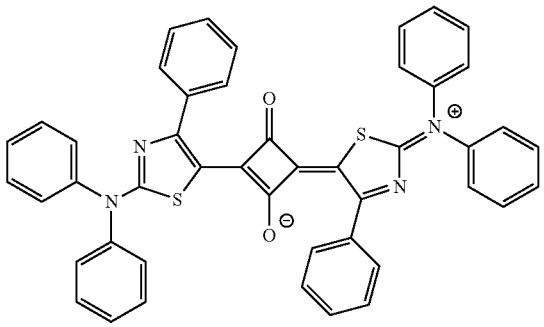

R-2

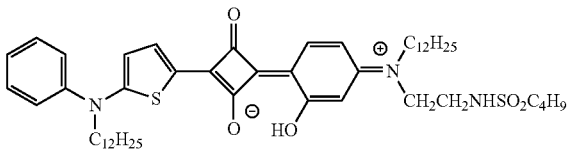

R-3

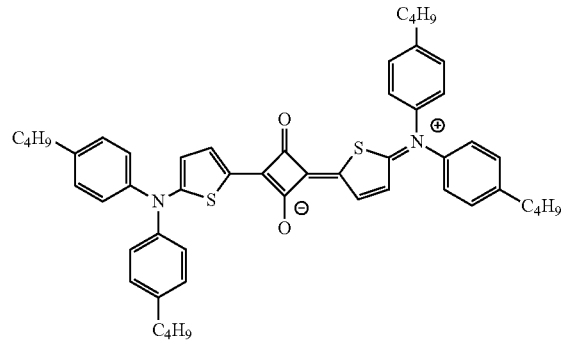

In the compounds 1 to 6, the absorption maximums were 700 nm or longer. Further, the solubility in the each of the solvents was excellent.

On the other hand, in the compounds R-1 and R-2, the absorption maximums were shorter than 700 nm. In addition, in the compounds R-1 and R-3, the solubility was insufficient.

<Preparation of Near Infrared Absorbing Composition>

Materials shown in each of the following compositions were mixed with each other to prepare a near infrared absorbing composition.

<Composition 1>

| | |
|---|---|
| Compound shown in the following table: | 2.3 parts |
| Resin 1: | 12.9 parts |
| Crosslinking compound: dipentaerythritol hexaacrylate (trade name: KAYARAD DPHA, manufactured by Nippon Kayaku Co., Ltd.): | 12.9 parts |
| Photopolymerization initiator: IRGACURE-OXE01 [2-(o-benzoyloxime)-1-[4-(phenylthio)phenyl]-1,2-octanedione] (manufactured by BASF SE): | 2.5 parts |
| Ultraviolet absorber: UV503 (manufactured by Daito Chemical Co., Ltd.): | 0.5 parts |
| Surfactant: the following mixture (Mw: 14000): | 0.04 parts |
| 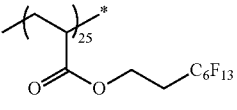 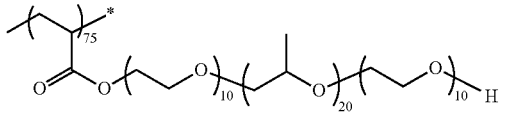 <br> 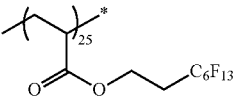 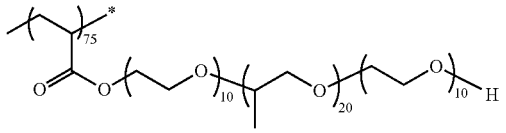 Mixture | |
| Polymerization inhibitor: p-methoxyphenol: | 0.006 parts |
| Cyclohexanone: | 49.6 parts |
| Propylene glycol monomethyl ether acetate: | 19.3 parts |

<Composition 2>
Compound shown in the following table: 2.8 parts
Resin 2: 10.5 parts
Crosslinking compound: dipentaerythritol hexaacrylate (trade name: KAYARAD DPHA, manufactured by Nippon Kayaku Co., Ltd.): 2.0 parts
Photopolymerization initiator: IRGACURE-OXE01 [2-(o-benzoyloxime)-1-[4-(phenylthio)phenyl]-1,2-octanedione] (manufactured by BASF SE): 2.2 parts
Ultraviolet absorber: UV503 (manufactured by Daito Chemical Co., Ltd.): 0.5 parts
Surfactant: MEGAFACE RS-72-K (manufactured by DIC Corporation): 2.3 parts
Polymerization inhibitor: p-methoxyphenol: 0.001 parts
Cyclohexanone: 74.5 parts
Propylene glycol monomethyl ether acetate: 5.3 parts
<Composition 3>
Compound shown in the following table: 2.8 parts
Resin 3 or resin 4: 14.7 parts
Ultraviolet absorber: UV503 (manufactured by Daito Chemical Co., Ltd.): 0.5 parts
Surfactant: MEGAFACE RS-72-K (manufactured by DIC Corporation): 2.3 parts
Cyclohexanone: 74.5 parts
Propylene glycol monomethyl ether acetate: 5.3 parts
Resin 1: a copolymer including benzyl methacrylate (BzMA) and methacrylic acid (MAA) (composition ratio (mass ratio): (BzMA/MAA)=(80/20), Mw=15000)
Resin 2: a copolymer including allyl methacrylate (Allyl-MA) and methacrylic acid (MAA) (composition ratio (mass ratio): (Allyl-MA/MAA)=(80/20), Mw=15000)
Resin 3: polystyrene (Aldrich, Mw=15000)
Resin 4: ARTON F4520 (manufactured by JSR Corporation)
<Preparation of Film>
Each of the compositions was applied to a glass substrate (1737, manufactured by Corning Inc.) using a spin coater such that the thickness of a dried film was 1.0 μm, and was heated (pre-baked) using a hot plate at 100° C. for 120 seconds.
Regarding the composition 1 and the composition 2, after pre-baking, the entire surface of the glass substrate was exposed using an i-ray stepper exposure device FPA-3000 i5+ (manufactured by Canon Corporation) at 500 mJ/cm².

Next, the glass substrate underwent puddle development at 23° C. for 60 seconds using a developing device CD-2060 (manufactured by Fujifilm Electronic Materials Co., Ltd.), and was rinsed with pure water. The glass substrate after rinsing was spin-dried and was heated (post-baked) using a hot plate at 200° C. for 300 seconds to obtain a cured film.
Regarding Examples 3 and 4, the dried film after pre-baking was used as it is for the evaluation.
<Evaluation of Coating Film>
The state of the obtained film was observed by visual inspection.
A: precipitation of the compound did not occur
B: precipitation of the compound occurred
<Absorption Maximum (λmax) of Film>
Using a spectrophotometer UV-3100PC (manufactured by Shimadzu Corporation), the absorption spectrum of the obtained film was measured, and the absorption maximum (λmax) of the film was measured.
<Evaluation of Infrared Shielding Properties>
The transmittance of each of the films at a wavelength of 700 nm was measured using a spectrophotometer U-4100 (manufactured by Hitachi High-Technologies Corporation). The infrared shielding properties were evaluated based on the following criteria. The results are shown in the following table.
A: transmittance at a wavelength of 700 nm≤5%
B: 5%<transmittance at a wavelength of 700 nm≤7%
C: 7%<transmittance at a wavelength of 700 nm≤10%
D: 10%<transmittance at a wavelength of 700 nm
<Evaluation of Visible Transparency>
The transmittance of each of the films at a wavelength of 450 to 600 nm was measured using a spectrophotometer U-4100 (manufactured by Hitachi High-Technologies Corporation). The visible transparency was evaluated based on the following criteria. The results are shown in the following table.
A: 95%≤minimum value of transmittance at a wavelength of 450 to 600 nm
B: 90%≤minimum value of transmittance at a wavelength of 450 to 600 nm<95%
C: 80%≤minimum value of transmittance at a wavelength of 450 to 600 nm<90%

D: minimum value of transmittance at a wavelength of 450 to 600 nm<80%

<Evaluation of Heat Resistance>

Each of the films was heated at 200° C. for 5 minutes, and a heat resistance test was performed. A ΔEab value of a color difference each of the films before and after the heat resistance test was measured using a colorimeter MCPD-1000 (manufactured by Otsuka Electronics Co., Ltd.). The heat resistance was evaluated based on the following criteria using the ΔEab value. The lower the ΔEab value, the higher the heat resistance.

The ΔEab value was obtained from the following color difference formula of CIE 1976 (L*, a*, b*) color space (Handbook of Color Science, p. 266, 1985, edited by The Color Science Association Of Japan).

$$\Delta Eab = \{(\Delta L^*)^2 + (\Delta a^*)^2 + (\Delta b^*)^2\}^{1/2}$$

(Criteria)
A: ΔEab value<3
B: 3≤ΔEab value<5
C: 5≤ΔEab value<10
D: 10≤ΔEab value<20
E: 20≤ΔEab value <Evaluation of Light Fastness>

The obtained film was irradiated with light at 10000 lux using a Xe lamp through an ultraviolet cut filter for 10 hours, and a light fastness test was performed. A ΔEab value of a color difference each of the films before and after the light fastness test was measured using a colorimeter MCPD-1000 (manufactured by Otsuka Electronics Co., Ltd.). The light fastness was evaluated based on the following criteria using the ΔEab value. The lower the ΔEab value, the higher the light fastness.

(Criteria)
A: ΔEab value<3
B: 3≤ΔEab value<5
C: 5≤ΔEab value<10
D: 10≤ΔEab value<20
E: 20≤ΔEab value On the other hand, in Comparative Examples 1 and 2, infrared shielding properties and visible transparency were poor.

In addition, in Examples 1 to 10, the chromatic colorant was further added. As a result, a filter having excellent transmittance in a wavelength range other than a specific visible range and infrared shielding properties and having excellent heat resistance and light fastness was obtained.

In addition, a favorable effect was obtained in a laminated film including a dielectric multi-layer film and a film which was obtained from each of the compositions according to Examples 1 to 10.

What is claimed is:

1. A near infrared absorbing composition comprising:
a squarylium compound represented by Formula (1) and having an absorption maximum of 700 nm or longer; and
a resin,

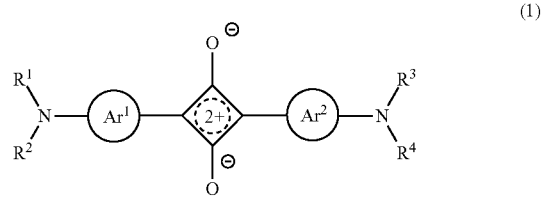

wherein in Formula (1),
Ar¹ and Ar² each independently represent
a fused ring selected from Formulae (2'),
a group in which two or more fused rings represented by Formula (2') are bonded to each other through a single bond,
a group in which two or more monocyclic rings represented by Formula (Ht) are bonded to each other through a single bond,

TABLE 3

| | Compound | Composition | Resin | Evaluation of Coating Film | Absorption Maximum of Film (nm) | Infrared Shielding Properties | Visible Transparency | Heat Resistance | Light Fastness |
|---|---|---|---|---|---|---|---|---|---|
| Example 1 | Compound 1 | Composition 1 | Resin 1 | A | 720 nm | A | A | A | A |
| Example 2 | Compound 1 | Composition 2 | Resin 2 | A | 722 nm | A | A | A | A |
| Example 3 | Compound 1 | Composition 3 | Resin 3 | A | 721 nm | A | A | A | A |
| Example 4 | Compound 1 | Composition 3 | Resin 4 | A | 721 nm | A | A | A | A |
| Example 5 | Compound 2 | Composition 1 | Resin 1 | A | 770 nm | A | A | A | A |
| Example 6 | Compound 3 | Composition 1 | Resin 1 | A | 850 nm | A | A | A | A |
| Example 7 | Compound 4 | Composition 1 | Resin 1 | A | 870 nm | A | A | A | A |
| Example 8 | Compound 5 | Composition 1 | Resin 1 | A | 730 nm | A | B | A | A |
| Example 9 | Compound 6 | Composition 1 | Resin 1 | A | 710 nm | B | B | B | B |
| Example 10 | Compound R-3 | Composition 1 | Resin 1 | B | 705 nm | B | C Scattering Occurred | C | C |
| Comparative Example 1 | Compound R-1 | Composition 1 | Resin 1 | B | 690 nm | D | D Scattering Occurred | C | C |
| Comparative Example 2 | Compound R-2 | Composition 1 | Resin 1 | A | 655 nm | D | D | D | D |

The following can be seen from the results. In Examples, infrared shielding properties and visible transparency were excellent. In particular, in Examples 1 to 9 in which the compounds 1 to 6 were used, infrared shielding properties and visible transparency were further improved. Further, during the formation of the coating film, precipitation of the compound did not occur, and the properties of the coating film were excellent. Further, heat resistance and light fastness were also excellent.

a divalent conjugated group including a fused ring selected from Formulae (2') and a linking group, or
a divalent conjugated group having a monocyclic thiazole ring and a linking group, wherein the divalent conjugated group having a monocyclic thiazole ring and a linking group is not a divalent conjugated group including a monocyclic thiazole ring and a single bond,
R¹ to R⁴ each independently represent an alkyl group, an aryl group or a heteroaryl group, $R^1$ may be bonded to $R^2$ or $Ar^1$ to form a ring, and $R^3$ may be bonded to $R^4$ or $Ar^2$ to form a ring,

(Ht)

in Formula (Ht),
$X^1$ and $X^2$ each independently represent $CR^x$,
$R^x$ represents a hydrogen atom or a substituent,
$Y^1$ represents a chalcogen atom, and
* represents a direct bond,

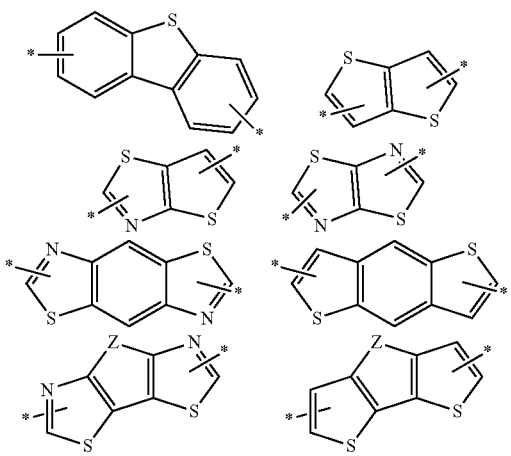
(2')

in Formulae (2'),
Z represents —$CR_2$—, —CR=CR—, —$SiR_2$—, —CO—, —S—, —SO—, and —$SO_2$—,
* represents a direct bond, and
R represents a hydrogen atom or a substituent.

2. The near infrared absorbing composition according to claim 1,
wherein in the squarylium compound, a plane including $Ar^1$ and $Ar^2$ of Formula (1) includes a π-conjugated plane having 16 to 54 atoms.

3. The near infrared absorbing composition according to claim 1,
wherein at least one of $R^1$, $R^2$, $R^3$, or $R^4$ represents an aryl group or a heteroaryl group in which the number of atoms constituting a ring is 8 or more.

4. The near infrared absorbing composition according to claim 1,
wherein at least one of $R^1$, $R^2$, $R^3$, or $R^4$ represents a naphthyl group.

5. The near infrared absorbing composition according to claim 1,
wherein $Ar^1$ and $Ar^2$ each independently represent a divalent conjugated group which has a π-conjugated plane having 8 or more atoms.

6. The near infrared absorbing composition according to claim 5,
wherein $Ar^1$ and $Ar^2$ each independently represent the fused ring selected from Formulae (2').

7. The near infrared absorbing composition according to claim 1,
wherein at least one selected from the group consisting of $Ar^1$, $Ar^2$, $R^1$, $R^2$, $R^3$, and $R^4$ has a group represented by the following Formula (W),

—$S^1$-$L^1$-$T^1$ (W)

in Formula (W), $S^1$ represents a single bond, an arylene group, or a heteroarylene group,
$L^1$ represents an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, —$OR^{L2}$—, or a group including a combination of two or more selected from the group consisting of an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, and —$OR^{L2}$—,
$R^{L1}$ represents a hydrogen atom or an alkyl group,
$R^{L2}$ represents an alkylene group,
$T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group,
in a case where $S^1$ represents a single bond, $L^1$ represents an alkylene group, and $T^1$ represents an alkyl group, the total number of carbon atoms included in $L^1$ and $T^1$ is 5 or more, and
in a case where $S^1$ represents an arylene group or a heteroarylene group, the total number of carbon atoms included in $L^1$ and $T^1$ is 5 or more.

8. A film which is formed of the near infrared absorbing composition according to claim 1.

9. An infrared cut filter which is formed of the near infrared absorbing composition according to claim 1.

10. A solid image pickup element comprising the infrared cut filter according to claim 9.

11. A compound which is represented by the following Formula (1a),

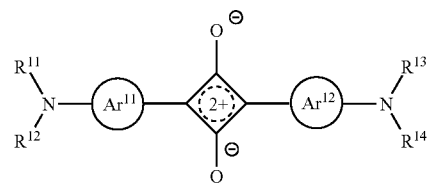
(1a)

wherein in Formula,
$Ar^{11}$ and $Ar^{12}$ each independently represent a fused ring selected from Formulae (2'),
$R^{11}$ to $R^{14}$ each independently represent an alkyl group, an aryl group, or a heteroaryl group,
$R^{11}$ may be bonded to $R^{12}$ or $Ar^{11}$ to form a ring,
$R^{13}$ may be bonded to $R^{14}$ or $Ar^{12}$ to form a ring,

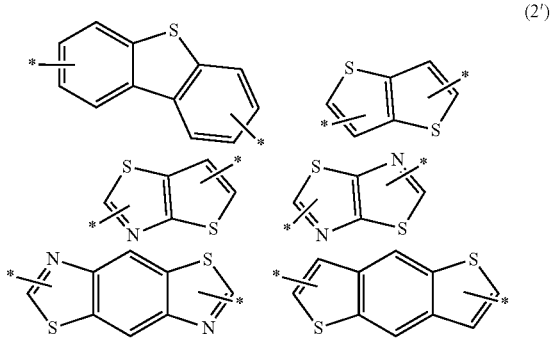
(2')

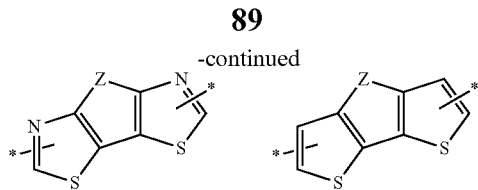

in Formulae (2'),
Z represents —$CR_2$—, —CR=CR—, —$SiR_2$—, —CO—, —S—, —SO—, and —$SO_2$—,
* represents a direct bond, and
R represents a hydrogen atom or a substituent.

12. The compound according to claim 11,
wherein at least one of $R^{11}$, $R^{12}$, $R^{13}$, or $R^{14}$ represents a naphthyl group.

13. The compound according to claim 11,
wherein at least one selected from the group consisting of $Ar^{11}$, $Ar^{12}$, $R^{11}$, $R^{12}$, $R^{13}$, and $R^{14}$ has a group represented by the following Formula (W),

—$S^1$-$L^1$-$T^1$ (W)

in Formula (W), $S^1$ represents a single bond, an arylene group, or a heteroarylene group,
$L^1$ represents an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, —$OR^{L2}$—, or a group including a combination of two or more selected from the group consisting of an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, and —$OR^{L2}$—,
$R^{L1}$ represents a hydrogen atom or an alkyl group,
$R^{L2}$ represents an alkylene group,
$T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group,
in a case where $S^1$ represents a single bond, $L^1$ represents an alkylene group, and $T^1$ represents an alkyl group, the total number of carbon atoms included in $L^1$ and $T^1$ is 5 or more, and
in a case where $S^1$ represents an arylene group or a heteroarylene group, the total number of carbon atoms included in $L^1$ and $T^1$ is 5 or more.

14. The near infrared absorbing composition according to claim 1,
wherein the resin has an acid group.

15. The near infrared absorbing composition according to claim 1, further comprising:
a compound which has a group having an ethylenically unsaturated bond, and
a photopolymerization initiator.

16. The near infrared absorbing composition according to claim 1,
wherein $Ar^1$ and $Ar^2$ each independently represent a divalent conjugated group represented by Formula (A)

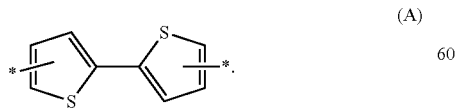

(A)

17. A near infrared absorbing composition comprising:
a squarylium compound represented by Formula (1) and having an absorption maximum of 700 nm or longer; and a resin,

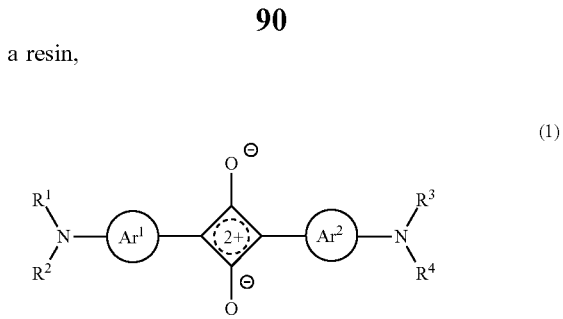

(1)

wherein in Formula (1),
$Ar^1$ and $Ar^2$ each independently represent
 a monocyclic ring represented by Formula (Ht),
 a fused ring selected from Formulae (2),
 a group in which two or more monocyclic rings represented by Formula (Ht) are bonded to each other through a single bond,
 a divalent conjugated group including a fused ring selected from Formulae (2) and a linking group, or
 a divalent conjugated group consisting of a monocyclic ring represented by Formula (Ht) and a methine chain having one to four methine groups,
$R^1$ to $R^4$ each independently represent an aryl group or a heteroaryl group,
R may be bonded to $R^2$ or $Ar^1$ to form a ring, and
$R^3$ may be bonded to $R^4$ or $Ar^2$ to form a ring,

(Ht)

in Formula (Ht),
$X^1$ and $X^2$ each independently represent $CR^x$,
$R^x$ represents a hydrogen atom or a substituent,
$Y^1$ represents a chalcogen atom, and
* represents a direct bond,

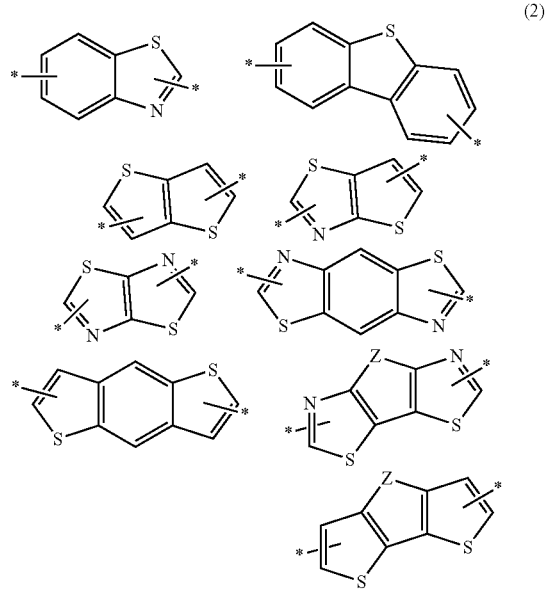

(2)

in Formula (2),

Z represents —Cr$_2$—, —CR=CR—, —SiR$_2$—, —CO—, —S—, —SO—, and —SO$_2$—,

* represent a direct bond, and

R represents a hydrogen atom or a substituent.

18. The near infrared absorbing composition according to claim 17,
wherein in the squarylium compound, a plane including Ar$^1$ and Ar$^2$ of Formula (1) includes a π-conjugated plane having 16 to 54 atoms.

19. The near infrared absorbing composition according to claim 17,
wherein at least one of R$^1$, R$^2$, R$^3$, or R$^4$ represents an aryl group or a heteroaryl group in which the number of atoms constituting a ring is 8 or more.

20. The near infrared absorbing composition according to claim
wherein at least one of R$^1$, R$^2$, R$^3$, or R$^4$ represents a naphthyl group.

21. The near infrared absorbing composition according to claim 17,
wherein Ar$^1$ and Ar$^2$ each independently represent a divalent conjugated group which has a π-conjugated plane having 8 or more atoms.

22. The near infrared absorbing composition according to claim 21,
wherein Ar$^1$ and Ar$^2$ each independently represent the fused ring selected from Formulae (2).

23. The near infrared absorbing composition according to claim 17,
wherein at least one selected from the group consisting of Ar$^1$, Ar$^2$, R$^1$, R$^2$, R$^3$, and R$^4$ has a group represented by the following Formula (W),

—S$^1$-L$^1$-T$^1$  (W)

in Formula (W), S$^1$ represents a single bond, an arylene group, or a heteroarylene group, L$^1$ represents an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, —OR$^{L2}$—, or a group including a combination of two or more selected from the group consisting of an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, and —OR$^{L2}$—, R$^{L1}$ represents a hydrogen atom or an alkyl group, R$^{L2}$ represents an alkylene group, T$^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group, in a case where S$^1$ represents a single bond, L$^1$ represents an alkylene group, and T$^1$ represents an alkyl group, the total number of carbon atoms included in L$^1$ and T$^1$ is 5 or more, and in a case where S$^1$ represents an arylene group or a heteroarylene group, the total number of carbon atoms included in L$^1$ and T$^1$ is 5 or more.

24. The near infrared absorbing composition according to claim 17,
wherein the squarylium compound is a compound represented by the following Formula (1a),

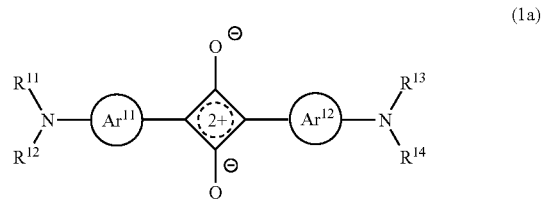

(1a)

Ar$^{11}$ and Ar$^{12}$ each independently represent a thiophene ring or the fused ring selected from Formulae (2), R$^{11}$ to R$^{14}$ each independently represent an alkyl group, an aryl group, or a heteroaryl group, R$^{11}$ may be bonded to R$^{12}$ or Ar$^{11}$ to form a ring, R$^{13}$ may be bonded to R$^{14}$ or Ar$^{12}$ to form a ring, in a case where Ar$^{11}$ represents the thiophene ring, at least one of R$^{11}$ or R$^{12}$ represents an aryl group having 8 or more atoms, or a heteroaryl group, and in a case where Ar$^{12}$ represents the thiophene ring, at least one of R$^{13}$ or R$^{14}$ represents an aryl group having 8 or more atoms, or a heteroaryl group.

25. The near infrared absorbing composition according to claim 17,
wherein Ar$^1$ and Ar$^2$ each independently represent a divalent conjugated group represented by Formula (A)

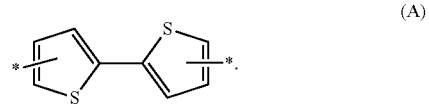

(A)

26. The near infrared absorbing composition comprising according to claim 17,
wherein Ar$^1$ and Ar$^2$ each independently represent a group consisting of a thiophene ring and a methine chain having one to four methine groups.

* * * * *